United States Patent
Kohno et al.

(10) Patent No.: US 7,456,157 B2
(45) Date of Patent: Nov. 25, 2008

(54) AMINOPHOSPHONIC ACID DERIVATIVES, ADDITION SALTS THEREOF AND S1P RECEPTOR MODULATORS

(75) Inventors: Yasushi Kohno, Tochigi (JP); Kiyoaki Tanaka, Tochigi (JP); Kazuhiko Kuriyama, Tochigi (JP); Wataru Hori, Tochigi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 306 days.

(21) Appl. No.: 10/545,790

(22) PCT Filed: Feb. 18, 2004

(86) PCT No.: PCT/JP2004/001783

§ 371 (c)(1),
(2), (4) Date: Aug. 17, 2005

(87) PCT Pub. No.: WO2004/074297

PCT Pub. Date: Sep. 2, 2004

(65) Prior Publication Data

US 2006/0160771 A1 Jul. 20, 2006

(30) Foreign Application Priority Data

Feb. 18, 2003 (JP) ............... 2003-039269

(51) Int. Cl.
*A61K 31/66* (2006.01)
*C07F 9/02* (2006.01)

(52) U.S. Cl. .................. 514/114; 558/166; 558/169

(58) Field of Classification Search ............. 514/114; 558/166, 169
See application file for complete search history.

(56) References Cited

U.S. PATENT DOCUMENTS

| | | | |
|---|---|---|---|
| 5,447,922 | A | 9/1995 | Lawrence et al. |
| 7,179,817 | B2 | 2/2007 | Seko et al. |
| 7,288,558 | B2 | 10/2007 | Nakade et al. |
| 2004/0067908 | A1 | 4/2004 | Nakade et al. |
| 2004/0224941 | A1 | 11/2004 | Seko et al. |
| 2004/0235794 | A1 | 11/2004 | Nakade et al. |
| 2007/0088027 | A1 | 4/2007 | Seko et al. |

FOREIGN PATENT DOCUMENTS

| | | |
|---|---|---|
| JP | 2003-137894 | 5/2003 |
| WO | 01/98301 | 12/2001 |
| WO | 02/18395 | 3/2002 |
| WO | 02/062389 | 8/2002 |
| WO | 02/064616 | 8/2002 |
| WO | 02/076995 | 10/2002 |
| WO | 02/092068 | 11/2002 |
| WO | 03/020313 | 3/2003 |
| WO | 03/040097 | 5/2003 |
| WO | 03/051876 | 6/2003 |
| WO | 03/061567 | 7/2003 |
| WO | 03/062248 | 7/2003 |
| WO | 03/062252 | 7/2003 |
| WO | 03/073986 | 9/2003 |
| WO | 2004/024673 | 3/2004 |
| WO | WO2004074297 | * 9/2004 |

OTHER PUBLICATIONS

Y. Igarashi, "Sphingosine-1-phosphate as an intercellular signaling molecule", Ann. N.Y. Acad. Sci., 845, 19, 1998, abstract only.

Yoh Takuwa et al., "Subtype-specific, differential activities of the EDG family receptors for sphingosine-1-phosphate, a novel lysophospholipid mediator", Molecular and Cellular Endocrinology, vol. 177, pp. 3-11, 2001.

Hiroshi Okazaki et al., "Molecular Cloning of a Novel Putative G Protein-Coupled Receptor Expressed in the Cardiovascular System", Biochemical and Biophysical Research Communications, vol. 190, No. 3, pp. 1104-1109, Feb. 15, 1993.

Suzanne Mandala et al., "Alteration of Lymphocyte Trafficking by Sphingosine-1-Phosphate Receptor Agonists", Science, vol. 296, pp. 346-349, Apr. 12, 2002.

Volker Brinkmann et al., "The Immune Modulator FTY720 Targets Sphingosine-1-Phosphate Receptors", The Journal of Biological Chemistry, vol. 277, No. 24, pp. 21453-21457, Jun. 14, 2002.

* cited by examiner

*Primary Examiner*—Rei-tsang Shiao
(74) *Attorney, Agent, or Firm*—Wenderoth, Lind & Ponack, L.L.P.

(57) ABSTRACT

Aminophosphonic acid derivatives (e.g., 2-amino-5-[4-(3-benzyloxyphenylthio)-2-chlorophenyl]-2-methylpentylphosphonate monoester) are represented by the following general formula (1):

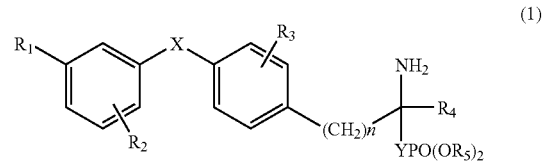

and act as effective S1P receptor modulators while posing less side effects.

12 Claims, No Drawings

AMINOPHOSPHONIC ACID DERIVATIVES, ADDITION SALTS THEREOF AND S1P RECEPTOR MODULATORS

The application is a 317 of PCT/JP04/01783 filed on Feb. 18, 2004

TECHNICAL FIELD

The present invention relates to aminophosphonic acid derivatives, salts and hydrates thereof that are useful as modulators of sphingosine-1-phosphate (S1P) receptor.

BACKGROUND ART

| | |
|---|---|
| Patent Article 1 | WO pamphlet 0198301 |
| Patent Article 2 | WO pamphlet 03020313 |
| Patent Article 3 | WO pamphlet 02092068 |
| Patent Article 4 | WO pamphlet 0218395 |
| Patent Article 5 | WO pamphlet 02076995 |
| Patent Article 6 | Japanese Patent Laid-Open |

Publication No. Hei 2003-137894

| | |
|---|---|
| Patent Article 7 | WO Pamphlet 03040097 |
| Patent Article 8 | WO Pamphlet 02064616 |
| Patent Article 9 | WO Pamphlet 02062389 |
| Patent Article 10 | WO Pamphlet 03051876 |
| Patent Article 11 | WO Pamphlet 03061567 |
| Patent Article 12 | WO Pamphlet 03062248 |
| Patent Article 13 | WO Pamphlet 03062252 |
| Patent Article 14 | WO Pamphlet 03073986 |

Non-Patent Article 1 Y. Takuma et al., Mol. Cell. Endocrinol., 177, 3(2001)

Non-Patent Article 2 Y. Igarashi, Ann, N.Y. Acad. Sci., 845, 19(1998)

Non-Patent Article 3 H. Okazaki et al., Biochem. Biophs. Res. Commun., 190, 1104(1993)

Non-Patent Article 4 S. Mandala et al., Science, 296, 346 (2002)

Non-Patent Article 5 V. Brinkmann et al., J. Biol. Chem., 277, 21453(2002)

Sphingosine-1-phosphate (referred to simply as S1P, hereinafter), which was previously considered a mere intermediate product in the metabolism of sphingosine, has proven to have an ability to facilitate cell growth and regulate cell motility. Studies have now shown that S1P, a previously unknown lipid mediator, is involved in a wide range of physiological actions, including apoptisis, modification of cell morphology and vascular contraction (Non-Patent Article 1 and Non-Patent Article 2). The lipid acts both as an intracellular second messenger and as an intercellular mediator; its role as an intercellular mediator has been particularly intensively studied. S1P induces signal transduction via a family of cell membrane G-protein-coupled receptors designated as Edg (which stands for Endothelial Differential Gene) (Non-Patent Article 1 and Non-Patent Article 3). Currently known subtypes of S1P receptors are Edg-1, Edg-3, Edg-5, Edg-6 and Edg-8, which are also referred to as $S1P_1$, $S1P_3$, $S1P_2$, $S1P_4$ and $S1P_5$, respectively.

Many studies of these S1P receptors suggest that S1P receptor modulators, which bind to these receptors and act as agonists or antagonists of S1P receptors, are effective against a broad spectrum of diseases. For example, compounds that act on Edg-5 have been shown effective against arteriosclerosis, renal fibrosis, pulmonary fibrosis and hepatic fibrosis (Patent Article 1). Compounds that act on Edg-1, Edg-3 or Edg-5 have been shown to be effective therapeutic or prophylactic agents against various respiratory diseases, including chronic bronchial asthma, diffuse pulmonary hamartoangiomyomatosis, adult respiratory distress syndrome (ARDS), chronic obstructive pulmonary disease (COPD), interstitial pneumonia, idiopathic interstitial pneumonia, lung cancer and hypersensitivity pneumonitis (Patent Article 2). In addition, compounds that act as Edg-1 agonists have been shown to be effective therapeutic or prophylactic agents for peripheral vascular diseases, such as arteriosclerosis obliterans, thromboangiitis obliterans, Buerger's disease and diabetic neuropathy, septicemia, angiitis, nephritis, pneumonia, cerebral infarction, myocardial infarction, edema, arteriosclerosis, varicose veins, such as piles, anal fissure and anal fistula, dissecting arterial aneurysm, stenocardia, DIC, pleuritis, congestive heart failure, multiple organ failure, bed sore, burn, ulcerative colitis, Crohn's disease, heart transplantation, kidney transplantation, skin transplantation, liver transplantation, bone marrow transplantation, osteoporosis, chronic hepatitis, hepatic cirrhosis, chronic renal failure and glomerulosclerosis (Patent Article 3). Furthermore, compounds that act as agonists of S1P receptors have been shown to modulate the migration of leukocytes (Non-Patent Article 4 and Non-Patent Article 5). Moreover, the derivatives mentioned in the aforementioned Non-Patent Articles have been shown effective not only against various organ transplants and GVHD, but also against autoimmune diseases, such as rheumatoid arthritis, lupus nephritis, systemic lupus erythematosus, Hashimoto's disease, multiple sclerosis, myasthenia gravis, type I and type II diabetes and Crohn's disease, allergic diseases, such as atopic dermatitis, allergic rhinitis, allergic conjunctivitis, allergic contact dermatitis, and inflammatory diseases, such as inflammatory bowel disease and ulcerative colitis (Patent Article 4 and Patent Article 5). Phosphoric acid derivatives similar to what are described in Patent Articles 4 and 5 and act as antagonists of S1P receptors are described in Patent Article 6. Other S1P receptor modulators are disclosed in Patent Articles 7, 8, 9 and 10.

In the course of the studies to develop compounds that have an ability to modulate S1P receptors, which are involved in the onset of various disorders, the present inventors have drawn the attention to aminophosphinic acid derivatives having different structures from previously known compounds and have made an effort in searching for novel modulators of S1P receptors. Quite recently, S1P receptor agonists having an amino group along with a phosphonic acid unit were disclosed in Patent Articles 11, 12 and 13. Each of these compounds has a structure in which the amino group is integrated in their linking backbone. This structure differs from the structure of the compounds of the present invention, which essentially has the form of β-aminophosphonic acid or γ-aminophosphonic acid in which an amino group exists on the linking backbone. Patent Article 14 describes similar compounds but the compounds of the present invention are not included.

DISCLOSURE OF THE INVENTION

It is thus an objective of the present invention to provide an aminophophonic acid derivative that can effectively modulate S1P receptors with less side effects.

The present inventors have conducted extensive studies to find compounds that have an ability to modulate S1P receptors and are highly safe. As a result, the inventors have found that certain aminophosphonic acid derivatives with a diarylsulfide or diarylether group that have a different structure from any of previously known S1P receptor modulators act as potent modulators of S1P receptors. It is this finding that led to the present invention.

Accordingly, the present invention provides an S1P receptor modulator containing as an active ingredient at least one of aminophosphonic acid derivatives represented by the following general formula (1):

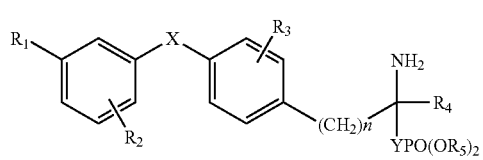

(1)

[wherein $R_1$ is a hydrogen atom, a halogen atom, a halogenated or unhalogenated lower alkyl group having 1 to 4 carbon atoms, a hydroxy group, a phenyl group, an aralkyl group, a lower alkoxy group having 1 to 4 carbon atoms, a trifluoromethyloxy group, a substituted or unsubstituted phenoxy group, a cyclohexylmethyloxy group, a substituted or unsubstituted aralkyloxy group, a pyridylmethyloxy group, a cinnamyloxy group, a naphthylmethyloxy group, a phenoxymethyl group, a hydroxymethyl group, a hydroxyethyl group, a lower alkylthio group having 1 to 4 carbon atoms, a lower alkylsulfinyl group having 1 to 4 carbon atoms, a lower alkylsulfonyl group having 1 to 4 carbon atoms, a benzylthio group, an acetyl group, a nitro group or a cyano group; $R_2$ is a hydrogen atom, a halogen atom, a halogenated or unhalogenated lower alkyl group having 1 to 4 carbon atoms, a lower alkoxy group having 1 to 4 carbon atoms, an aralkyl group or an aralkyloxy group; $R_3$ is a hydrogen atom, a halogen atom, a trifluoromethyl group, a lower alkyl group having 1 to 4 carbon atoms, a lower alkoxy group having 1 to 4 carbon atoms, a hydroxy group, a benzyloxy group, a phenyl group, a lower alkoxymethyl group having 1 to 4 carbon atoms or a lower alkylthio group having 1 to 4 carbon atoms; $R_4$ is a hydrogen atom, a halogen atom, a lower alkyl group having 1 to 4 carbon atoms, a lower alkoxymethyl group having 1 to 4 carbon atoms, a lower alkylthiomethyl group having 1 to 4 carbon atoms, a hydroxymethyl group, a phenyl group or an aralkyl group; $R_5$ is a hydrogen atom or a lower alkyl group having 1 to 4 carbon atoms; X is O, S, SO or $SO_2$; Y is —$CH_2O$—, —$CH_2$—, —CH=CH—, —CH=CF—, —$CH_2CH_2$—, —$CH_2CFH$—, —$CH_2CF_2$— or —CH(OH)$CF_2$—; and n is an integer from 1 to 4], and an optical isomer, and a pharmaceutically acceptable salt and a hydrate thereof.

More specifically, (I) the present invention provides: an aminophosphonic acid derivative represented by the following general formula (1):

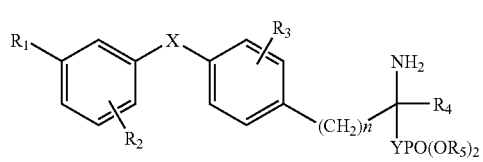

(1)

[wherein $R_1$, $R_2$, $R_3$, $R_4$, $R_5$, Y and n are as defined above], and an optical isomer, and a pharmaceutically acceptable salt and a hydrate thereof;

(II) 2-aminophosphonic acid monoester derivative represented by the following general formula (1a):

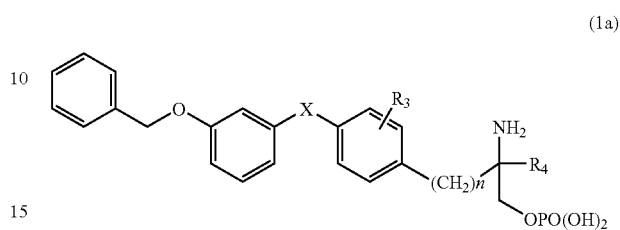

(1a)

[wherein $R_3$, $R_4$, X and n are as defined above], and the optical isomer, and the pharmaceutically acceptable salt and the hydrate thereof;

(III) 2-aminophosphonic acid monoester derivative represented by the general formula (1a) and the optical isomer, and the pharmaceutically acceptable salt and the hydrate thereof;

(IV) 3-aminophosphonic acid derivative represented by the following general formula (1b):

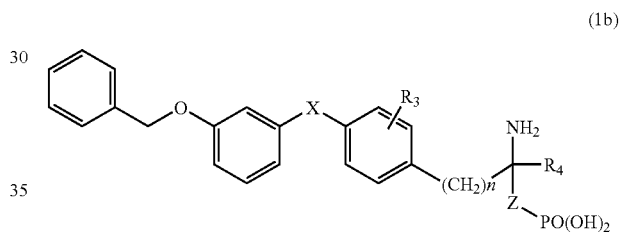

(1b)

[wherein z is $CH_2$—, —CH=CH—, —CH=CF—, —$CH_2CH_2$—, —$CH_2CHF$—, —$CH_2CF_2$— or —CH(OH)$CF_2$—; and $R_3$, $R_4$, X and n are as defined above], and the optical isomer, and the pharmaceutically acceptable salt and the hydrate thereof;

(V) 3-aminophosphonic acid derivative represented by the general formula (1b), and the optical isomer, and the pharmaceutically acceptable salt and the hydrate thereof, wherein $R_3$ is a chlorine atom; and (VI) An S1P receptor modulator containing as an active ingredient at least one of the compounds of (I) to (V) above.

The compounds of the general formulae (1), (1a) and (1b) are novel compounds.

Among preferred compounds of the present invention are aminophosphonic acid ester derivatives according to claim 1, including 1) 2-amino-5-[4-(3-benzyloxyphenylthio)-2-chlorophenyl]-2-methylpentylphosphonic acid monoester, 2) 2-amino-4-[4-(3-benzyloxyphenylthio)-2-chlorophenyl]-2-methylbutylphosphonic acid monoester, 3) 2-amino-5-[4-(3-benzyloxyphenylthio)-2-chlorophenyl]-2-hydroxymethylpentylphosphonic acid monoester, 4) 2-amino-4-[4-(3-benzyloxyphenylthio)-2-chlorophenyl]-2-hydroxymethylbutylphosphonic acid monoester, 5) 3-amino-5-[4-(3-benzyloxyphenylthio)-2-chlorophenyl]-3-hydroxymethylpentylphosphonic acid and 6) 3-amino-6-[4-(3-benzyloxyphenylthio)-2-chlorophenyl]-3-hydroxymethylhexylphosphonic acid, and pharmaceutically acceptable salts and hydrates thereof.

BEST MODE FOR CARRYING OUT THE INVENTION

Pharmaceutically acceptable alkaline salts of the compounds represented by the general formula (1) according to the present invention include sodium salts, potassium salts, magnesium salts, calcium salts and aluminum salts. Acid salts of the compounds represented by the general formula (1) include hydrochlorides, hydrobromides, acetates, trifluoroacetates, methanesulfonates, citrates and tartarates.

The halogen atom in the general formula (1) may be fluorine, chlorine, bromine or iodine. The lower alkyl group as in the "lower alkyl group having 1 to 4 carbon atoms," the "lower alkoxy group having 1 to 4 carbon atoms," the "lower alkylthio group having 1 to 4 carbon atoms," the "lower alkyl group sulfinyl having 1 to 4 carbon atoms," the "lower alkyl sulfonyl group having 1 to 4 carbon atoms" or the "lower alkoxymethyl group having 1 to 4 carbon atoms" in the general formula (1) is a straight-chained or branched hydrocarbon having 1 to 4 carbon atoms, including methyl, ethyl, propyl, isopropyl, butyl and t-butyl. The "substituted or unsubstituted phenoxy group" or "substituted or unsubstituted aralkyl group" in the general formula (1) is a phenoxy or aralkyl group that has at some position on its benzene ring a halogen atom, such as a fluorine atom, a chlorine atom, a bromine atom and an iodine atom, a trifluromethyl group, a lower alkyl group having 1 to 4 carbon atoms or a lower alkoxy group having 1 to 4 carbon atoms. The "aralkyl group" as in "aralkyl group" or "aralkyloxy group" in the general formula (1) may be a benzyl group, a diphenylmethyl group, a phenethyl group or a phenylpropyl group.

Of the compounds represented by the general formula (1) according to the present invention, those in which Y is —CH$_2$O— and R5 is a lower alkyl group having 1 to 4 carbon atoms, which are represented by the following general formula (1c):

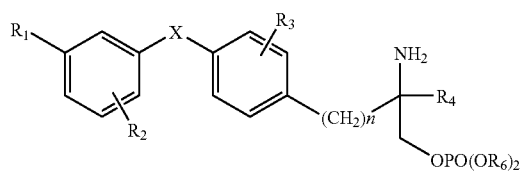

(wherein R$_6$ is a lower alkyl group having 1 to 4 carbon atoms; and R$_1$, R$_2$, R$_3$, R$_4$, X and n are as defined above) can be produced through the following pathway:

Synthetic pathway 1

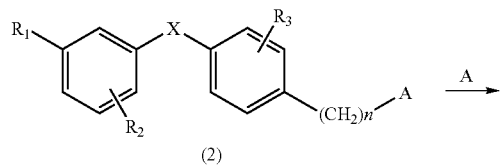

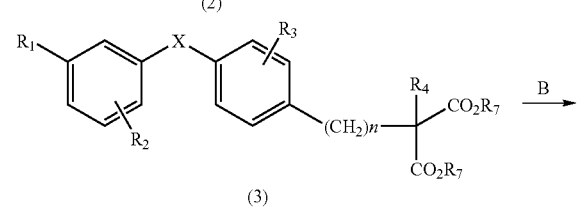

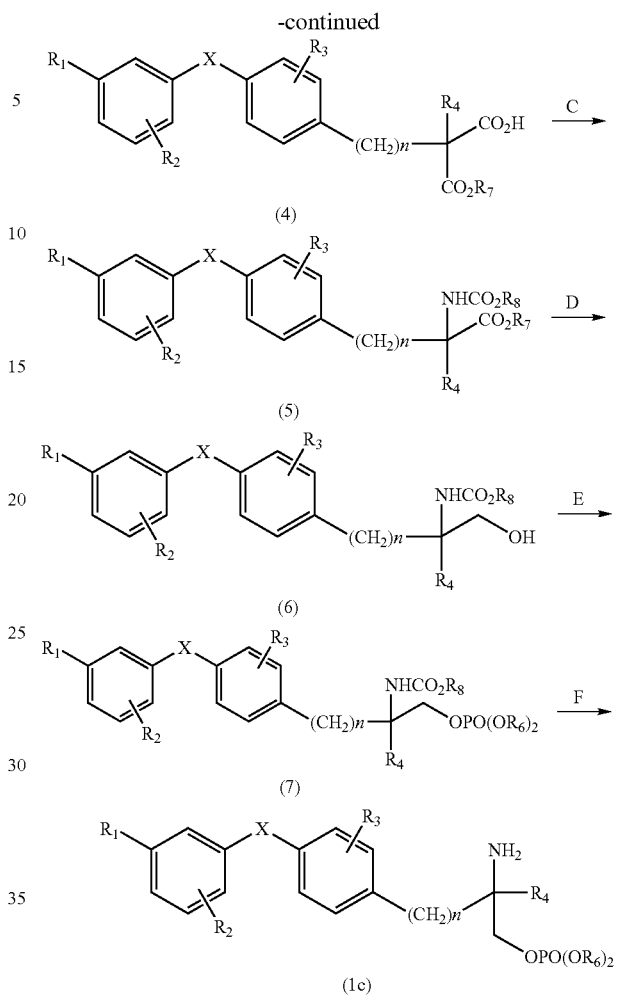

In the synthetic pathway 1, the compound represented by the following general formula (3):

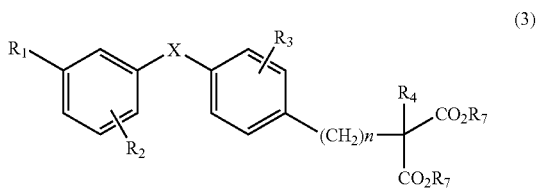

(wherein R$_7$ is a lower alkyl group having 1 to 4 carbon atoms; and R$_1$, R$_2$, R$_3$, R$_4$, X and n are as defined above) can be obtained by reacting a compound represented by the following general formula (2):

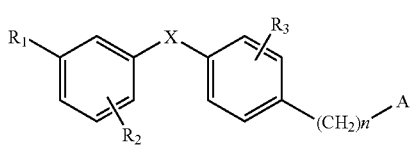

(wherein A is a chlorine atom, a bromine atom or an iodine atom; and $R_1$, $R_2$, $R_3$, X and n are as defined above) with a compound represented by the following general formula (8):

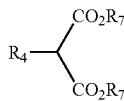

(8)

(wherein $R_4$ and $R_7$ are as defined above) in the presence of a base (Step A).

This reaction may use methanol, ethanol, 1,4-dioxane, dimethylsulfoxide (DMSO), N,N-dimethylformamide (DMF) or tetrahydrofurane (THF) as a reaction solvent and may be carried out at a reaction temperature of 0° C. to reflux temperature, preferably 80° C. to 100° C., and in the presence of an inorganic base such as sodium hydride, potassium hydride, sodium alkoxide, potassium alkoxide, potassium carbonate and sodium carbonate.

In the synthetic pathway 1, the compound represented by the following general formula (4):

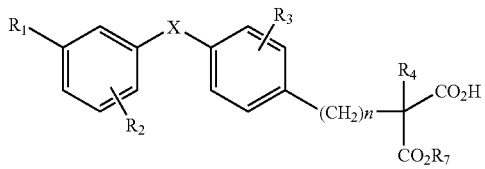

(4)

(wherein $R_1$, $R_2$, $R_3$, $R_4$, $R_7$, X and n are as defined above) can be obtained by hydrolysis of the compound of the general formula (3) (Step B).

This reaction may use methanol, ethanol, 1,4-dioxane, DMF or DMSO as a reaction solvent and may be carried out at a reaction temperature of 0° C. to reflux temperature and in the presence of a base, such as aqueous solution of sodium hydroxide, potassium hydroxide or lithium hydroxide. Preferably, the compound of the general formula (3) is reacted with potassium hydroxide in an ethanol solvent at 50° C.

In the synthetic pathway 1, the compound represented by the following general formula (5):

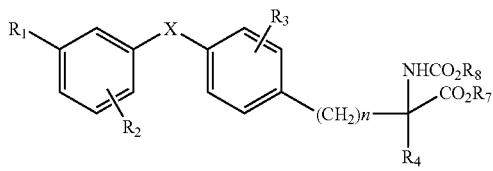

(5)

(wherein $R_8$ is a lower alkyl group having 1 to 4 carbon atoms; and $R_1$, $R_2$, $R_3$, $R_4$, $R_7$, X and n are as defined above) can be obtained by allowing the compound of the general formula (4) to undergo Curtis rearrangement (Step C).

This reaction can be carried out by using common techniques for converting a carboxyl group into a carbamate. One such technique involves the use of ethyl chlorocarbonate and $NaN_3$. Another preferred technique involves heating diphenylphosphoryl azide (DPPA) in a benzene or toluene solvent in the presence of a base such as triethylamine while stirring the mixture, followed by addition of a lower alcohol such as methanol, ethanol, propanol, isopropanol, butanol and t-butanol and then further heating while stirring the mixture. Alternatively, the reaction may use only a lower alcohol as a reaction solvent and is carried out by heating and stirring the mixture and, preferably, by heat-refluxing the mixture.

In the synthetic pathway 1, the compound represented by the following general formula (6):

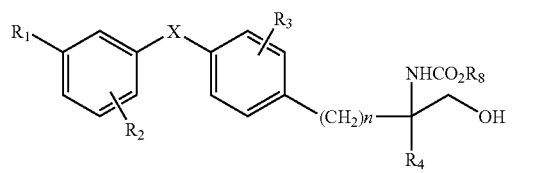

(6)

(wherein $R_1$, $R_2$, $R_3$, $R_4$, $R_8$, X and n are as defined above) can be obtained by the reduction of the compound of the general formula (5) (Step D).

This reaction may use an alkylborane derivative such as borane ($BH_3$) and 9-borabicyclo[3.3.1]nonane(9-BBN) and a metal hydride complex such as diisobutylaluminum hydride (($iBu)_2AlH$), sodium borohydride ($NaBH_4$) and lithium aluminum hydride ($LiAlH_4$), preferably lithium borohydride ($LiBH_4$), and uses THF, 1,4-dioxane, ethanol or methanol as a reaction solvent. The reaction may typically be carried out at a reaction temperature of 0° C. to reflux temperature, preferably at room temperature.

In the synthetic pathway 1, the compound represented by the following general formula (7):

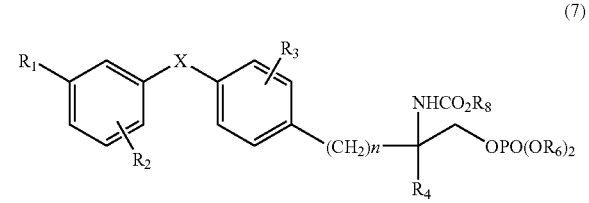

(7)

(wherein $R_1$, $R_2$, $R_3$, $R_4$, $R_6$, $R_8$, X and n are as defined above) can be obtained by reacting the compound of the general formula (6) with a compound represented by the following general formula (9):

(9)

(wherein $R_6$ is as described above) (Step E).

This reaction may be carried out without any solvent or by using methylene chloride, chloroform, acetonitrile, ethyl acetate, THF or ether as a dilution solvent and may be carried out at a reaction temperature of 0° C. to room temperature and in the presence of carbon tetrabromide and pyridine.

In the synthetic pathway 1, the compound of the general formula (1c) can be obtained by acidolysis or hydrolysis of the compound of the general formula (7) (Step F).

This reaction may be carried out in an inorganic acid or organic acid such as acetic acid, hydrochloric acid, hydrobromic acid, methanesulfonic acid and trifluoroacetic acid or in a mixture with an organic solvent such as methanol, ethanol, THF, 1,4-dioxane and ethyl acetate and may be carried out at a reaction temperature of 0° C. to room temperature. Alternatively, the reaction may use methanol, ethanol, 1,4-dioxane, DMSO, DMF or THF as a reaction solvent and may be carried out at a reaction temperature of 0° C. to reflux temperature, preferably 80° C. to 100° C., and in the presence of a base such as an aqueous solution of sodium hydroxide, potassium hydroxide or lithium hydroxide.

Of the compounds represented by the general formula (1), those in which $R_4$ is a hydrogen atom or a hydroxymethyl group, $R_5$ is a lower alkyl group having 1 to 4 carbon atoms and Y is —CH$_2$O— and which are represented by the following general formula (1d):

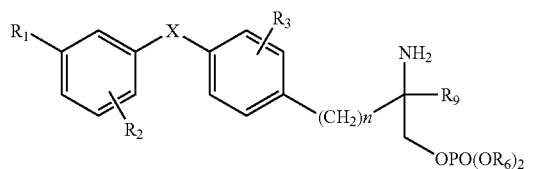
(1d)

(wherein $R_9$ is a hydrogen atom or a hydroxymethyl group; and $R_1$, $R_2$, $R_3$, $R_6$, X and n are as defined above) can be produced through the following pathway:

Synthetic pathway 2

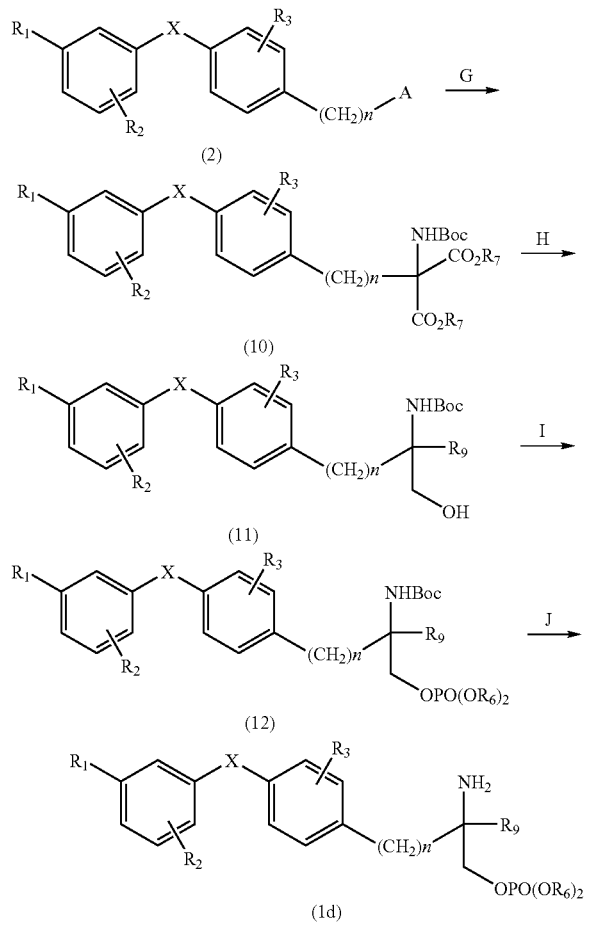

In the synthetic pathway 2, the compound represented by the following general formula (10):

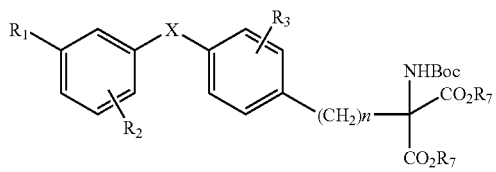
(10)

(wherein Boc is t-butoxycarbonyl group; and $R_1$, $R_2$, $R_3$, $R_7$, X and n are as defined above) can be obtained by reacting the compound of the general formula (2) with a compound represented by the following general formula (13):

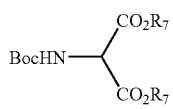
(13)

(wherein $R_7$ and Boc are as defined above) in the presence of a base (Step G).

This reaction may use methanol, ethanol, 1,4-dioxane, DMSO, DMF or THF as a reaction solvent and may be carried out at a reaction temperature of 0° C. to reflux temperature, preferably 80° C. to 100° C., and in the presence of an inorganic base such as sodium hydride, potassium hydride, sodium alkoxide, potassium alkoxide, potassium carbonate and sodium carbonate.

In the synthetic pathway 2, the compound represented by the following general formula (11):

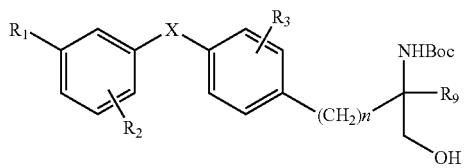
(11)

(wherein $R_1$, $R_2$, $R_3$, $R_9$, X, Boc and n are as defined above) can be obtained by reduction of the compound of the general formula (10) (Step H).

This reaction may use an alkylborane derivative such as BH$_3$ and 9-BBN and a metal hydride complex such as (iBu)$_2$AlH, NaBH$_4$ and LiAlH$_4$, preferably LiBH$_4$, and uses THF, 1,4-dioxane, ethanol or methanol as a reaction solvent. The reaction may be carried out at a reaction temperature of 0° C. to reflux temperature, preferably at room temperature.

In the synthetic pathway 2, the compound represented by the following general formula (12):

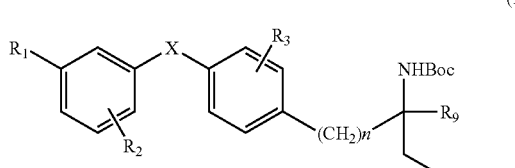
(12)

(wherein $R_1$, $R_2$, $R_3$, $R_6$, $R_9$, X, Boc and n are as defined above) can be obtained by reacting the compound of the general formula (11) with a compound represented by the following general formula (9):

P(OR$_6$)$_3$ (9)

(wherein $R_6$ is as described above) (Step I).

This reaction may be carried out without any solvent or by using methylene chloride, chloroform, acetonitrile, ethyl acetate, THF or ether as a solvent and may be carried out at a reaction temperature of 0° C. to room temperature and in the presence of carbon tetrabromide and pyridine.

In the synthetic pathway 2, the compound of the general formula (1d) can be obtained by acidolysis of the compound of the general formula (12) (Step J).

This reaction may be carried out in an inorganic acid or organic acid such as acetic acid, hydrochloric acid, hydrobromic acid, methanesulfonic acid and trifluoroacetic acid or in a mixture with an organic solvent such as methanol, ethanol, THF, 1,4-dioxane and ethyl acetate and may be carried out at a reaction temperature of 0° C. to room temperature.

Of the compounds represented by the general formula (1), those in which Y is —CH=CH— or —CH$_2$—CH$_2$— and R$_5$ is a lower alkyl group, which are represented by the following general formula (1e):

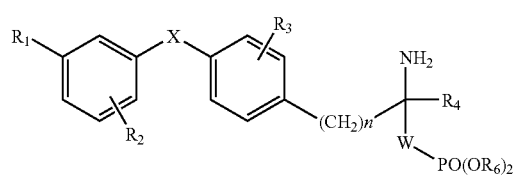

(1e)

(wherein W is —CH=CH— or —CH$_2$—CH$_2$—; and R$_1$, R$_2$, R$_3$, R$_4$, R$_6$, X and n are as defined above) can be produced through the following synthetic pathway 3:

In the synthetic pathway 3, the compound represented by the following general formula (14):

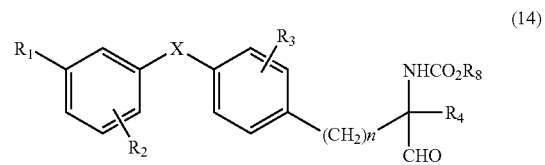

(14)

(wherein R$_1$, R$_2$, R$_3$, R$_4$, R$_8$, X and n are as defined above) can be obtained by oxidation of the compound of the general formula (6) (Step K).

This reaction may be carried out using a common technique for oxidizing alcohol into aldehyde. Among agents used in these techniques are chromium oxide/pyridine complexes, such as pyridinium chlorochromate and pyridinium dichromate, and metal oxidizing agents, such as chromium oxide, silver carbonate and manganese dioxide. DMSO oxidation using DMSO activating agents, such as oxalyl chloride, anhydrous trifluoroacetic acid, anhydrous acetic acid, DCC and sulfur trioxide/pyridine complex, may also be employed.

In the synthetic pathway 3, the compound represented by the following general formula (15):

Synthetic pathway 3

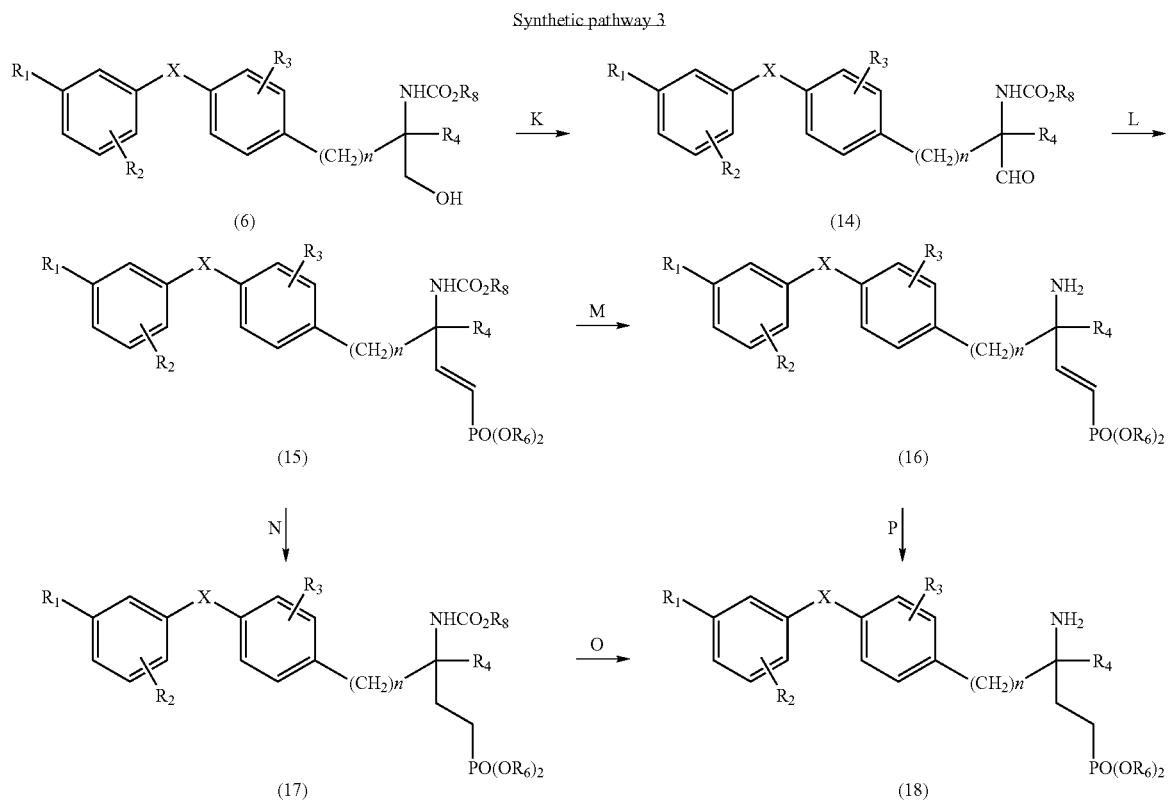

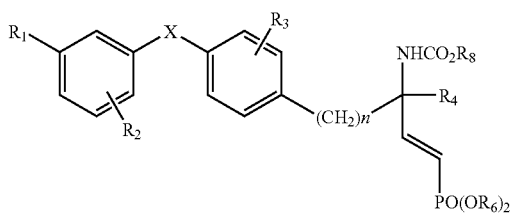

(15)

(wherein $R_1$, $R_2$, $R_3$, $R_4$, $R_6$, $R_8$, X and n are as defined above) can be obtained by reacting the compound of the general formula (14) with a compound represented by the following general formula (19):

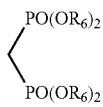

(19)

(wherein $R_6$ are as defined above) in the presence of a base (Step L).

This reaction may use THF, ether or 1,4-dioxane as a reaction solvent and can be carried out at a reaction temperature of −78° C. to room temperature and in the presence of sodium hydride, potassium hydride, sodium alkoxide or potassium alkoxide, preferably n-butyllithium.

In the synthetic pathway 3, the compound represented by the following general formula (16):

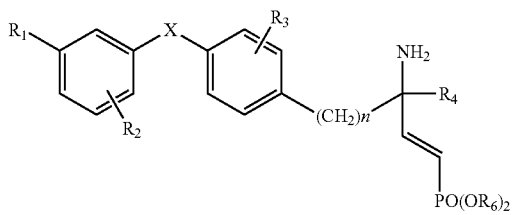

(16)

(wherein $R_1$, $R_2$, $R_3$, $R_4$, $R_6$, X and n are as defined above) can be obtained by acidolysis or hydrolysis of the compound of the general formula (15) (Step M).

This reaction may be carried out in an inorganic acid or organic acid such as acetic acid, hydrochloric acid, hydrobromic acid, methanesulfonic acid and trifluoroacetic acid or in a mixture with an organic solvent such as methanol, ethanol, THF, 1,4-dioxane and ethyl acetate and is preferably carried out at a reaction temperature of 0° C. to room temperature. Alternatively, the reaction may use methanol, ethanol, 1,4-dioxane, DMSO, DMF or THF as a reaction solvent and may be carried out at a reaction temperature of 0° C. to reflux temperature, preferably 80° C. to 100° C., and in the presence of a base such as an aqueous solution of sodium hydroxide, potassium hydroxide or lithium hydroxide.

In the synthetic pathway 3, the compound represented by the following general formula (17):

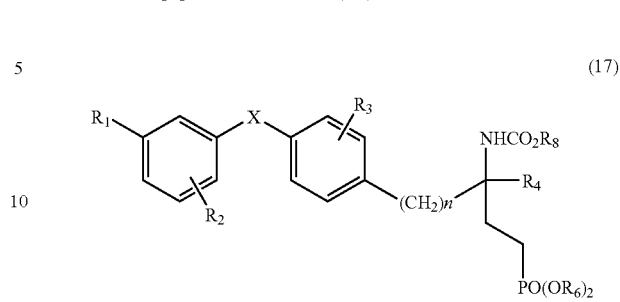

(17)

(wherein $R_1$, $R_2$, $R_3$, $R_4$, $R_6$, $R_8$, X and n are as defined above) can be obtained by reduction of the compound of the general formula (15) (Step N).

This reaction can be carried out in the presence of a reduction catalyst, such as palladium carbon, platinum carbon, platinum oxide, rhodium carbon and ruthenium carbon, and in such a solvent as ethanol, methanol, THF, DMF and ethyl acetate and is carried out at room temperature under a hydrogen pressure of atmospheric or higher pressure.

In the synthetic pathway 3, the compound represented by the following general formula (18):

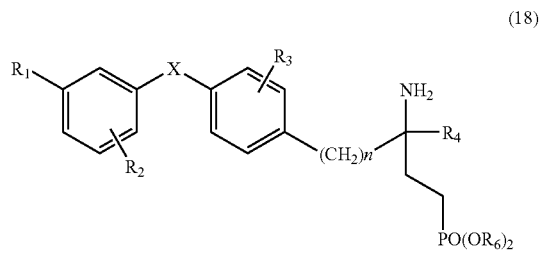

(18)

(wherein $R_1$, $R_2$, $R_3$, $R_4$, $R_6$, X and n are as defined above) can be obtained by acidolysis or hydrolysis of the compound of the general formula (17) (Step O).

This reaction may be carried out in an inorganic acid or organic acid such as acetic acid, hydrochloric acid, hydrobromic acid, methanesulfonic acid and trifluoroacetic acid or in a mixture with an organic solvent such as methanol, ethanol, THF, 1,4-dioxane and ethyl acetate and may be carried out at a reaction temperature of 0° C. to room temperature. Alternatively, the reaction may use methanol, ethanol, 1,4-dioxane, DMSO, DMF or THF as a reaction solvent and may be carried out at a reaction temperature of 0° C. to reflux temperature, preferably 80° C. to 100° C., and in the presence of a base such as an aqueous solution of sodium hydroxide, potassium hydroxide or lithium hydroxide.

The compound of the general formula (18) can also be obtained by reduction of the compound of the general formula (16) (Step P). In such a case, the reaction may be carried out in the presence of a reduction catalyst, such as palladium carbon, platinum carbon, platinum oxide, rhodium carbon and ruthenium carbon, and in such a solvent as ethanol, methanol, THF, DMF and ethyl acetate and may be carried out under a hydrogen pressure of atmospheric or higher pressure at room temperature.

Of the compounds represented by the general formula (1), those in which Y is —CH=CF— or —CH$_2$CHF— and $R_5$ is a lower alkyl group having 1 to 4 carbon atoms, which are represented by the following general formula (1f):

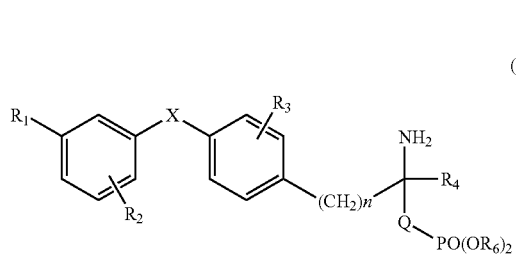

(1f)

(wherein Q is —CH=CF— or —CH$_2$CHF—; and $R_1$, $R_2$, $R_3$, $R_4$, $R_6$, X and n are as defined above) can be produced through the following synthetic pathway 4:

In the synthetic pathway 4, the compound represented by the following general formula (20):

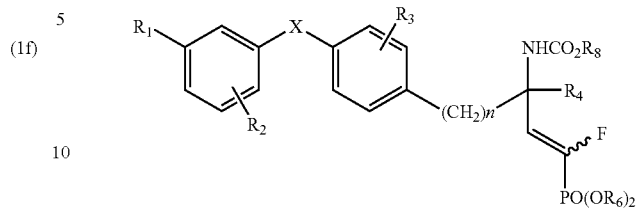

(20)

(wherein $R_1$, $R_2$, $R_3$, $R_4$, $R_6$, $R_8$, X and n are as defined above) can be obtained by reacting the compound of the general formula (14) with the compound represented by the following general formula (24):

FBr$_2$CPO(OR$_6$)$_2$ (24)

Synthetic pathway 4

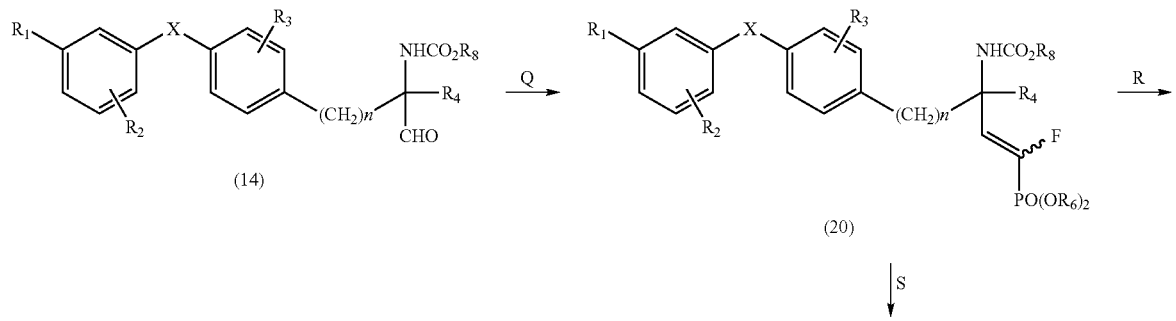

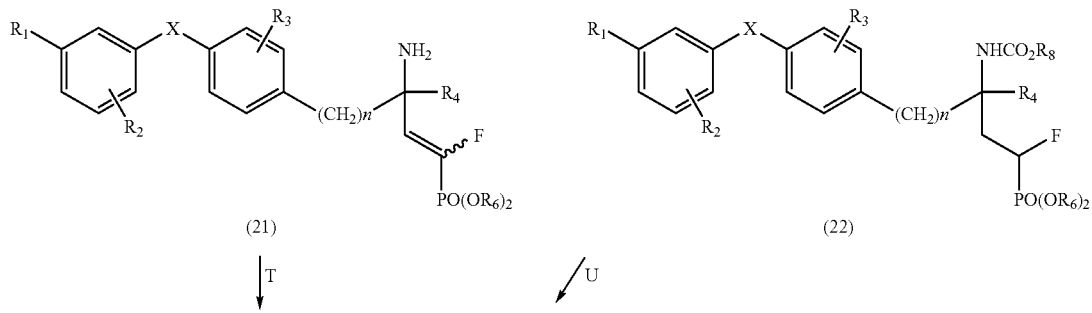

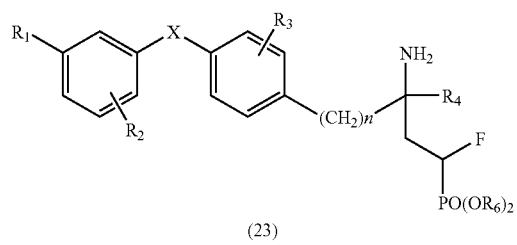

(wherein $R_6$ is as defined above) in the presence of chlorotrimethylsilane (Step Q).

This reaction may use n-butyllithium or lithium diisopropylamide as a base and 1,4-dioxane, ether or, preferably, THF as a solvent and may be carried out at −78° C. to 0° C.

In the synthetic pathway 4, the compound represented by the following general formula (21):

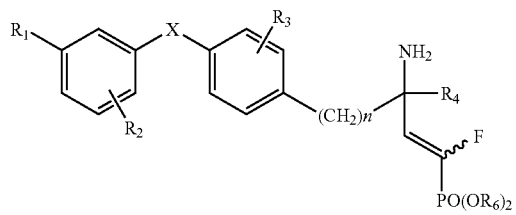

(21)

(wherein $R_1, R_2, R_3, R_4, R_6$, X and n are as defined above) can be obtained by acidolysis or hydrolysis of the compound of the general formula (20) (Step R).

This reaction may be carried out in an inorganic acid or organic acid such as acetic acid, hydrochloric acid, hydrobromic acid, methanesulfonic acid and trifluoroacetic acid or in a mixture with an organic solvent such as methanol, ethanol, THF, 1,4-dioxane and ethyl acetate and may be carried out at a reaction temperature of 0° C. to room temperature. Alternatively, the reaction may use methanol, ethanol, 1,4-dioxane, DMSO, DMF or THF as a reaction solvent and may be carried out at a reaction temperature of 0° C. to reflux temperature, preferably 80° C. to 100° C., and in the presence of a base such as an aqueous solution of sodium hydroxide, potassium hydroxide or lithium hydroxide.

In the synthetic pathway 4, the compound represented by the following general formula (22):

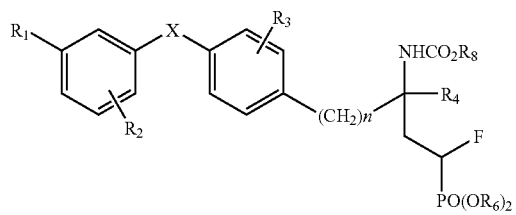

(22)

(wherein $R_1, R_2, R_3, R_4, R_6, R_8$, X and n are as defined above) can be obtained by reduction of the compound of the general formula (20) (Step S).

This reaction can be carried out in the presence of a reduction catalyst, such as palladium carbon, platinum carbon, platinum oxide, rhodium carbon and ruthenium carbon, and in such a solvent as ethanol, methanol, THF, DMF and ethyl acetate and may be carried out at room temperature under a hydrogen pressure of atmospheric or higher pressure.

In the synthetic pathway 4, the compound represented by the following general formula (23):

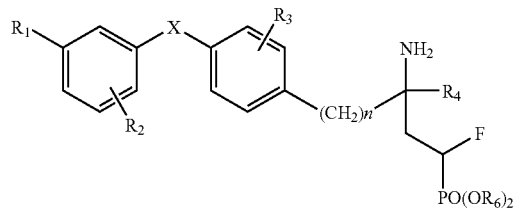

(23)

(wherein $R_1, R_2, R_3, R_4, R_6$, X and n are as defined above) can be obtained by reduction of the compound of the general formula (21) (Step T) or acidolysis or hydrolysis of the compound of the general formula (22) (Step U).

This reduction process can be carried out in the presence of a reduction catalyst, such as palladium carbon, platinum carbon, platinum oxide, rhodium carbon and ruthenium carbon, and in such a solvent as ethanol, methanol, THF, DMF and ethyl acetate and may be carried out at room temperature under a hydrogen pressure of atmospheric or higher pressure. The acidolysis or hydrolysis process may be carried out in an inorganic acid or organic acid such as acetic acid, hydrochloric acid, hydrobromic acid, methanesulfonic acid and trifluoroacetic acid or in a mixture with an organic solvent such as methanol, ethanol, THF, 1,4-dioxane and ethyl acetate and may be carried out at a reaction temperature of 0° C. to room temperature. Alternatively, the reaction may use methanol, ethanol, 1,4-dioxane, DMSO, DMF or THF as a reaction solvent and may be carried out at a reaction temperature of 0° C. to reflux temperature, preferably 80° C. to 100° C., and in the presence of a base such as an aqueous solution of sodium hydroxide, potassium hydroxide or lithium hydroxide.

Of the compounds represented by the general formula (1), those in which $R_5$ is a lower alkyl group having 1 to 4 carbon atoms and Y is —$CH_2$—, —$CH_2CH_2$—, —$CH_2CHF$— or —$CH_2CF_2$—, which are represented by the following general formula (1g):

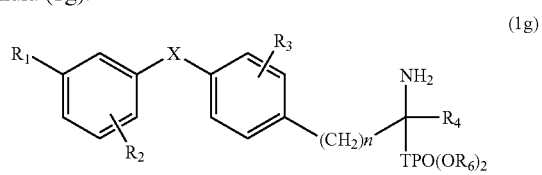

(1g)

(wherein T is —$CH_2$—, —$CH_2CH_2$—, —$CH_2CHF$— or —$CH_2CF_2$—; and $R_1, R_2, R_3, R_4, R_6$, X and n are as defined above) can be produced through the following synthetic pathway 5:

Synthetic pathway 5

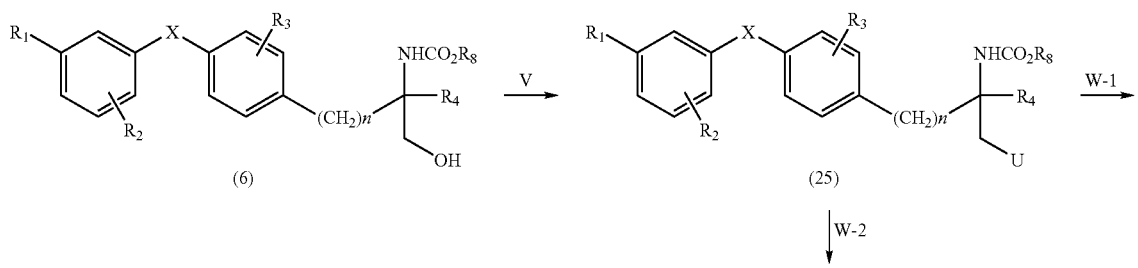

-continued

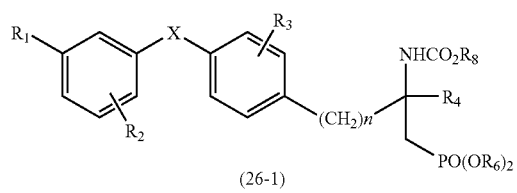
(26-1)

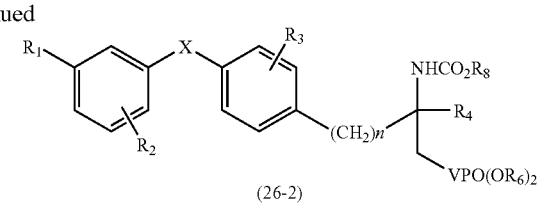
(26-2)

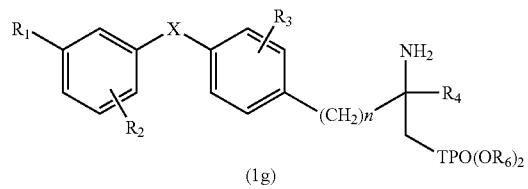
(1g)

In the synthetic pathway 5, the compound represented by the following general formula (25):

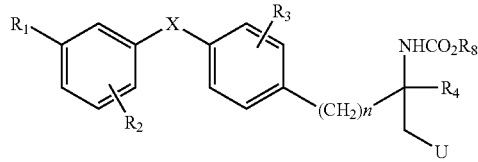
(25)

(wherein U is an iodine atom, a bromine atom, a methanesulfonyloxy group or a trifluoromethanesulfonyloxy group; and $R_1$, $R_2$, $R_3$, $R_4$, $R_8$, X and n are as defined above) can be produced from the compound of the general formula (6) (Step V).

For the introduction of methanesulfonyloxy group or trifluoromethanesulfonyloxy group, an organic solvent such as methylene chloride, chloroform, ethyl acetate and THF is used along with a base such as triethylamine, diisopropylethylamine, pyridine, lutidine and 2,4,6-trimethylpyridine, and the compound of the general formula (6) is preferably reacted with methanesulfonyl chloride or anhydrous trifluoromethanesulfonate at −45° C. to room temperature.

The brominated or iodized compound is synthesized by reacting the methanesulfonyloxylated product obtained in the above process with sodium bromide, sodium iodide, potassium bromide, potassium iodide, lithium bromide or lithium iodide at room temperature to reflux temperature in a solvent such as toluene, benzene or THF.

In the synthetic pathway 5, the compound represented by the following general formula (26-1):

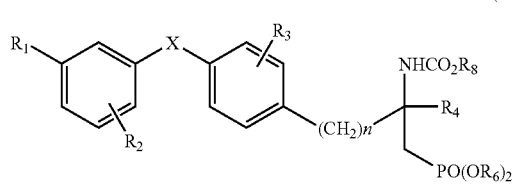
(26-1)

(wherein $R_1$, $R_2$, $R_3$, $R_4$, $R_6$, $R_8$, X and n are as defined above) can be obtained by reacting the compound of the general formula (25) with a compound represented by the following general formula (27):

$$PO(OR_6)_3 \tag{27}$$

(wherein $R_6$ is as defined above) (Step W-1)

This reaction is preferably carried out in the absence of solvent and using the compound of the general formula (27) as a solvent and is preferably carried out at 100 to 150° C. or at reflux temperature.

In the synthetic pathway 5, the compound represented by the following general formula (26-2):

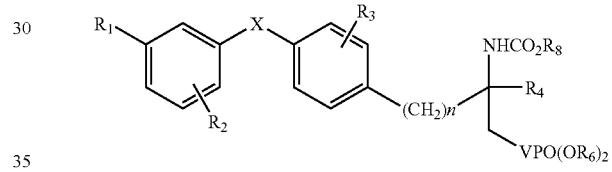
(26-2)

(wherein V is a fluorinated or unfluorinated methylene group; and $R_1$, $R_2$, $R_3$, $R_4$, $R_6$, $R_8$, X and n are as defined above) can be obtained by reacting the compound of the general formula (25) with a compound represented by the following general formula (28):

$$HVPO(OR_6)_2 \tag{28}$$

(wherein $R_6$ and V are as defined above) in the presence of a base (Step W-2).

This reaction may be carried out in the presence of such a base as lithium diisopropylamide, lithium hexamethyldisilazide and lithium tetramethylpiperidide in such a reaction solvent as THF and 1,4-dioxane and may be carried out at a reaction temperature of −78° C. to room temperature.

In the synthetic pathway 5, the compound of the general formula (1 g) can be obtained by acidolysis or hydrolysis of the compound of the general formula (26-1) or (26-2) (Step X).

This reaction may be carried out in an inorganic acid or organic acid such as acetic acid, hydrochloric acid, hydrobromic acid, methanesulfonic acid and trifluoroacetic acid or in a mixture with an organic solvent such as methanol, ethanol, THF, 1,4-dioxane and ethyl acetate and may be carried out at a reaction temperature of 0° C. to room temperature. Alternatively, the reaction may use methanol, ethanol, 1,4-dioxane, DMSO, DMF or THF as a reaction solvent and may be carried out at a reaction temperature of 0° C. to reflux temperature, preferably 80° C. to 100° C., and in the presence of a base such as an aqueous solution of sodium hydroxide, potassium hydroxide or lithium hydroxide.

Of the compounds represented by the general formula (1), those in which $R_5$ is a lower alkyl group having 1 to 4 carbon atoms and Y is —CH(OH)CF$_2$— and which are represented by the following general formula (1h):

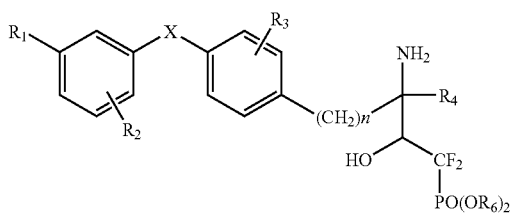

(1h)

(wherein R$_1$, R$_2$, R$_3$, R$_4$, R$_6$, X and n are as defined above) can be synthesized through the following synthetic pathway 6:

Synthetic pathway 6

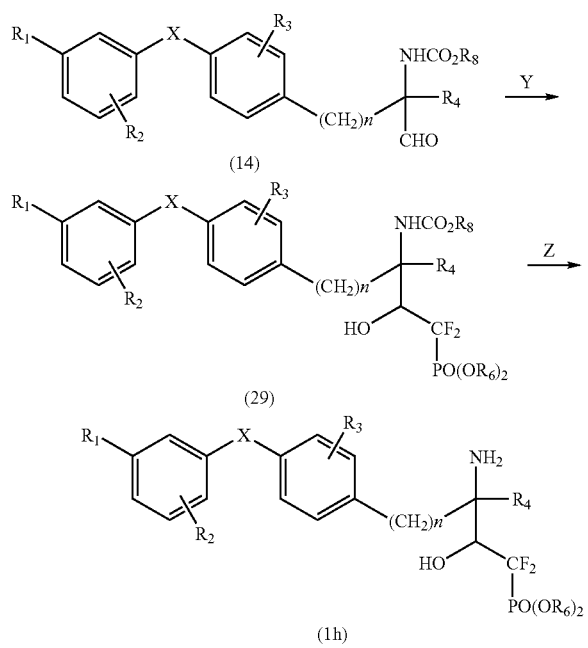

In the synthetic pathway 6, the compound represented by the following general formula (29):

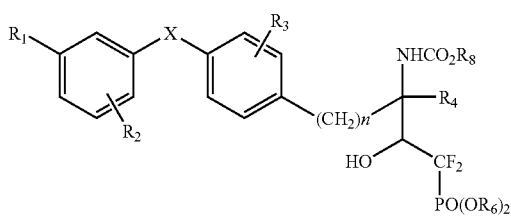

(29)

(wherein R$_1$, R$_2$, R$_3$, R$_4$, R$_6$, R$_8$, X and n are as defined above) can be obtained by reacting the compound of the general formula (14) with a compound represented by the following general formula (30):

HCF$_2$PO(OR$_6$)$_2$ (30)

(wherein R$_6$ is as defined above) in the presence of a base (Step Y).

This reaction may use n-butyllithium, preferably lithium diisopropylamide, as a base and 1,4-dioxane or ether, preferably THF, as a solvent and may be carried out at −78° C. to 0° C.

In the synthetic pathway 6, the compound of the general formula (1h) can be obtained by acidolysis or hydrolysis of the compound of the general formula (29) (Step Z).

This reaction may be carried out in an inorganic acid or organic acid such as acetic acid, hydrochloric acid, hydrobromic acid, methanesulfonic acid and trifluoroacetic acid or in a mixture with an organic solvent such as methanol, ethanol, THF, 1,4-dioxane and ethyl acetate and may be carried out at a reaction temperature of 0° C. to room temperature. Alternatively, the reaction may use methanol, ethanol, 1,4-dioxane, DMSO, DMF or THF as a reaction solvent and may be carried out at a reaction temperature of 0° C. to reflux temperature, preferably 80° C. to 100° C., and in the presence of a base such as an aqueous solution of sodium hydroxide, potassium hydroxide or lithium hydroxide.

Of the compounds represented by the general formula (1), those in which R$_5$ is hydrogen and which are represented by the following general formula (1i):

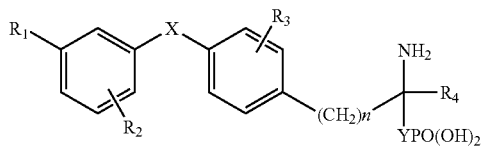

(1i)

(wherein R$_1$, R$_2$, R$_3$, R$_4$, X, Y and n are as defined above) can be obtained by acidolysis or treatment with trimethylsilyl bromide or trimethylsilyl iodide of the compound represented by the following general formula (31):

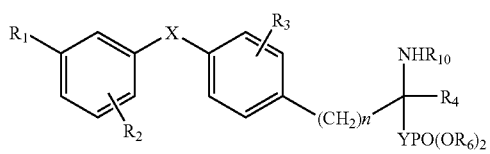

(31)

(wherein R$_{10}$ is a hydrogen atom or a lower alkoxycarbonyl group having 1 to 4 carbon atoms; and R$_1$, R$_2$, R$_3$, R$_4$, R$_6$, X, Y and n are as defined above).

The acidolysis process is preferably carried out in an inorganic acid such as hydrochloric acid and hydrobromic acid or in a mixture with an organic acid such as methanol and ethanol and is preferably carried out at reflux temperature.

Alternatively, the reaction may use acetonitrile or methylene chloride as a solvent and the compound of the general formula (31) may be treated with trimethylsilyl bromide or trimethylsilyl iodide, or the combination of trimethylsilyl chloride and sodium bromide or sodium iodide. In such a case, the reaction is preferably carried out at 0° C. to room temperature.

The compounds of the respective general formulae in which X is SO or SO$_2$ may also be obtained by oxidation of the corresponding compounds in which X is S.

Such a reaction may use 1,4-dioxane, DMSO, DMF, THF, methylene chloride or chloroform as a reaction solvent and potassium permanganate, m-chlorobenzoic acid or aqueous hydrogen peroxide as an oxidizing agent and is preferably carried out at 0° C. to reflux temperature, preferably at room temperature.

EXAMPLES

The present invention will now be described with reference to specific examples, which are not intended to limit the scope of the invention in any way.

Reference Example 1

2-chloro-4-[(3-trifluoromethyl)phenylthio]benzaldehyde

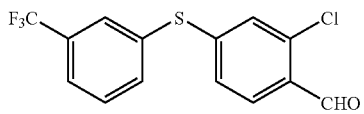

To a DMF solution (20 mL) of 2-chloro-4-fluorobenzaldehyde(1.15 g) and 3-(trifluoromethyl)thiophenol(1.33 g), potassium carbonate (2.76 g) was added and the mixture was stirred for 1 hour at, 120° C. Subsequently, the reaction mixture was poured into water and was extracted with ethyl acetate. The extract was washed sequentially with water and a saturated aqueous solution of sodium chloride and the organic phase was dried over anhydrous sodium sulfate. The solvent was removed under reduced pressure and the resulting residue was purified on a silica gel column chromatography (hexane:ethyl acetate=10:1). This gave the desired product as a pale yellow oil (1.96 g).

Reference Examples 2 through 57

In a similar manner to Reference Example 1, different thiophenols and phenols were used to synthesize the different compounds shown in Table 1 below.

TABLE 1

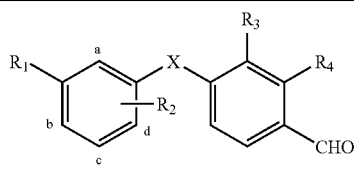

| Reference Examples | R1 | R2 | R3 | R4 | X |
|---|---|---|---|---|---|
| 2 | Cl | c-Cl | H | Cl | O |
| 3 | t-Bu | H | H | H | O |
| 4 | Me | H | H | H | O |
| 5 | i-Pr | c-i-Pr | H | Cl | O |
| 6 | $C_5H_{11}$ | H | H | H | O |
| 7 | $C_7H_{15}$ | H | H | H | O |
| 8 | $CF_3$ | H | H | H | O |
| 9 | $CF_3$ | H | OMe | H | O |
| 10 | $CF_3$ | H | H | OMe | O |
| 11 | $CF_3$ | H | H | $OCH_2Ph$ | O |
| 12 | $CF_3$ | H | $CF_3$ | H | O |
| 13 | $CF_3$ | H | H | $CF_3$ | O |
| 14 | $CF_3$ | c-$CF_3$ | H | H | O |
| 15 | $CF_3$ | c-$CF_3$ | H | Cl | O |
| 16 | $CF_3$ | b-Cl | H | H | O |
| 17 | $CF_3$ | a-Cl | H | H | O |
| 18 | $CF_3$ | d-Cl | H | H | O |
| 19 | $CF_3$ | c-MeO | H | Cl | O |
| 20 | $Ph(CH_2)_2$ | H | H | Cl | O |
| 21 | $Ph(CH_2)_2$ | H | H | $CF_3$ | O |
| 22 | $Ph(CH_2)_2$ | c-$CF_3$ | H | H | O |
| 23 | $Ph(CH_2)_2$ | c-$CF_3$ | H | Cl | O |
| 24 | $Ph(CH_2)_2$ | c-$Ph(CH_2)_2$ | H | H | O |
| 25 | $Ph(CH_2)_2$ | c-$Ph(CH_2)_2$ | H | $CF_3$ | O |
| 26 | $Ph(CH_2)_2$ | c-$Ph(CH_2)_2$ | H | Cl | O |
| 27 | $CF_3$ | c-$NO_2$ | H | H | O |
| 28 | $CF_3$ | H | Cl | H | O |
| 29 | $CF_3$ | H | H | Cl | O |
| 30 | i-PrO | c-iPr | H | Cl | O |

TABLE 1-continued

| Reference Examples | R1 | R2 | R3 | R4 | X |
|---|---|---|---|---|---|
| 31 | i-PrO | c-iPr | H | H | O |
| 32 | PhO | H | H | Cl | O |
| 33 | $PhCH_2O$ | H | H | H | O |
| 34 | $PhCH_2O$ | H | H | Br | O |
| 35 | $PhCH_2O$ | H | H | SMe | O |
| 36 | $PhCH_2O$ | H | H | Me | O |
| 37 | $PhCH_2O$ | H | H | Et | O |
| 38 | $PhCH_2O$ | c-Cl | H | Cl | O |
| 39 | $PhCH_2O$ | H | H | $CF_3$ | O |
| 40 | $PhCH_2O$ | H | H | Ph | O |
| 41 | $PhCH_2O$ | c-$PhCH_2O$ | H | Cl | O |
| 42 | $PhCH_2O$ | c-$PhCH_2O$ | H | H | O |
| 43 | $PHCH_2O$ | c-$PhCH_2O$ | H | i-Pr | O |
| 44 | MeO | c-$CF_3$ | H | H | O |
| 45 | MeS | H | H | H | O |
| 46 | $PhCH_2S$ | H | H | H | O |
| 47 | $PhCH_2S$ | H | H | Cl | O |
| 48 | Cl | c-Cl | H | H | S |
| 49 | $CF_3$ | c-$CF_3$ | H | Cl | S |
| 50 | $CF_3$ | c-$CF_3$ | H | H | S |
| 51 | $CF_3$ | H | H | H | S |
| 52 | $CF_3$ | H | H | $CF_3$ | S |
| 53 | MeO | H | H | Cl | S |
| 54 | MeO | H | H | H | S |
| 55 | MeO | H | H | $CF_3$ | S |
| 56 | $PhCH_2O$ | H | H | Cl | O |
| 57 | $PhCH_2O$ | H | H | i-Pr | O |

Reference Example 58

2-fluoro-4-[(3-trifluoromethyl)phenoxy]benzaldehyde

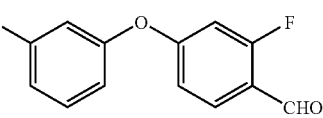

3-(trifluoromethyl)phenylboric acid (1.03 g) and 2-fluoro-4-hydroxybenzaldehyde (760 mg) were dissolved in methylene chloride (20 mL). While the mixture was stirred, copper acetate (985 mg), molecular sieve 4A (800 mg) and triethylamine (3.76 mL) were added to the mixture. An equal amount of copper acetate was added after 6 hours and after 24 hours. After 48 hours of stirring, the insoluble materials were removed by filtration and the filtrate was poured in water and was extracted with ethyl acetate. The extract was washed sequentially with water and a saturated aqueous solution of sodium chloride, and the organic phase was dried over anhydrous magnesium sulfate. The solvent was removed under reduced pressure and the resulting residue was purified on a silica gel column chromatography (hexane:ethyl acetate=7:1 then 2:1). This gave the desired product as a pale yellow oil (265 mg).

Reference Example 59

4-[(3-benzyloxy)phenoxy]-2-fluorobenzaldehyde

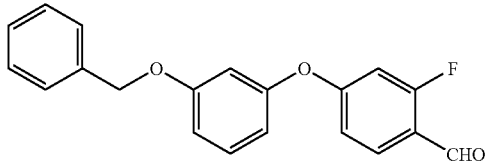

In a similar manner to Reference Example 58, 3-benzyloxyphenylboric acid and 2-fluoro-4-hydroxybenzaldehyde were used to obtain the desired product as a colorless oil.

Reference Example 60

Ethyl 2'-chloro-4'-[(3-trifluoromethyl)phenylthio]cinnamate

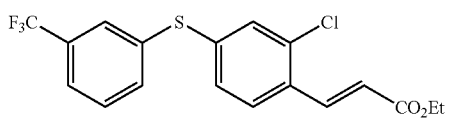

At 0° C. and under a stream of argon gas, 60% sodium hydride (272 mg) was added to a THF solution (30 mL) of ethyl diethylphosphonoacetate (1.35 mL). The mixture was stirred for 30 min and a THF solution (15 mL) of the compound of Reference Example 1 (1.96 g) was added dropwise. The mixture was stirred for 2 hours while kept at the same temperature. This was followed by addition of water and extraction with ethyl acetate. The extract was washed sequentially with water and a saturated aqueous solution of sodium chloride, and the organic phase was dried over anhydrous sodium sulfate. The solvent was removed under reduced pressure and the residue was purified on a silica gel column chromatography (hexane:ethyl acetate=10:1). This gave the desired product as a colorless oil (1.72 g).

Reference Examples 61 through 118

In a similar manner to Reference Example 60, the compounds of Reference Examples 2 through 59 were used to synthesize the compounds shown in Table 2 below.

TABLE 2

| Reference Examples | R1 | R2 | R3 | R4 | X |
|---|---|---|---|---|---|
| 61 | Cl | c-Cl | H | Cl | O |
| 62 | t-Bu | H | H | H | O |
| 63 | Me | H | H | H | O |
| 64 | i-Pr | c-i-Pr | H | Cl | O |
| 65 | $C_5H_{11}$ | H | H | H | O |
| 66 | $C_7H_{15}$ | H | H | H | O |
| 67 | $CF_3$ | H | H | H | O |
| 68 | $CF_3$ | H | OMe | H | O |
| 69 | $CF_3$ | H | H | OMe | O |
| 70 | $CF_3$ | H | H | $OCH_2Ph$ | O |
| 71 | $CF_3$ | H | $CF_3$ | H | O |
| 72 | $CF_3$ | H | H | $CF_3$ | O |
| 73 | $CF_3$ | c-$CF_3$ | H | H | O |
| 74 | $CF_3$ | c-$CF_3$ | H | Cl | O |
| 75 | $CF_3$ | b-Cl | H | H | O |
| 76 | $CF_3$ | a-Cl | H | H | O |
| 77 | $CF_3$ | d-Cl | H | H | O |
| 78 | $CF_3$ | c-MeO | H | Cl | O |
| 79 | $Ph(CH_2)_2$ | H | H | Cl | O |
| 80 | $Ph(CH_2)_2$ | H | H | $CF_3$ | O |
| 81 | $Ph(CH_2)_2$ | c-$CF_3$ | H | H | O |
| 82 | $Ph(CH_2)_2$ | c-$CF_3$ | H | Cl | O |
| 83 | $Ph(CH_2)_2$ | c-$Ph(CH_2)_2$ | H | H | O |
| 84 | $Ph(CH_2)_2$ | c-$Ph(CH_2)_2$ | H | $CF_3$ | O |
| 85 | $Ph(CH_2)_2$ | c-$Ph(CH_2)_2$ | H | Cl | O |
| 86 | $CF_3$ | H | H | F | O |
| 87 | $PhCH_2O$ | H | H | F | O |
| 88 | $CF_3$ | H | Cl | H | O |
| 89 | $CF_3$ | H | H | Cl | O |
| 90 | i-PrO | c-iPr | H | Cl | O |
| 91 | i-PrO | c-iPr | H | H | O |
| 92 | PhO | H | H | Cl | O |
| 93 | $PhCH_2O$ | H | H | H | O |
| 94 | $PhCH_2O$ | H | H | Br | O |
| 95 | $PhCH_2O$ | H | H | SMe | O |
| 96 | $PhCH_2O$ | H | H | Me | O |
| 97 | $PhCH_2O$ | H | H | Et | O |
| 98 | $PhCH_2O$ | c-Cl | H | Cl | O |
| 99 | $PhCH_2O$ | H | H | $CF_3$ | O |
| 100 | $PhCH_2O$ | H | H | Ph | O |
| 101 | $PhCH_2O$ | c-$PhCH_2O$ | H | Cl | O |
| 102 | $PhCH_2O$ | c-$PhCH_2O$ | H | H | O |
| 103 | $PhCH_2O$ | c-$PhCH_2O$ | H | i-Pr | O |
| 104 | MeO | c-$CF_3$ | H | H | O |
| 105 | MeS | H | H | H | O |
| 106 | $PhCH_2S$ | H | H | H | O |
| 107 | $PhCH_2S$ | H | H | Cl | O |
| 108 | Cl | c-Cl | H | H | S |
| 109 | $CF_3$ | c-$CF_3$ | H | Cl | S |
| 110 | $CF_3$ | c-$CF_3$ | H | H | S |
| 111 | $CF_3$ | H | H | H | S |
| 112 | $CF_3$ | H | H | $CF_3$ | S |
| 113 | MeO | H | H | Cl | S |
| 114 | MeO | H | H | H | S |
| 115 | MeO | H | H | $CF_3$ | S |
| 116 | $CF_3$ | c-$NO_2$ | H | H | O |
| 117 | $PhCH_2O$ | H | H | Cl | O |
| 118 | $PhCH_2O$ | H | H | i-Pr | O |

Reference Example 119

Methyl 4'-(3-ethylphenoxy)cinnamate

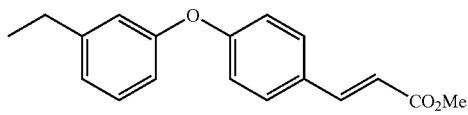

To a DMF solution (50 mL) of 3-ethylphenol (1.13 g) and methyl 4'-fluorocinnamate (834 mg), potassium carbonate (1.92 g) was added and the mixture was stirred for 8 hours at 140° C. The reaction mixture was poured into water and was extracted with ethyl acetate. The extract was washed sequentially with water and a saturated aqueous solution of sodium chloride and the organic phase was dried over anhydrous sodium sulfate. The solvent was removed under reduced pressure and the resulting residue was purified on a silica gel column chromatography (hexane:ethyl acetate=30:1). This gave the desired product as a yellow oil (540 mg).

Reference Example 120

Methyl 4'-(3-isobutylphenoxy)cinnamate

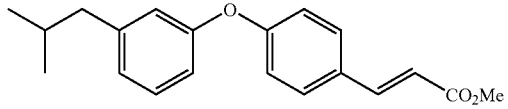

To a DMF solution (10 mL) of 3-isobutylphenol (451 mg) and methyl 4'-fluorocinnamate (541 mg), potassium carbonate (622 mg) was added and the mixture was stirred for 8 hours at 140° C. The reaction mixture was poured into water and was extracted with ethyl acetate. The extract was washed sequentially with water and a saturated aqueous solution of sodium chloride and the organic phase was dried over anhydrous sodium sulfate. The solvent was removed under reduced pressure and the resulting residue was purified on a silica gel column chromatography (hexane:ethyl acetate=30:1). This gave the desired product as a yellow oil (278 mg).

Reference Example 121

Ethyl 4'-[(3-phenoxymethyl)phenoxy]cinnamate

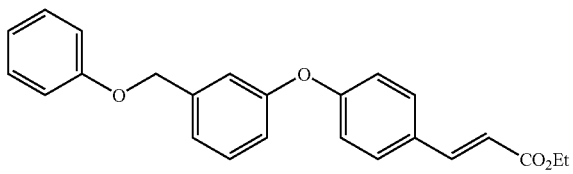

The compound of Reference Example 63 (2.82 g) was dissolved in tetrachlorocarbon (50 mL). To this solution, N-bromosuccinimide (2.31 g) was added and the mixture was stirred while heated and exposed to light. After 24 hours, the solvent was removed under reduced pressure and the resulting residue was extracted with ethyl acetate. The extract was washed sequentially with water and a saturated aqueous solution of sodium chloride and the organic phase was dried over anhydrous sodium sulfate. The solvent was removed under reduced pressure and the resulting residue was purified on a silica gel column chromatography (hexane:ethyl acetate=6:1). This gave ethyl 4'-[(3-bromomethyl)phenoxy]cinnamate as a yellow oil (1.30 g). The resultant brominated product (1.24 g) was dissolved in DMF (25 mL). To this solution, phenol (380 mg) and potassium carbonate (500 mg) were added and the mixture was stirred for 3 hours at 60° C. The reaction mixture was poured into water and was extracted with ethyl acetate. The extract was washed sequentially with water and a saturated aqueous solution of sodium chloride and the organic phase was dried over anhydrous sodium sulfate. The solvent was removed under reduced pressure and the resulting residue was purified on a silica gel column chromatography (hexane:ethyl acetate=4:1). This gave the desired product as a colorless oil (1.30 g).

Reference Example 122

Ethyl 2'-chloro-4'-(3-trifluoromethylphenylthio)dihydrocinnamate

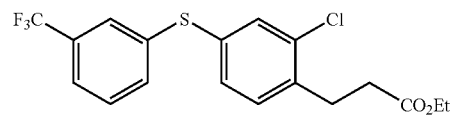

The compound of Reference Example 60 (1.72 g) was dissolved in ethanol (70 mL). While the solution was stirred at 0° C., bismuth chloride (703 mg) was added. Subsequently, sodium borohydride (673 mg) was added in small portions and the mixture was stirred for 1 hour at this temperature and 3 hours at room temperature. Ice water was added and the crystallized insoluble inorganic residue was removed by filtration through Celite. The filtrate was extracted with ethyl acetate and the extract was washed sequentially with water and a saturated aqueous solution of sodium chloride. The organic phase was then dried over anhydrous sodium sulfate. The solvent was removed under reduced pressure to give the desired product as a colorless oil (1.50 g) (Process A).

Reference Example 123

Methyl 4'-(3-ethylphenoxy)dihydrocinnamate

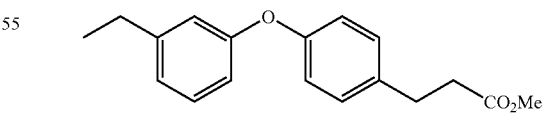

The compound of Reference Example 119 (540 mg) was dissolved in ethanol (20 mL) and 10%-Pd/C (80.0 mg) was added. Under a stream of hydrogen, the mixture was stirred at room temperature for 3 hours. The catalyst was removed by filtration and the filtrate was concentrated under reduced pressure to give the desired product as a colorless oil (Process B).

Reference Example 124

Ethyl 2'-benzyloxy-4'-[(3-trifluoromethyl)phenoxy]dihydrocinnamate

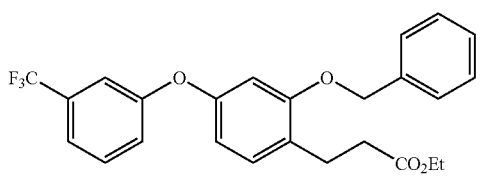

The compound of Reference Example 70 (2.29 mg) was dissolved in ethyl acetate (30 mL) and 5%-Pd/C-ethylenediamine complex (230 mg) was added. Under a stream of hydrogen, the mixture was stirred at room temperature for 3.5 hours. The catalyst was removed by filtration and the solvent was removed under reduced pressure to give the desired product as a pale yellow oil (2.30 g) (Process C).

Reference Example 125

Methyl 4'-[(3-methylthio)phenoxy]dihydrocinnamate

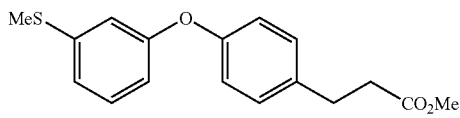

Under a stream of argon gas, the compound of Reference Example 105 (4.07 g) was dissolved in methanol (50 mL). While the solution was stirred at 10° C., magnesium (1.00 g) was added. The mixture was stirred for 3 hours while kept at this temperature, and diluted hydrochloric acid was added. The mixture was extracted with ethyl acetate and was washed sequentially with water and a saturated aqueous solution of sodium chloride. The organic phase was then dried over anhydrous sodium sulfate. The solvent was removed under reduced pressure to give the desired product as a colorless oil (3.70 g) (Process D).

Reference Examples 126 through 182

Similarly, the compounds of Reference Examples 61 through 69, 71 through 104, 106 through 116, 117 and 118, and 120 and 121 were used to synthesize the compounds shown in Table 3 below.

TABLE 3

| Reference Examples | R1 | R2 | R3 | R4 | X | Process |
|---|---|---|---|---|---|---|
| 126 | Cl | c-Cl | H | Cl | O | A |
| 127 | t-Bu | H | H | H | O | B |
| 128 | Me | H | H | H | O | B |
| 129 | i-Pr | c-i-Pr | H | Cl | O | A |
| 130 | $C_5H_{11}$ | H | H | H | O | B |
| 131 | $C_7H_{15}$ | H | H | H | O | B |
| 132 | $CF_3$ | H | H | H | O | B |
| 133 | $CF_3$ | H | OMe | H | O | B |
| 134 | $CF_3$ | H | H | OMe | O | B |
| 135 | $CF_3$ | H | $CF_3$ | H | O | B |
| 136 | $CF_3$ | H | H | $CF_3$ | O | B |
| 137 | $CF_3$ | c-$CF_3$ | H | H | O | B |
| 138 | $CF_3$ | c-$CF_3$ | H | Cl | O | B |
| 139 | $CF_3$ | b-Cl | H | H | O | A |
| 140 | $CF_3$ | a-Cl | H | H | O | A |
| 141 | CF3 | d-Cl | H | H | O | A |
| 142 | CF3 | c-MeO | H | Cl | O | B |
| 143 | $Ph(CH_2)_2$ | H | H | Cl | O | A |
| 144 | $Ph(CH_2)_2$ | H | H | $CF_3$ | O | B |
| 145 | $Ph(CH_2)_2$ | c-$CF_3$ | H | H | O | B |
| 146 | $Ph(CH_2)_2$ | c-$CF_3$ | H | Cl | O | A |
| 147 | $Ph(CH_2)_2$ | c-$Ph(CH_2)_2$ | H | H | O | B |
| 148 | $Ph(CH_2)_2$ | c-$Ph(CH_2)_2$ | H | $CF_3$ | O | B |
| 149 | $Ph(CH_2)_2$ | c-$Ph(CH_2)_2$ | H | Cl | O | A |
| 150 | $CF_3$ | H | H | F | O | B |
| 151 | $PhCH_2O$ | H | H | F | O | A |
| 152 | $PhOCH_2$ | H | H | H | O | A |
| 153 | $CF_3$ | H | Cl | H | O | A |
| 154 | $CF_3$ | H | H | Cl | O | A |
| 155 | i-PrO | c-iPr | H | Cl | O | C |
| 156 | i-PrO | c-iPr | H | H | O | B |
| 157 | PhO | H | H | Cl | O | A |
| 158 | $PhCH_2O$ | H | H | H | O | A |
| 159 | $PhCH_2O$ | H | H | Br | O | A |
| 160 | $PhCH_2O$ | H | H | SMe | O | A |
| 161 | $PhCH_2O$ | H | H | Me | O | A |
| 162 | $PhCH_2O$ | H | H | Et | O | A |
| 163 | $PhCH_2O$ | c-Cl | H | Cl | O | A |
| 164 | $PhCH_2O$ | H | H | $CF_3$ | O | A |
| 165 | $PhCH_2O$ | H | H | Ph | O | A |
| 166 | $PhCH_2O$ | c-$PhCH_2O$ | H | Cl | O | A |
| 167 | $PhCH_2O$ | c-$PhCH_2O$ | H | H | O | A |
| 168 | $PhCH_2O$ | c-$PhCH_2O$ | H | i-Pr | O | A |
| 169 | MeO | o-$CF_3$ | H | H | O | B |
| 170 | $PhCH_2S$ | H | H | H | O | A |
| 171 | $PhCH_2S$ | H | H | Cl | O | A |
| 172 | Cl | H | H | H | S | D |
| 173 | $CF_3$ | c-$CF_3$ | H | Cl | S | A |
| 174 | $CF_3$ | c-Me | H | H | S | D |
| 175 | $CF_3$ | H | H | H | S | A |
| 176 | $CF_3$ | H | H | $CF_3$ | S | A |
| 177 | MeO | H | H | Cl | S | A |
| 178 | MeO | H | H | H | S | A |
| 179 | MeO | H | H | $CF_3$ | S | A |
| 180 | i-Bu | H | H | H | O | B |
| 181 | $PhCH_2O$ | H | H | Cl | O | A |
| 182 | $PhCH_2O$ | H | H | iPr | O | A |

D = Methyl ester

Reference Example 183

Ethyl 4'-[3-chloro-5-(trifluoromethyl)phenoxy]dihydrocinnamate

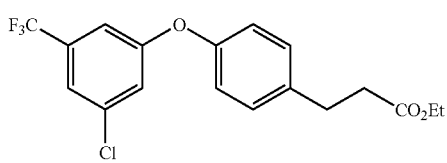

The compound of Reference Example 116 was reacted in the same manner as in Reference Example 124 to obtain ethyl 4'-[3-amino-5-(trifluoromethyl)phenoxy]dihydrocinnamate. An MeCN solution (15 mL) containing this compound (1.27 g) was added to an MeCN solution (40 mL) containing copper chloride (725 mg) and tBuONO (0.51 mL). This mixture was stirred for 3 hours at room temperature, followed by addition of water and extraction with ethyl acetate. The extract was then washed with water and the organic phase was dried over anhydrous sodium sulfate. The solvent was removed by distillation and the residue was purified on a silica gel column chromatography (hexane:ethyl acetate=20:1). This gave the desired product as a pale yellow oil (1.10 g).

Reference Example 184

Benzyl 4'-[3-benzyloxy-5-(trifluoromethyl)phenoxy]dihydrocinnamate

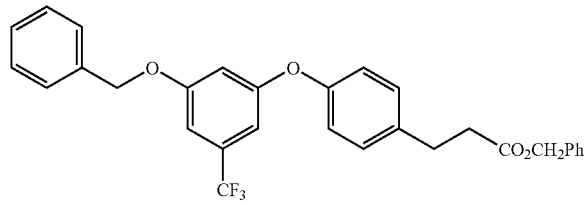

The compound of Reference Example 169 (840 mg) was dissolved in methylene chloride (20 mL). While the solution was stirred at 0° C., a 1 mol/L methylene chloride solution of tribromoboron (3.42 mL) was added dropwise. The reaction mixture was stirred at room temperature overnight. Subsequently, ice water was added, and the mixture was extracted with ethyl acetate and was washed sequentially with water and a saturated aqueous solution of sodium chloride. The organic phase was dried over anhydrous sodium sulfate. The solvent was then removed under reduced pressure to give 4'-(3-trifluoromethyl-5-hydroxyphenoxy)dihydrocinnamic acid as a pale brown powder (750 mg). The resulting powder was dissolved in DMF (50 mL). To this solution, potassium carbonate (1.04 g) and benzyl bromide (0.602 mL) were added and the mixture was stirred at room temperature for 8 hours. Subsequently, the reaction mixture was poured into ice water, and the mixture was extracted with ethyl acetate and was washed sequentially with water and a saturated aqueous solution of sodium chloride. The organic phase was then dried over anhydrous sodium sulfate. The solvent was removed under reduced pressure to give the desired product as a brown oil.

Reference Example 185

Benzyl 4'-(3-benzyloxyphenylthio)-2'-chlorodihydrocinnamate

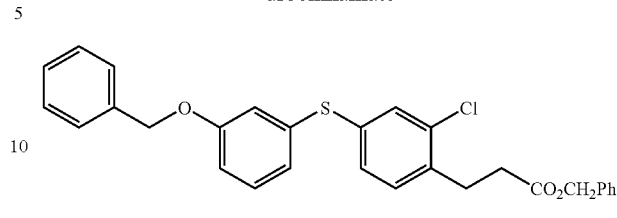

Using the compound of Reference Example 177, the reaction was carried out in the same manner as in Reference Example 184 to give the desired product as a yellow oil.

Reference Example 186

Benzyl 4'-(3-benzyloxyphenylthio)-dihydrocinnamate

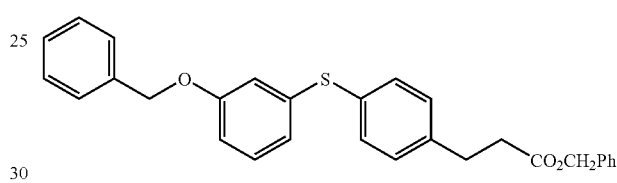

Using the compound of Reference Example 178, the reaction was carried out in the same manner as in Reference Example 184 to give the desired product as a yellow oil.

Reference Example 187

Ethyl 4'-[3-benzyloxy-5-(trifluoromethyl)phenoxy]-2'-chlorodihydrocinnamate

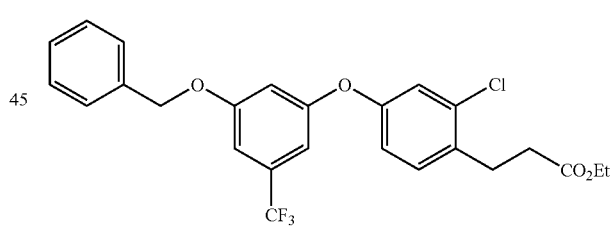

In the same manner as in Reference Example 184, the compound of Reference Example 142 was reacted to give 2'-chloro-4'-(3-trifluoromethyl-5-hydroxyphenoxy)dihydrocinnamic acid. This cinnamic acid (1.47 g) was dissolved in ethanol (10 mL). While this solution was stirred at 0° C., thionyl chloride (3 mL) was added dropwise. The mixture was stirred for 2 hours while kept at this temperature. Subsequently, the solvent was removed under reduced pressure and the residue was purified on a silica gel column chromatography (hexane:ethyl acetate=10:1 and then 6:1) to give ethyl 2'-chloro-4'-(3-trifluoromethyl-5-hydroxyphenoxy)dihydrocinnamate as a colorless oil (1.38 g). In the same manner as in Reference Example 184, the resulting ester was converted into a benzyl ether using potassium carbonate and benzyl bromide. This gave the desired product as a colorless oil.

Reference Example 188

Ethyl 4'-(3-benzyloxyphenylthio)-2'-trifluoromethyldihydrocinnamate

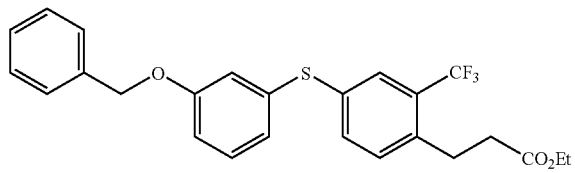

Using the compound of Reference Example 179, the reaction was carried out in the same manner as in Reference Example 187 to give the desired product as a colorless oil.

Reference Example 189

4'-[(3-benzyloxy)phenylthio]-2'-chlorodihydrocinnamyl alcohol

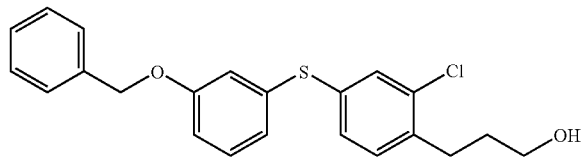

The compound of Reference Example 185 (7.40 g) was dissolved in THF (100 mL). While this solution was stirred at 0° C., lithium aluminum hydride (500 mg) was added. After 10 min, a 20% aqueous solution of NaOH was added and the crystallized insoluble inorganic residue was removed by filtration through Celite. The filtrate was extracted with ethyl acetate and the extract was washed sequentially with water and a saturated aqueous solution of sodium chloride. The organic phase was then dried over anhydrous sodium sulfate. The solvent was removed under reduced pressure to give the desired product as a colorless oil (6.37 g).

Reference Examples 190 through 251

In a similar manner to Reference Example 189, the compounds of Reference Examples 122 through 141, 143 through 168, 170 through 177 and 180 through 188 were used to synthesize the compounds shown in Table 4 below.

TABLE 4

| Reference Examples | R1 | R2 | R3 | R4 | X |
|---|---|---|---|---|---|
| 190 | Cl | c-Cl | H | Cl | O |
| 191 | t-Bu | H | H | H | O |
| 192 | Me | H | H | H | O |
| 193 | i-Pr | c-i-Pr | H | Cl | O |
| 194 | $C_5H_{11}$ | H | H | H | O |
| 195 | $C_7H_{15}$ | H | H | H | O |
| 196 | $CF_3$ | H | H | H | O |
| 197 | $CF_3$ | H | OMe | H | O |
| 198 | $CF_3$ | H | H | OMe | O |
| 199 | $CF_3$ | H | $CF_3$ | H | O |
| 200 | $CF_3$ | H | H | $CF_3$ | O |
| 201 | $CF_3$ | c-$CF_3$ | H | H | O |
| 202 | $CF_3$ | c-$CF_3$ | H | Cl | O |
| 203 | $CF_3$ | b-Cl | H | H | O |
| 204 | CF3 | a-Cl | H | H | O |
| 205 | CF3 | d-Cl | H | H | O |
| 206 | $CF_3$ | c-$PHCH_2O$ | H | Cl | O |
| 207 | $Ph(CH_2)_2$ | H | H | Cl | O |
| 208 | $Ph(CH_2)_2$ | H | H | $CF_3$ | O |
| 209 | $Ph(CH_2)_2$ | c-$CF_3$ | H | H | O |
| 210 | $Ph(CH_2)_2$ | c-$CF_3$ | H | Cl | O |
| 211 | $Ph(CH_2)_2$ | c-$Ph(CH_2)_2$ | H | H | O |
| 212 | $Ph(CH_2)_2$ | c-$Ph(CH_2)_2$ | H | $CF_3$ | O |
| 213 | $Ph(CH_2)_2$ | c-$Ph(CH_2)_2$ | H | Cl | O |
| 214 | $CF_3$ | H | H | F | O |
| 215 | $PhCH_2O$ | H | H | F | O |
| 216 | $CF_3$ | H | H | Cl | S |
| 217 | Et | H | H | H | O |
| 218 | $CF_3$ | H | H | $PhCH_2O$ | O |
| 219 | $CF_3$ | H | Cl | H | O |
| 220 | $CF_3$ | H | H | Cl | O |
| 221 | i-PrO | c-iPr | H | Cl | O |
| 222 | i-PrO | c-iPr | H | H | O |
| 223 | PhO | H | H | Cl | O |
| 224 | $PhCH_2O$ | H | H | H | O |
| 225 | $PhCH_2O$ | H | H | Br | O |
| 226 | $PhCH_2O$ | H | H | SMe | O |
| 227 | $PhCH_2O$ | H | H | Me | O |
| 228 | $PhCH_2O$ | H | H | Et | O |
| 229 | $PhCH_2O$ | c-Cl | H | Cl | O |
| 230 | $PhCH_2O$ | H | H | $CF_3$ | O |
| 231 | $PhCH_2O$ | H | H | Ph | O |
| 232 | $PhCH_2O$ | c-$PhCH_2O$ | H | Cl | O |
| 233 | $PhCH_2O$ | c-$PhCH_2O$ | H | H | O |
| 234 | $PhCH_2O$ | c-$PhCH_2O$ | H | i-Pr | O |
| 235 | $PhCH_2O$ | c-$CF_3$ | H | H | O |
| 236 | $PhCH_2S$ | H | H | H | O |
| 237 | $PhCH_2S$ | H | H | Cl | O |
| 238 | Cl | H | H | H | S |
| 239 | $CF_3$ | c-$CF_3$ | H | Cl | S |
| 240 | $CF_3$ | c-Me | H | H | S |
| 241 | $CF_3$ | H | H | H | S |
| 242 | $CF_3$ | H | H | $CF_3$ | S |
| 243 | MeO | H | H | Cl | S |
| 244 | $PhCH_2O$ | H | H | H | S |
| 245 | $PhCH_2O$ | H | H | $CF_3$ | S |
| 246 | i-Bu | H | H | H | O |
| 247 | $PhOCH_2$ | H | H | H | O |
| 248 | $CF_3$ | c-Cl | H | H | O |
| 249 | MeS | H | H | H | O |
| 250 | $PhCH_2O$ | H | H | Cl | O |
| 251 | $PhCH_2O$ | H | H | i-Pr | O |

Reference Example 252

4'-(3-benzyloxyphenylthio)-2'-chloro-dihydrocin-namyl iodide

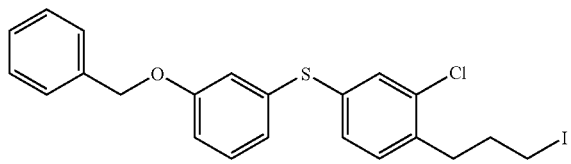

The compound of Reference Example 189 (1.38 g) was dissolved in THF (20 mL). While this solution was stirred at 0° C., imidazole (545 mg), triphenylphosphine (2.10 g) and iodine (2.00 g) were added. The mixture was stirred 2 hours at this temperature and subsequent 1.5 hours at room temperature, and additional imidazole (160 mg), triphenyl phosphine (600 mg) and iodine (500 mg) were added. The mixture was stirred overnight, followed by the addition of water and then sodium thiosulfate. The reaction mixture was then extracted with ethyl acetate and the extract was washed sequentially with water and a saturated aqueous solution of sodium chloride. The organic phase was then dried over anhydrous sodium sulfate. The solvent was removed under reduced pressure and the residue was purified on a silica gel column chromatography (hexane:ethyl acetate=50:1) to give the desired product as a colorless oil (1.55 g).

Reference Examples 253 through 314

In a similar manner to Reference Example 252, the compounds of Reference Examples 190 through 251 were used to synthesize the compounds shown in Table 5 below.

TABLE 5

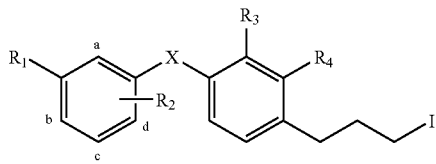

| Reference Examples | R1 | R2 | R3 | R4 | X |
|---|---|---|---|---|---|
| 253 | Cl | c-Cl | H | Cl | O |
| 254 | t-Bu | H | H | H | O |
| 255 | Me | H | H | H | O |
| 256 | i-Pr | c-i-Pr | H | Cl | O |
| 257 | $C_5H_{11}$ | H | H | H | O |
| 258 | $C_7H_{15}$ | H | H | H | O |
| 259 | $CF_3$ | H | H | H | O |
| 260 | $CF_3$ | H | OMe | H | O |
| 261 | $CF_3$ | H | H | OMe | O |
| 262 | $CF_3$ | H | $CF_3$ | H | O |
| 263 | $CF_3$ | H | H | $CF_3$ | O |
| 264 | $CF_3$ | c-$CF_3$ | H | H | O |
| 265 | $CF_3$ | c-$CF_3$ | H | Cl | O |
| 266 | $CF_3$ | b-Cl | H | H | O |
| 267 | $CF_3$ | a-Cl | H | H | O |
| 268 | $CF_3$ | d-Cl | H | H | O |
| 269 | $CF_3$ | c-$PhCH_2O$ | H | Cl | O |
| 270 | $Ph(CH_2)_2$ | H | H | Cl | O |
| 271 | $Ph(CH_2)_2$ | H | H | $CF_3$ | O |
| 272 | $Ph(CH_2)_2$ | c-$CF_3$ | H | H | O |
| 273 | $Ph(CH_2)_2$ | c-$CF_3$ | H | Cl | O |

TABLE 5-continued

| Reference Examples | R1 | R2 | R3 | R4 | X |
|---|---|---|---|---|---|
| 274 | $Ph(CH_2)_2$ | c-$Ph(CH_2)_2$ | H | H | O |
| 275 | $Ph(CH_2)_2$ | c-$Ph(CH_2)_2$ | H | $CF_3$ | O |
| 276 | $Ph(CH_2)_2$ | c-$Ph(CH_2)_2$ | H | Cl | O |
| 277 | $CF_3$ | H | H | F | O |
| 278 | $PhCH_2O$ | H | H | F | O |
| 279 | $CF_3$ | H | H | Cl | S |
| 280 | Et | H | H | H | O |
| 281 | $CF_3$ | H | H | $PhCH_2O$ | O |
| 282 | $CF_3$ | H | Cl | H | O |
| 283 | $CF_3$ | H | H | Cl | O |
| 284 | i-PrO | c-iPr | H | Cl | O |
| 285 | i-PrO | c-iPr | H | H | O |
| 286 | PhO | H | H | Cl | O |
| 287 | $PhCH_2O$ | H | H | H | O |
| 288 | $PhCH_2O$ | H | H | Br | O |
| 289 | $PhCH_2O$ | H | H | SMe | O |
| 290 | $PhCH_2O$ | H | H | Me | O |
| 291 | $PhCH_2O$ | H | H | Et | O |
| 292 | $PhCH_2O$ | c-Cl | H | Cl | O |
| 293 | $PhCH_2O$ | H | H | $CF_3$ | O |
| 294 | $PhCH_2O$ | H | H | Ph | O |
| 295 | $PhCH_2O$ | c-$PhCH_2O$ | H | Cl | O |
| 296 | $PhCH_2O$ | c-$PhCH_2O$ | H | H | O |
| 297 | $PhCH_2O$ | c-$PhCH_2O$ | H | i-Pr | O |
| 298 | $PhCH_2O$ | c-$CF_3$ | H | H | O |
| 299 | $PhCH_2S$ | H | H | H | O |
| 300 | $PhCH_2S$ | H | H | Cl | O |
| 301 | Cl | H | H | H | S |
| 302 | $CF_3$ | c-$CF_3$ | H | Cl | S |
| 303 | $CF_3$ | c-Me | H | H | S |
| 304 | $CF_3$ | H | H | H | S |
| 305 | $CF_3$ | H | H | $CF_3$ | S |
| 306 | MeO | H | H | Cl | S |
| 307 | $PhCH_2O$ | H | H | H | S |
| 308 | $PhCH_2O$ | H | H | $CF_3$ | S |
| 309 | i-Bu | H | H | H | O |
| 310 | $PhOCH_2$ | H | H | H | O |
| 311 | $CF_3$ | c-Cl | H | H | O |
| 312 | MeS | H | H | H | O |
| 313 | $PhCH_2O$ | H | H | Cl | O |
| 314 | $PhCH_2O$ | H | H | i-Pr | O |

Reference Example 315

4-(3,5-dichlorophenoxy)benzyl bromide

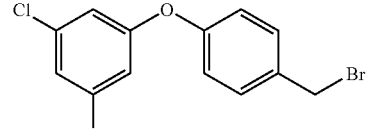

Using 3,5-dichlorophenol and 4-fluorobenzaldehyde, the reaction was carried out in the same manner as in Reference Example 1 to obtain 4-(3,5-dichlorophenoxy)benzaldehyde. Subsequently, the same procedure as in Reference Example 189 was followed using sodium borohydride in place of the lithium aluminum hydride. This gave 4-(3,5-dichlorophenoxy)benzyl alcohol. The resulting alcohol (2.03 g), along with carbon tetrabromide (2.75 g), was dissolved in methylene chloride (30 mL). While this solution was stirred at 0° C., triphenyl phosphine (2.17 g) was added. The mixture was stirred at 0° C. for 1 hour and at room temperature for the subsequent 30 min. The solvent was removed under reduced pressure and the residue was purified on a silica gel column chromatography (hexane:ethyl acetate=20:1) to give the desired product as a colorless oil (3.12 g).

Reference Example 316

1-iodopropyl-4-[(3-methanesulfinyl)phenoxy]benzene

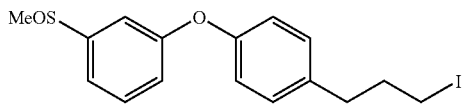

The compound of Reference Example 312 (1.80 g) was dissolved in methylene chloride (30 mL). While this solution was stirred at 0° C., m-chlorobenzoic acid (770 mg) was added in small portions. The mixture was stirred at this temperature for 1 hour and at room temperature for the subsequent 24 hours. Following addition of water, the mixture was extracted with ethyl acetate and the extract was washed sequentially with a saturated aqueous solution of sodium carbonate and a saturated aqueous solution of sodium chloride. The organic phase was then dried over anhydrous sodium sulfate. The solvent was removed under reduced pressure and the residue was purified on a silica gel column chromatography (hexane:ethyl acetate=2:1 and then 1:2) to give the desired product as a yellow oil (1.29 g).

Reference Example 317

4'-(3-benzyloxyphenylthio)-2'-chlorophenethyl iodide

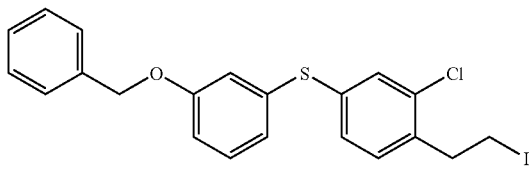

Reference Example 317-1

2'-chloro-4'-(3-methoxyphenylthio)benzyl cyanide

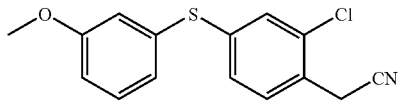

The compound of Reference Example 53 was treated in the same manner as in Reference Example 189 to obtain an alcohol. The alcohol (5.64 g) was dissolved in methylene chloride (100 mL) and phosphorus tribromide (2.25 mL) was added dropwise. Following stirring at room temperature for 1 hour, ice water was added and the mixture was extracted with ethyl acetate. The extract was washed sequentially with water and an aqueous solution of sodium chloride, and the organic phase was dried over anhydrous sodium sulfate. The solvent was removed by distillation to obtain a pale yellow oil. The oil and potassium cyanide (1.56 g) were dissolved in a mixture of DMSO (25 mL) and water (10 mL) and the solution was stirred at 90° C. for 5 hours. Following addition of water, the mixture was extracted with ethyl acetate and the extract was washed sequentially with water and a saturated aqueous solution of sodium chloride. The organic phase was dried over anhydrous sodium sulfate. The solvent was removed by distillation and the residue was purified on a silica gel column chromatography (hexane:ethyl acetate=10:1) to give the desired cyano-product as a pale yellow oil (3.81 g).

Reference Example 317-2

Ethyl 2'-chloro-4'-(3-methoxyphenylthio)phenylacetate

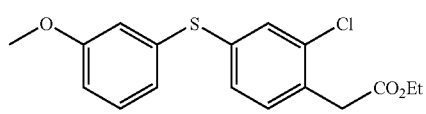

The cyano-product (3.81 g) and potassium hydroxide (3.68 g) were added to a mixture of ethanol (80 mL) and water (10 mL), and the solution was refluxed for 6 hours. Subsequently, the solution was allowed to cool and the insoluble material was removed by filtration. The filtrate was neutralized with diluted hydrochloric acid. This mixture was extracted with ethyl acetate and the extract was washed sequentially with water and a saturated aqueous solution of sodium chloride. The organic phase was then dried over anhydrous sodium sulfate. The solvent was removed by distillation and ethanol (50 mL) and thionyl chloride (2 mL) were added to the resulting residue. This mixture was stirred at room temperature for 1 hour and the solvent was removed by distillation. The resulting residue was purified on a silica gel column chromatography (hexane:ethyl acetate=10:1) to give the ethyl ester product as a colorless oil (3.89 g).

Reference Example 317-3

4'-(3-benzyloxyphenylthio)-21'-chlorophenethyl iodide

The ethyl ester was reacted in the same manner as in Reference Example 187 to obtain ethyl 4'-(3-benzyloxyphenylthio)-2'-chlorophenyl-acetate. The product was reduced as in Reference Example 189 to obtain an alcohol, which in turn was reacted in the same manner as in Reference Example 252 to give the desired product as a colorless oil.

Reference Example 318

1-(3-benzyloxyphenylthio)-3-chloro-4-iodobutylbenzene

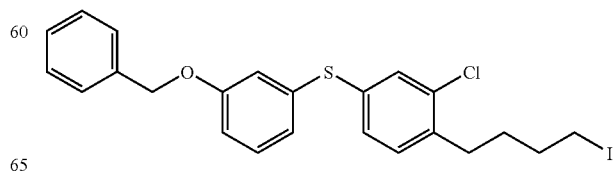

Reference Example 318-1

4-(3-benzyloxyphenylthio)-2-chlorophenethyl aldehyde

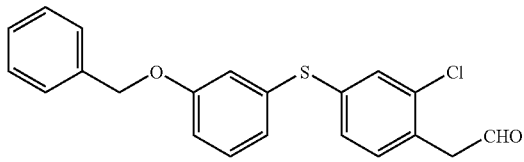

Ethyl 4'-(3-benzyloxyphenylthio)-2'-chlorophenylacetate obtained in Reference Example 317-3 was subjected to alkali-hydrolysis. The resulting product was condensed with N,O-dimethylhydroxylamine to form an amide product, which in turn was reduced in the same manner as in Reference Example 189 to give the desired aldehyde product as a yellow oil.

Reference Example 318-2

Ethyl 4-[(3-benzyloxyphenylthio)-2-chlorophenyl]butyrate

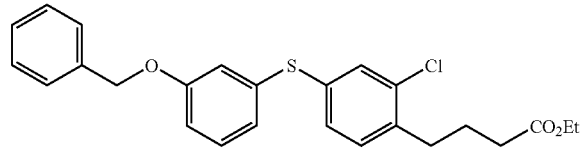

The compound of Reference Example 318-1 was reacted in the same manner as in Reference Example 60 and the unsaturated bonds of the resulting product were reduced in the same manner as in Reference Example 122 to give the desired ethyl butyrate derivative.

Reference Example 318-3

1-(3-benzyloxyphenylthio)-3-chloro-4-iodobutylbenzene

The compound of Reference Example 318-2 was reacted in the same manner as in Reference Example 189 to obtain an alcohol product, which in turn was reacted in the same manner as in Reference Example 252 to give the desired product as a colorless oil.

Reference Example 319

4'-[(3-benzyloxy)phenoxy]-2'-chlorophenethyl iodide

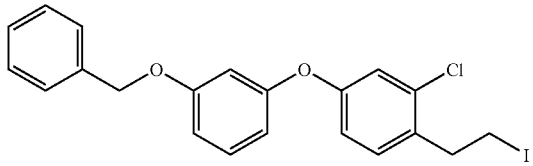

The compound of Reference Example 56 was reacted in the same manner as in Reference Example 317 to obtain the desired product as a yellow oil.

Reference Example 320

4-[(3-benzyloxy)phenoxy]-2-chloro-1-iodobutylbenzene

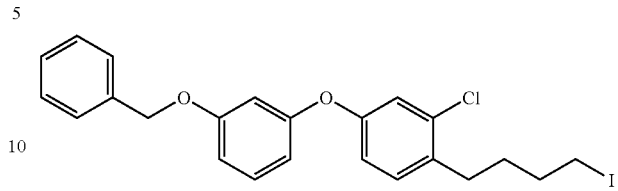

The compound of Reference Example 56 was reacted in the same manner as in Reference Example 318 to obtain the desired product as a pale yellow oil.

Reference Example 321

4'-benzyloxydihydrocinnamyl iodide

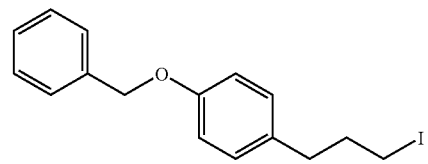

4'-benzyloxydihydrocinnamyl alcohol was reacted in the same manner as in Reference Example 252 to obtain the desired product as a yellow powder.

Reference Example 322

4'-(3-benzyloxyphenylthio)-2'-chlorobenzyl bromide

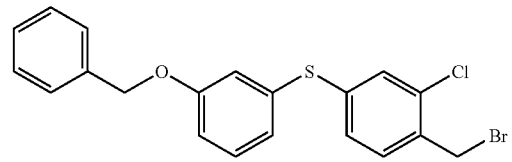

In place of 2-chloro-4-fluorobenzaldehyde, 2-chloro-4-fluorobenzonitrile was reacted in the same manner as in Reference Example 1 to obtain 2-chloro-4-(3-methoxyphenylthio)benzonitrile. Following the same procedure as in Reference Example 317-2, this product was hydrolyzed and, then, following the same procedure as in Reference Example 187, the methoxy group was decomposed and esterified to convert the product into a benzyl ether. The product was then reacted in the same manner as in Reference Example 189 to be converted into an alcohol. Subsequently, the product was reacted with carbon tetrabromide in the same manner as in Reference Example 315 to obtain the desired product as a colorless oil.

Reference Example 323

2'-chloro-4'-(4-trifluoromethylphenoxy)dihydrocinnamyl iodide

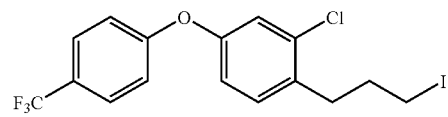

Using p-trifluoromethylphenol, the reaction was carried out in the same manner as in Reference Example 1 to obtain an aldehyde. Following the same procedure as in Reference Example 60, the aldehyde was subjected to Horner-Emmons reaction. Subsequently, following the same procedure as in Reference Example 123, the resulting product was reduced and, then, following the same procedure as in Reference Example 189, the reduced product was converted into an alcohol. Subsequently, the alcohol was iodized in the same manner as in Reference Example 252 to give the desired product as a colorless oil.

MS(EI+): 440([M]$^+$).

$^1$H-NMR(400 MHz, CDCl$_3$) δ 2.12-2.19(2H, m), 2.85(2H, t, J=7.3 Hz), 3.21(2H, t, J=7.3 Hz), 6.90(1H, dd, J=2.5, 8.6 Hz), 7.04-7.08(3H, m), 7.23-7.27(1H, m), 7.60(2H, d, J=8.6 Hz).

Reference Example 324

2'-chloro-4'-(2-trifluoromethylphenoxy)dihydrocinnamyl iodide

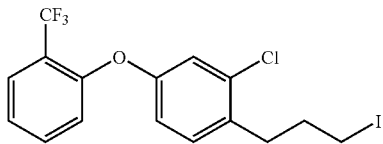

Using o-trifluoromethylphenol, the reaction was carried out in the same manner as in Reference Example 232 to obtain the desired product as a colorless oil.

MS(EI+): 440([M]$^+$).

$^1$H-NMR(400 MHz, CDCl$_3$) δ 2.11-2.18(2H, m), 2.83(2H, t, J=7.3 Hz), 3.21(2H, t, J=7.3 Hz), 6.88(1H, dd, J=2.5, 8.6 Hz), 6.96(1H, d, J=8.6 Hz), 7.04(1H, d, J=2.5 Hz), 7.18-7.26 (2H, m), 7.49(1H, t, J=8.6 Hz), 7.68(1H, d, J=8.0 Hz).

Reference Example 325

4-(4-benzyloxyphenylthio)-2-chlorobenzaldehyde

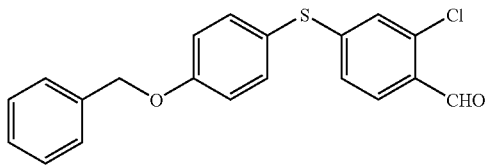

p-hydroxythiophenol (2.12 g) was dissolved in N,N-dimethylformamide (40 mL). To this solution, 2-chloro-4-fluorobenzaldehyde (2.66 g) and potassium carbonate (4.64 g) were added and the mixture was stirred for 2 hours at 50° C. Subsequently, benzyl bromide (4.00 mL) was added and the mixture was stirred for 1.5 hours at 50° C. and then for 2.5 hours at 70° C. The reaction mixture was extracted with ethyl acetate and the extract was washed sequentially with water and a saturated aqueous solution of sodium chloride. The organic phase was then dried over anhydrous sodium sulfate. Following addition of water, the solvent was removed by distillation and the residue was purified on a silica gel column chromatography (hexane:ethyl acetate=10:1). This gave the desired product as a colorless solid (5.70 g).

$^1$H-NMR(400 MHz, CDCl$_3$) δ 5.12(2H, s), 6.96-7.03(3H, m), 7.06(2H, m), 7.38-7.50(6H, m), 8.56(1H, d, J=8.6 Hz), 10.33(1H, s).

Reference Example 326

4'-(4-benzyloxyphenylthio)-2'-chlorophenethylaldehyde

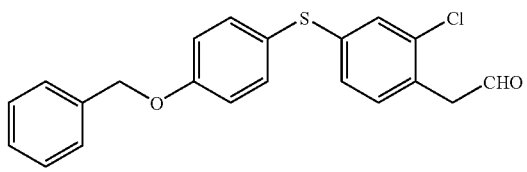

To an ice-cold tetrahydrofuran solution (160 mL) of (Methoxymethyl)triphenylphosphonium chloride (8.28 g), t-butoxy potassium (2.71 g) was added and the mixture was stirred for 1 hour, followed by addition of the compound of Reference Example 325 (5.70 g) and 1 hour of stirring. Subsequently, water was added to the mixture and the mixture was extracted with ethyl acetate and the extract was washed sequentially with water and a saturated aqueous solution of sodium chloride. The organic phase was then dried over anhydrous sodium sulfate. The solvent was removed by distillation and the resulting residue was purified on a silica gel column chromatography (hexane:ethyl acetate=6:1). This gave the desired vinyl ether product as a pale yellow oil (6.50 g). This product was dissolved in tetrahydrofuran (90 mL). To this solution, a 6 mol/L aqueous solution of hydrochloric acid (60 mL) was added and the mixture was stirred for 5 hours at 60° C. Subsequently, the reaction mixture was extracted with ethyl acetate. The extract was washed sequentially with water and a saturated aqueous solution of sodium chloride and the organic phase was dried over anhydrous sodium sulfate. Following addition of water, the solvent was removed by distillation and the residue was purified on a silica gel column chromatography (hexane:ethyl acetate=9:1). This gave the desired product as a colorless powder (4.48 g).

$^1$H-NMR(400 MHz, CDCl$_3$) δ 3.77(2H, d, J=1.8 Hz), 5.09 (2H, s), 6.97-7.04(3H, m), 7.05-7.10(1H, m), 7.15(1H, d, J=1.8 Hz), 7.32-7.46(7H, m), 9.72(1H, t, J=1.8 Hz).

Reference Example 327

4'-(4-benzyloxyphenylthio)-2'-chlorophenethyl iodide

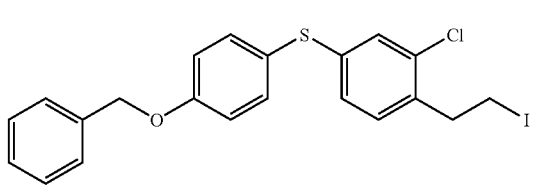

Following the same procedure as in Reference Example 189, the compound of Example 326 was converted into an alcohol. Then, using the same procedure as in Reference Example 252, this alcohol was iodized to give the desired product as a pale yellow oil.

$^1$H-NMR(400 MHz, CDCl$_3$) δ 3.22(2H, t, J=7.3 Hz), 3.30 (2H, t, J=7.3 Hz), 5.09(2H, s) 6.96-7.02(3H, m), 7.09(2H, d, J=7.9 Hz), 7.33-7.45(7H, m).

Example 1

Ethyl 2-t-butoxycarbonylamino-5-[2-chloro-4-(3-trifluoromethylphenylthio)phenyl]-2-etoxycarbonyl-pentanoate

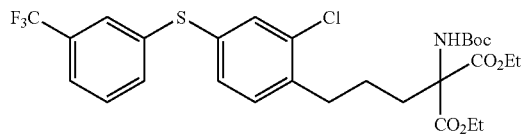

At room temperature and under a stream of argon gas, sodium t-butoxide (490 mg) was added to diethyl 2-t-butoxycarbonylaminomalonate (1.3 mL) in a mixture of THF (35 mL) and DMF (4 mL). This mixture was stirred for 20 min at 80° C. and was allowed to cool to room temperature. To the cooled mixture, a THF solution (5 mL) of the compound of Reference Example 279 (1.55 g) was added dropwise. The resulting mixture was refluxed for 5 hours, was poured into ice water, and was extracted with ethyl acetate. The extract was washed sequentially with water and a saturated aqueous solution of sodium chloride. The organic phase was then dried over anhydrous sodium sulfate. The solvent was removed under reduced pressure and the residue was purified on a silica gel column chromatography (hexane:ethyl acetate=5:1) to give the desired product as a colorless oil (1.87 g).

$^1$H-NMR(400 MHz, CDCl$_3$) δ 1.22-1.36(6H, m), 1.42(9H, s), 1.45-1.53(2H, m), 2.37(2H, br), 2.74(2H, t, J=7.8 Hz), 4.23(4H, m), 5.94(1H, s), 7.16-7.21(2H, m), 7.36-7.56(5H, m).

<Examples 2 through 67

In a similar manner to Example 1, the halogen derivatives of respective Reference Examples were used to synthesize the compounds shown in Tables 6 and 7 below.

TABLE 6

| Examples | R1 | R2 | R3 | R4 | X | n | Characteristics | Yield (%) |
|---|---|---|---|---|---|---|---|---|
| 2 | Cl | c-Cl | H | Cl | O | 3 | Colorless oil | 74 |
| 3 | t-Bu | H | H | H | O | 3 | Colorless oil | 64 |
| 4 | CF$_3$ | H | H | H | O | 3 | Colorless oil | 100 |
| 5 | CF$_3$ | H | OMe | H | O | 3 | Colorless oil | 100 |
| 6 | CF$_3$ | H | H | OMe | O | 3 | Colorless oil | 100 |
| 7 | CF$_3$ | H | CF$_3$ | H | O | 3 | Colorless oil | 100 |
| 8 | CF$_3$ | H | H | CF$_3$ | O | 3 | Colorless oil | 92 |
| 9 | CF$_3$ | c-CF$_3$ | H | H | O | 3 | Yellow oil | 47 |
| 10 | CF$_3$ | c-CF$_3$ | H | Cl | O | 3 | Colorless oil | 89 |
| 11 | CF$_3$ | b-Cl | H | H | O | 3 | Colorless oil | 94 |
| 12 | CF$_3$ | c-PhCH$_2$O | H | Cl | O | 3 | Colorless oil | 91 |
| 13 | Ph(CH$_2$)$_2$ | H | H | Cl | O | 3 | Colorless oil | 83 |
| 14 | Ph(CH$_2$)$_2$ | H | H | CF$_3$ | O | 3 | Colorless oil | 90 |
| 15 | Ph(CH$_2$)$_2$ | c-CF$_3$ | H | H | O | 3 | Colorless oil | 97 |
| 16 | Ph(CH$_2$)$_2$ | c-Ph(CH$_2$)$_2$ | H | H | O | 3 | Colorless oil | 95 |
| 17 | Ph(CH$_2$)$_2$ | c-Ph(CH$_2$)$_2$ | H | CF$_3$ | O | 3 | Colorless oil | 100 |
| 18 | Ph(CH$_2$)$_2$ | c-Ph(CH$_2$)$_2$ | H | Cl | O | 3 | Colorless oil | 98 |
| 19 | i-PrO | o-iPr | H | Cl | O | 3 | Colorless oil | 100 |
| 20 | PhO | H | H | Cl | O | 3 | Colorless oil | 92 |
| 21 | PhCH$_2$O | H | H | H | O | 3 | Colorless oil | 95 |
| 22 | PhCH$_2$O | H | H | Br | O | 3 | Colorless oil | 100 |
| 23 | PhCH$_2$O | H | H | SMe | O | 3 | Colorless oil | — |
| 24 | PhCH$_2$O | H | H | Me | O | 3 | Colorless oil | 100 |
| 25 | PhCH$_2$O | H | H | Et | O | 3 | Colorless oil | 72 |
| 26 | PhCH$_2$O | H | H | Cl | S | 2 | Pale yellow oil | 100 |
| 27 | PhCH$_2$O | H | H | Cl | S | 3 | Colorless oil | 100 |
| 28 | PhCH$_2$O | H | H | Cl | S | 4 | Colorless oil | 100 |
| 29 | PhCH$_2$O | c-CF$_3$ | H | H | O | 3 | Colorless oil | 99 |
| 30 | Cl | H | H | H | S | 3 | Colorless oil | 82 |
| 31 | CF$_3$ | c-CF$_3$ | H | Cl | S | 3 | Colorless oil | 66 |
| 32 | Et | H | H | H | O | 3 | Colorless oil | 100 |
| 33 | SOMe | H | H | H | O | 3 | Colorless oil | 100 |
| 34 | Cl | c-Cl | H | H | O | 1 | Colorless oil | 56 |
| 35 | CF$_3$ | H | H | PhCH$_2$O | O | 3 | Colorless oil | 100 |
| 36 | PhCH$_2$O | H | H | Cl | O | 3 | Colorless oil | 100 |
| 37 | CF$_3$ | H | Cl | H | O | 3 | Colorless oil | 100 |
| 38 | CF$_3$ | H | H | Cl | O | 3 | Colorless oil | 100 |
| 39 | PhCH2O | H | H | F | O | 3 | Colorless oil | 100 |
| 40 | CF$_3$ | c-Cl | H | H | O | 3 | Colorless oil | 100 |

—Yield is shown in Tables 8-14 10 in association with the subsequent step.

TABLE 7 structure

| Examples | R1 | R2 | R3 | R4 | X | n | Characteristics | Yield (%) |
|---|---|---|---|---|---|---|---|---|
| 41 | $CF_3$ | c-Cl | H | H | O | 3 | Pale yellow oil | 41 |
| 42 | $CF_3$ | d-Cl | H | H | O | 3 | Pale yellow oil | 72 |
| 43 | $Ph(CH_2)_2$ | c-$CF_3$ | H | Cl | O | 3 | Colorless oil | 93 |
| 44 | $PhCH_2O$ | H | H | Cl | O | 2 | Colorless oil | — |
| 45 | $PhCH_2O$ | H | H | Cl | O | 4 | Colorless oil | — |
| 46 | $CF_3$ | H | H | F | O | 3 | Colorless oil | 100 |
| 47 | $PhCH_2O$ | c-$PhCH_2O$ | H | H | O | 3 | Colorless oil | — |
| 48 | $PhCH_2O$ | c-$PhCH_2O$ | H | Cl | O | 3 | Colorless oil | — |
| 49 | $PhCH_2O$ | c-Cl | H | Cl | O | 3 | Colorless oil | 100 |
| 50 | $PhCH_2O$ | H | H | $CF_3$ | O | 3 | Colorless oil | 100 |
| 51 | $PhCH_2O$ | H | H | Ph | O | 3 | Colorless oil | — |
| 52 | MeS | H | H | H | O | 3 | Colorless oil | 83 |
| 53 | n-$C_5H_{11}$ | H | H | H | O | 3 | Colorless oil | 86 |
| 54 | c-$C_7H_{15}$ | H | H | H | O | 3 | Colorless oil | 88 |
| 55 | iPr | c-iPrO | H | H | O | 3 | Colorless oil | 95 |
| 56 | iPr | c-iPr | H | Cl | O | 3 | Colorless oil | 86 |
| 57 | $PhCH_2S$ | H | H | H | O | 3 | Colorless oil | — |
| 58 | $PhCH_2S$ | H | H | Cl | O | 3 | Colorless oil | — |
| 59 | i-Bu | H | H | H | O | 3 | Colorless oil | 76 |
| 60 | $PhOCH_2$ | H | H | H | O | 3 | Colorless oil | 100 |
| 61 | $PhCH_2O$ | H | H | i-Pr | O | 3 | Colorless oil | — |
| 62 | $CF_3$ | H | H | H | S | 3 | Colorless oil | 90 |
| 63 | $CF_3$ | H | H | $CF_3$ | S | 3 | Pale yellow oil | 53 |
| 64 | $CF_3$ | c-Me | H | H | S | 3 | Colorless oil | 100 |
| 65 | MeO | H | H | Cl | S | 3 | Colorless oil | 87 |
| 66 | $PhCH_2O$ | H | H | H | S | 3 | Colorless oil | — |
| 67 | $PhCH_2O$ | H | H | $CF_3$ | S | 3 | Colorless oil | 100 |
| 68 | $PhCH_2O$ | H | H | Cl | S | 1 | Colorless oil | 100 |

— Yield is shown in Tables 8-10 in association with the subsequent step.

Example 69

Ethyl 5-[(4-benzyloxy)phenyl]-2-t-butoxycarbonylamino-2-ethoxycarbonylpentanoate

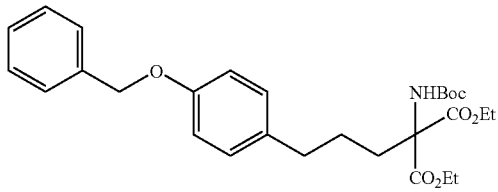

The compound of Reference Example 321 was reacted in the same manner as in Example 1 to give the desired product as a pale yellow oil.

$^1$H-NMR(400 MHz, $CDCl_3$) δ 1.22(6H, t, J=7.1 Hz), 1.42 (9H, s), 1.44-1.47(2H, m), 2.31(2H, br s), 2.57(2H, t, J=7.6 Hz), 4.11-4.27(4H, m), 5.03(2H, s), 5.92(1H, br s), 6.88(2H, d, J=8.8 Hz), 7.06(2H, d, J=8.8 Hz), 7.29-7.43(5H, m).

Example 70

Ethyl 2-t-butoxycarbonylamino-2-ethoxycarbonyl-5-[4-(3-isopropoxyphenoxy)phenyl]pentanoate

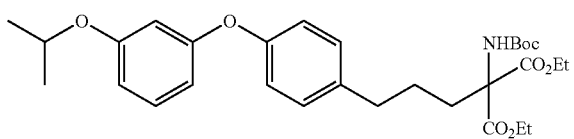

The compound of Example 69 was reduced in the same manner as in Reference Example 123. The resulting phenol product (850 mg) was dissolved in DMF (20 mL). To this solution, 2-iodopropane (0.2 mL) and potassium carbonate (500 mg) were added and the mixture was stirred for 4 hours at 60° C. Following addition of water, the mixture was extracted with ethyl acetate and the extract was washed sequentially with water and a saturated aqueous solution of sodium chloride. The organic phase was dried over anhydrous sodium sulfate. The solvent was removed under reduced pressure and the residue was purified on a silica gel column chromatography (hexane:ethyl acetate=4:1) to give the desired product as a colorless oil (760 mg).

$^1$H-NMR(400 MHz, $CDCl_3$) δ 1.23(6H, t, J=7.3 Hz), 1.31 (6H, d, J=5.9 Hz), 1.42(9H, s), 1.45-1.52(2H, m), 2.34(2H, br), 2.61(2H, t, J=7.8 Hz), 4.17-4.27(4H, m), 4.50(1H, heptet, 5.9 Hz), 5.94(1H, br s), 6.50-6.53(2H, m), 6.59-6.62(1H, m), 6.92(2H, d, J=8.8 Hz), 7.10(2H, d, J=8.8 Hz), 7.18(1H, t, J=8.8 Hz).

Example 71

Ethyl 2-t-butoxycarbonylamino-5-[4-(3,5-dichlorophenoxy)phenyl]-2-ethoxycarbonylpentanoate

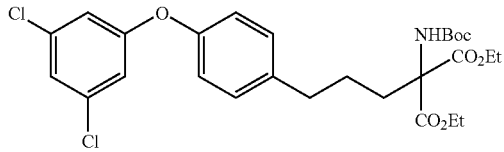

The compound of Example 69 was reduced in the same manner as in Reference Example 123. The resulting phenol product (1.27 g), along with 3,5-dichlorophenylboric acid (1.18 g), was dissolved in methylene chloride (30 mL). While this solution was being stirred, copper acetate (676 mg) and triethylamine (0.86 mL) were added. After 16 hours and a further 8 hours later, the same amount of additional copper acetate was added and the mixture was stirred for the subsequent 40 hours. Subsequently, the insoluble material was removed by filtration. The filtrate was poured into water and the mixture was extracted with ethyl acetate. The extract was washed sequentially with water and a saturated aqueous solution of sodium chloride. The organic phase was then dried over anhydrous magnesium sulfate. The solvent was removed under reduced pressure and the residue was purified on a silica gel column chromatography (hexane:ethyl acetate=20:1) to give the desired product as a pale blue oil (333 mg).

Example 72

Ethyl 2-t-butoxycarbonylamino-2-ethoxycarbonyl-5-[4-(3-methanesulfonylphenoxy)phenyl]pentanoate

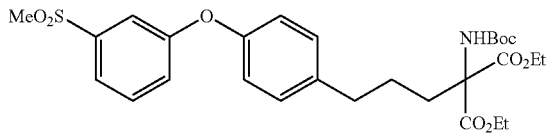

The compound of Example 33 (1.00 g) was dissolved in methylene chloride (30 mL). To this solution, m-chloroperbenzoic acid (610 mg) was added and the mixture was stirred for 6 hours at room temperature. Following addition of water, the mixture was extracted with ethyl acetate and the extract was washed sequentially with a saturated aqueous solution of sodium hydrogen carbonate and with a saturated aqueous solution of sodium chloride. The organic phase was dried over anhydrous sodium sulfate. The solvent was removed under reduced pressure and the residue was purified on a silica gel column chromatography (hexane:ethyl acetate=1:1) to give the desired product as a colorless oil (610 mg).

$^1$H-NMR(400 MHz, CDCl$_3$) δ 1.24(6H, t, J=7.3 Hz), 1.42 (9H, s), 1.47-1.56(2H, m), 2.34(2H, br), 2.64(2H, t, J=7.8 Hz), 3.04(3H, s), 4.18-4.26(4H, m), 5.95(1H, br), 6.95(2H, d, J=8.8 Hz), 7.17(2H, t, J=8.8 Hz), 7.20-7.30(3H, m), 7.47-7.52(2H, m), 7.62(1H, d, J=8.8 Hz).

Example 73

Ethyl 2-t-butoxycarbonylamino-2-ethoxycarbonyl-5-[4-(3-trifluoromethylphenylsulfinyl)]phenylpentanoate

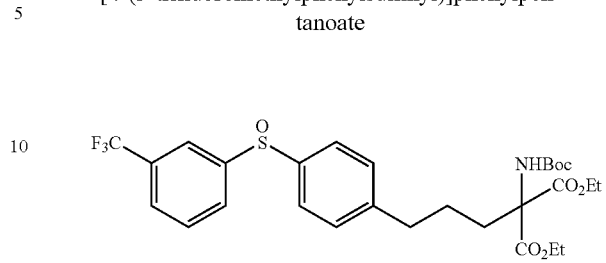

The compound of Example 62 (1.50 g) was dissolved in methylene chloride (80 mL). While this solution was stirred at 0° C., m-chloroperbenzoic acid (450 mg) was added in small portions. The mixture was then stirred for 1 hour at this temperature and 2 hours at room temperature. Subsequently, water was added to the reaction mixture and the mixture was extracted with ethyl acetate. The extract was washed sequentially with a saturated aqueous solution of sodium hydrogen carbonate and with a saturated aqueous solution of sodium chloride. The organic phase was dried over anhydrous sodium sulfate. The solvent was removed under reduced pressure and the residue was purified on a silica gel column chromatography (hexane:ethyl acetate=1:1) to give the desired product as a yellow oil (1.10 g).

$^1$H-NMR(400 MHz, CDCl$_3$) δ 1.18-1.21(6H, m), 1.40(9H, s), 1.44-1.52(2H, m), 2.30(2H, br), 2.66(2H, t, J=7.3 Hz), 4.14-4.22(4H, m), 5.91(1H, br), 7.27(2H, d, J=8.3 Hz), 7.56 (2H, d, J=8.3 Hz), 7.59(1H, t, J=8.3 Hz), 7.69(1H, d, J=8.3 Hz), 7.78(1H, d, J=8.3 Hz), 7.95(1H, s).

Example 74

Ethyl 2-t-butoxycarbonylamino-2-ethoxycarbonyl-5-[4-(3-trifluoromethyl-5-methylphenylsulfinyl)]phenylpentanoate

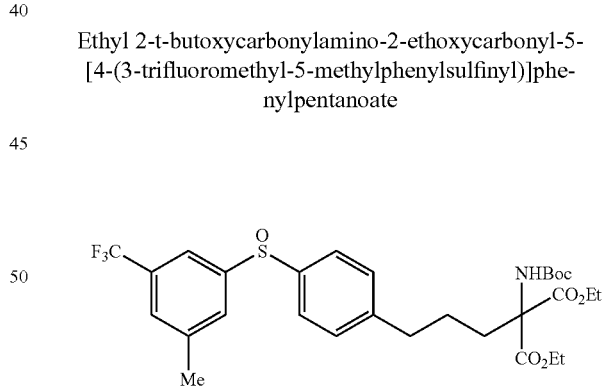

In a similar manner to Example 73, the compound of Example 64 was used to obtain the desired product as a colorless oil.

FABMS:600([M+H]$^+$).

$^1$H-NMR(400 MHz, CDCl$_3$) δ 1.18-1.22(6H, m), 1.41(9H, s), 1.46-1.50(2H, m), 2.31(2H, br), 2.45(3H, s), 2.66(2H, t, J=7.3 Hz), 4.14-4.22(4H, m), 5.92(1H, br s), 7.27(2H, d, J=7.8 Hz), 7.48(1H, s), 7.55(2H, d, J=7.8 Hz), 7.62(1H, s), 7.70(1H, s).

Example 75

Alternative Process for Synthesizing the Compound of Example 9

Ethyl 5-[4-(3,5-bistrifluoromethylphenoxy)phenyl]-2-t-butoxycarbonylamino-2-ethoxycarbonylpentanoate

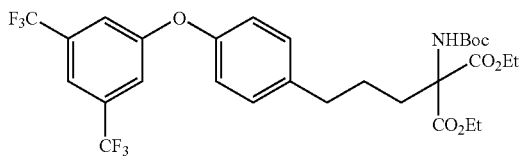

In a similar manner to Reference Example 123, the compound of Example 69 was reduced and, then, in a similar manner to Example 71, the resulting phenol was reacted with 3,5-bis(trifluoromethyl)phenylboric acid to give the desired product as a pale yellow oil.

$^1$H-NMR(400 MHz, CDCl$_3$) δ 1.24(6H, t, J=7.3 Hz), 1.43 (9H, s), 1.47-1.58(4H, m), 2.36(2H, br s), 2.66(2H, t, J=7.3 Hz), 4.18-4.26(4H, m), 5.96(1H, br s), 6.96(2H, d, J=8.3 Hz), 7.20(2H, d, J=8.3 Hz), 7.36(2H, s), 7.55(1H, s).

Examples 76 and 77

2-t-butoxycarbonylamino-2-[2-chloro-4-(3-trifluoromethylphenylthio)phenyl]propyl-1,3-propanediol (Example 76);

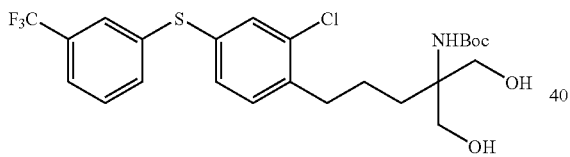

and 2-t-butoxycarbonylamino-5-[2-chloro-4-(3-trifluoromethylphenylthio)phenyl]pentane-1-ol (Example 77)

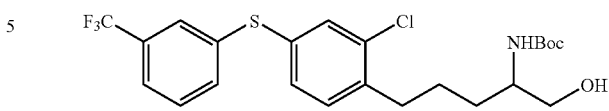

The compound of Example 1 (1.87 g) was dissolved in THF (30 mL). While this solution was stirred at 0° C., lithium borohydride (675 mg) was added. Ethanol (5 mL) was added and the mixture was allowed to gradually warm to room temperature while being stirred overnight. Subsequently, ice water was added to the mixture and the organic solvent was removed under reduced pressure. A 10% aqueous citric acid was added to the residue to adjust the pH to 3, followed by extraction with ethyl acetate. The extract was washed sequentially with water and a saturated aqueous solution of sodium chloride. The organic phase was then dried over anhydrous sodium sulfate and the solvent was removed under reduced pressure. The residue was purified on a silica gel column chromatography (hexane:ethyl acetate=1:1) to give-the diol (1.10 g) or the monool (0.27 g), each as a colorless oil.

Compound of Example 76

FABMS:520([M+H]$^+$).
$^1$H-NMR(400 MHz, CDCl$_3$) δ1.43(9H, s), 1.62-1.65(4H, m), 2.72(2H,br), 3.31(2H, br), 3.57-3.62(2H, m), 3.81-3.85 (2H, m), 4.93(1H, s), 7.20-7.27(3H, m), 7.38-7.55(4H, m).

Compound of Example 77

FABMS:490([M+H]$^+$).
$^1$H-NMR(400 MHz, CDCl$_3$) δ 1.44(9H, s), 1.63-1.73(4H, m), 2.72-2.78(2H, m), 3.57(1H, br), 3.68-3.70(2H, m), 4.61 (1H, br s), 7.20-7.22(2H, m), 7.39-7.55(5H, m).

Examples 78 through 184

In a similar manner to Example 76, the compounds of 2 through 68 and 70 through 74 were used to synthesize compounds shown in Tables 8 through 10 below.

TABLE 8

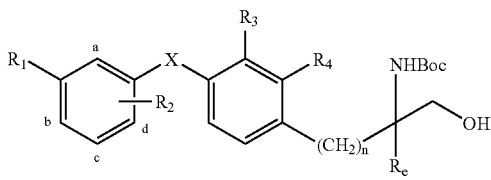

| Examples | R1 | R2 | R3 | R4 | R5 | X | n | Characteristics | Yield (%) |
|---|---|---|---|---|---|---|---|---|---|
| 78 | Cl | c-Cl | H | Cl | CH$_2$OH | O | 3 | Colorless oil | 79 |
| 79 | Cl | c-Cl | H | Cl | H | O | 3 | Colorless oil | 12 |
| 80 | t-Bu | H | H | H | CH$_2$OH | O | 3 | Colorless oil | 78 |
| 81 | t-Bu | H | H | H | H | O | 3 | Colorless oil | 15 |
| 82 | CF$_3$ | H | H | H | CH$_2$OH | O | 3 | Colorless oil | 74 |
| 83 | CF$_3$ | H | H | H | H | O | 3 | Colorless oil | 17 |
| 84 | CF$_3$ | H | OMe | H | CH$_2$OH | O | 3 | Colorless oil | 76 |
| 85 | CF$_3$ | H | OMe | H | H | O | 3 | Colorless oil | 5 |
| 86 | CF$_3$ | H | H | OMe | CH$_2$OH | O | 3 | Colorless oil | 45 |
| 87 | CF$_3$ | H | H | OMe | H | O | 3 | Colorless oil | 17 |
| 88 | CF$_3$ | H | CF$_3$ | H | CH$_2$OH | O | 3 | Colorless oil | 68 |

TABLE 8-continued

| Examples | R1 | R2 | R3 | R4 | R5 | X | n | Characteristics | Yield (%) |
|---|---|---|---|---|---|---|---|---|---|
| 89 | $CF_3$ | H | $CF_3$ | H | H | O | 3 | Colorless oil | 16 |
| 90 | $CF_3$ | H | H | $CF_3$ | $CH_2OH$ | O | 3 | Colorless oil | 41 |
| 91 | $CF_3$ | H | H | $CF_3$ | H | O | 3 | Colorless oil | 22 |
| 92 | $CF_3$ | c-$CF_3$ | H | H | $CH_2OH$ | O | 3 | Colorless oil | 72 |
| 93 | $CF_3$ | c-$CF_3$ | H | H | H | O | 3 | Yellow oil | 14 |
| 94 | $CF_3$ | c-$CF_3$ | H | Cl | $CH_2OH$ | O | 3 | Colorless oil | 77 |
| 95 | $CF_3$ | c-$CF_3$ | H | Cl | H | O | 3 | Colorless oil | 19 |
| 96 | $CF_3$ | b-Cl | H | H | $CH_2OH$ | O | 3 | Colorless powder | 62 |
| 97 | $CF_3$ | b-Cl | H | H | H | O | 3 | Colorless powder | 29 |
| 98 | $CF_3$ | c-$PhCH_2O$ | H | Cl | $CH_2OH$ | O | 3 | Colorless oil | 67 |
| 99 | $CF_3$ | c-$PhCH_2O$ | H | Cl | H | O | 3 | Colorless oil | 12 |
| 100 | $Ph(CH_2)_2$ | H | H | Cl | $CH_2OH$ | O | 3 | Colorless oil | 84 |
| 101 | $Ph(CH_2)_2$ | H | H | Cl | H | O | 3 | Colorless oil | 15 |
| 102 | $Ph(CH_2)_2$ | H | H | $CF_3$ | $CH_2OH$ | O | 3 | Colorless oil | 72 |
| 103 | $Ph(CH_2)_2$ | H | H | $CF_3$ | H | O | 3 | Colorless oil | 18 |
| 104 | $Ph(CH_2)_2$ | c-$CF_3$ | H | H | $CH_2OH$ | O | 3 | Colorless oil | 80 |
| 105 | $Ph(CH_2)_2$ | c-$CF_3$ | H | H | H | O | 3 | Colorless oil | 16 |
| 106 | $Ph(CH_2)_2$ | c-$Ph(CH_2)_2$ | H | H | $CH_2OH$ | O | 3 | Colorless oil | 71 |
| 107 | $Ph(CH_2)_2$ | c-$Ph(CH_2)_2$ | H | H | H | O | 3 | Colorless oil | 11 |
| 108 | $PH(CH_2)_2$ | c-$Ph(CH_2)_2$ | H | $CF_3$ | $CH_2OH$ | O | 3 | Colorless oil | 54 |
| 109 | $Ph(CH_2)_2$ | c-$Ph(CH_2)_2$ | H | $CF_3$ | H | O | 3 | Colorless oil | 13 |
| 110 | $Ph(CH_2)_2$ | c-$Ph(CH_2)_2$ | H | Cl | $CH_2OH$ | O | 3 | Colorless oil | 61 |
| 111 | $Ph(CH_2)_2$ | c-$Ph(CH_2)_2$ | H | Cl | H | O | 3 | Colorless oil | 10 |
| 112 | i-PrO | c-iPr | H | Cl | $CH_2OH$ | O | 3 | Colorless oil | 82 |
| 113 | i-PrO | c-iPr | H | Cl | H | O | 3 | Colorless oil | 7 |
| 114 | PhO | H | H | Cl | $CH_2OH$ | O | 3 | Colorless oil | 76 |
| 115 | PhO | H | H | Cl | H | O | 3 | Colorless oil | 17 |
| 116 | $PhCH_2O$ | H | H | H | $CH_2OH$ | O | 3 | Colorless oil | 76 |
| 117 | $PhCH_2O$ | H | H | H | H | O | 3 | Colorless oil | 11 |
| 118 | $PhCH_2O$ | H | H | Br | $CH_2OH$ | O | 3 | Colorless oil | 61 |
| 119 | $PhCH_2O$ | H | H | Br | H | O | 3 | Colorless oil | 11 |
| 120 | $PhCH_2O$ | H | H | SMe | $CH_2OH$ | O | 3 | Colorless oil | (38) |
| 121 | $PhCH_2O$ | H | H | SMe | H | O | 3 | Colorless oil | (10) |

Numbers in parentheses are cumulative yields from the previous step.

TABLE 9

| Examples | R1 | R2 | R3 | R4 | R5 | X | n | Characteristics | Yield (%) |
|---|---|---|---|---|---|---|---|---|---|
| 122 | $PhCH_2O$ | H | H | Me | $CH_2OH$ | O | 3 | Colorless oil | 75 |
| 123 | $PhCH_2O$ | H | H | Me | H | O | 3 | Colorless oil | 11 |
| 124 | $PhCH_2O$ | H | H | Et | $CH_2OH$ | O | 3 | Colorless oil | 61 |
| 125 | $PhCH_2O$ | H | H | Et | H | O | 3 | Colorless oil | 8 |
| 126 | $PhCH_2O$ | H | H | Cl | $CH_2OH$ | S | 2 | Colorless powder | 41 |
| 127 | $PhCH_2O$ | H | H | Cl | H | S | 2 | Pale yellow oil | 11 |
| 128 | $PhCH_2O$ | H | H | Cl | $CH_2OH$ | S | 3 | Colorless powder | 65 |
| 129 | $PhCH_2O$ | H | H | Cl | H | S | 3 | Colorless oil | 26 |
| 130 | $PhCH_2O$ | H | H | Cl | $CH_2OH$ | S | 4 | Colorless oil | 76 |
| 131 | $PhCH_2O$ | H | H | Cl | H | S | 4 | Colorless oil | 15 |
| 132 | $PhCH_2O$ | c-$CF_3$ | H | H | $CH_2OH$ | O | 3 | Colorless oil | 83 |
| 133 | $PhCH_2O$ | c-$CF_3$ | H | H | H | O | 3 | Colorless oil | 10 |
| 134 | Cl | H | H | H | $CH_2OH$ | S | 3 | Colorless oil | 41 |
| 135 | Cl | H | H | H | H | S | 3 | Colorless oil | 31 |
| 136 | $CF_3$ | c-$CF_3$ | H | Cl | $CH_2OH$ | S | 3 | Colorless amorphous | 66 |
| 137 | $CF_3$ | c-$CF_3$ | H | Cl | H | S | 3 | Colorless oil | 13 |
| 138 | Et | H | H | H | $CH_2OH$ | O | 3 | Colorless oil | 76 |
| 139 | Et | H | H | H | H | O | 3 | Colorless oil | 13 |
| 140 | SOMe | H | H | H | $CH_2OH$ | O | 3 | Colorless oil | 67 |
| 141 | SOMe | H | H | H | H | O | 3 | Colorless oil | 27 |
| 142 | Cl | c-Cl | H | H | $CH_2OH$ | O | 1 | Colorless amorphous | 56 |
| 143 | Cl | c-Cl | H | H | H | O | 1 | Colorless powder | 24 |
| 144 | $CF_3$ | H | H | $PhCH_2O$ | $CH_2OH$ | O | 3 | Colorless oil | 64 |
| 145 | $CF_3$ | H | H | $PhCH_2O$ | H | O | 3 | Colorless oil | 5 |

TABLE 9-continued

| Examples | R1 | R2 | R3 | R4 | R5 | X | n | Characteristics | Yield (%) |
|---|---|---|---|---|---|---|---|---|---|
| 146 | PhCH$_2$O | H | H | Cl | CH$_2$OH | O | 3 | Colorless oil | 77 |
| 147 | PhCH$_2$O | H | H | Cl | H | O | 3 | Colorless oil | 19 |
| 148 | CF$_3$ | H | Cl | H | CH$_2$OH | O | 3 | Colorless oil | 58 |
| 149 | CF$_3$ | H | H | Cl | CH$_2$OH | O | 3 | Colorless oil | 68 |
| 150 | PhCH$_2$O | H | H | F | CH$_2$OH | O | 3 | Colorless oil | 34 |
| 151 | CF$_3$ | a-Cl | H | H | CH$_2$OH | O | 3 | Colorless oil | 57 |
| 152 | CF$_3$ | c-Cl | H | H | CH$_2$OH | O | 3 | Colorless oil | 51 |
| 153 | CF$_3$ | d-Cl | H | H | CH$_2$OH | O | 3 | Colorless oil | 37 |
| 154 | Ph(CH$_2$)$_2$ | c-CF$_3$ | H | H | CH$_2$OH | O | 3 | Colorless oil | 46 |
| 155 | PhCH$_2$O | H | H | Cl | CH$_2$OH | O | 2 | Colorless powder | (49) |
| 156 | PhCH$_2$O | H | H | Cl | CH$_2$OH | O | 4 | Colorless oil | (72) |
| 157 | CF$_3$ | H | H | F | CH$_2$OH | O | 3 | Colorless oil | 63 |
| 158 | PhCH$_2$O | c-PhCH$_2$O | H | H | CH$_2$OH | O | 3 | Colorless oil | (45) |
| 159 | PhCH$_2$O | c-PhCH$_2$O | H | Cl | CH$_2$OH | O | 3 | Colorless oil | (17) |
| 160 | PhCH$_2$O | c-Cl | H | Cl | CH$_2$OH | O | 3 | Colorless oil | 61 |
| 161 | PhCH$_2$O | H | H | CF$_3$ | CH$_2$OH | O | 3 | Colorless oil | 83 |
| 162 | PhCH$_2$O | H | H | Ph | CH$_2$OH | O | 3 | Colorless oil | (50) |
| 163 | MeS | H | H | H | CH$_2$OH | O | 3 | Colorless powder | 56 |
| 164 | n-C$_5$H$_{11}$ | H | H | H | CH$_2$OH | O | 3 | Colorless oil | 98 |
| 165 | c-C$_7$H$_{18}$ | H | H | H | CH$_2$OH | O | 3 | Colorless oil | 90 |
| 166 | iPr | c-iPrO | H | H | CH$_2$OH | O | 3 | Colorless oil | 72 |
| 167 | iPr | c-iPr | H | Cl | CH$_2$OH | O | 3 | Colorless oil | 33 |
| 168 | PhCH$_2$S | H | H | H | CH$_2$OH | O | 3 | Colorless oil | (20) |

Numbers in parentheses are cumulative yields from the previous step.

TABLE 10

| Examples | R1 | R2 | R3 | R4 | R5 | X | n | Characteristics | Yield (%) |
|---|---|---|---|---|---|---|---|---|---|
| 169 | PhCH$_2$S | H | H | Cl | CH$_2$OH | O | 3 | Colorless oil | (11) |
| 170 | i-Bu | H | H | H | CH$_2$OH | O | 3 | Colorless oil | 92 |
| 171 | PhOCH$_2$ | H | H | H | CH$_2$OH | O | 3 | Colorless oil | 64 |
| 172 | PhCH$_2$O | H | H | i-Pr | CH$_2$OH | O | 3 | Colorless oil | (62) |
| 173 | CF$_3$ | H | H | H | CH$_2$OH | S | 3 | Colorless powder | 89 |
| 174 | CF$_3$ | H | H | H | CH$_2$OH | SO | 3 | Colorless amorphous | 71 |
| 175 | CF$_3$ | H | H | CF$_3$ | CH$_2$OH | S | 3 | Colorless oil | 51 |
| 176 | CF$_3$ | c-Me | H | H | CH$_2$OH | S | 3 | Colorless powder | 81 |
| 177 | CF$_3$ | c-Me | H | H | CH$_2$OH | SO | 3 | Colorless powder | 65 |
| 178 | MeO | H | H | Cl | CH$_2$OH | S | 3 | Colorless oil | 56 |
| 179 | PhCH$_2$O | H | H | H | CH$_2$OH | S | 3 | Colorless oil | (45) |
| 180 | PhCH$_2$O | H | H | CF$_3$ | CH$_2$OH | S | 3 | Colorless oil | 66 |
| 181 | Cl | c-Cl | H | H | CH$_2$OH | O | 3 | Colorless oil | 50 |
| 182 | Cl | c-Cl | H | H | H | O | 3 | Colorless oil | 13 |
| 183 | MeSO$_2$ | H | H | H | CH$_2$OH | O | 3 | Colorless amorphous | 78 |
| 184 | i-PrO | H | H | H | CH$_2$OH | O | 3 | Colorless oil | 68 |

Numbers in parentheses are cumulative yields from the previous step.

Example 185

5-[4-(3-benzyloxyphenoxy)-2-chlorophenyl]-2-t-butoxycarbonylamino-2-methoxymethylpentane-1-ol

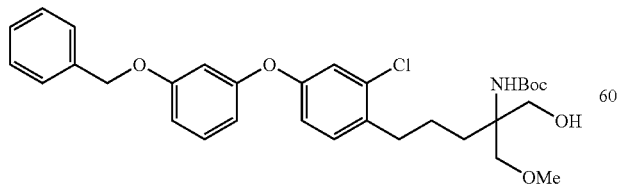

The compound of Example 146 (720 mg) was dissolved in acetonitrile (20 mL). To this solution, Ag$_2$O (1.85 g) and MeI (3 mL) were added and the mixture was stirred for 7 days at room temperature. Subsequently, the mixture was filtered through Celite and the filtrate was concentrated and purified on a silica gel column chromatography (hexane:ethyl acetate=3:1). This gave the desired product as a colorless oil (310 mg).

FABMS: 556([M+H]$^+$).

$^1$H-NMR(400 MHz, CDCl$_3$) δ 1.43(9H, s), 1.48-1.81(4H, m), 2.68(2H, t, J=7.8 Hz), 3.33(1H, d, J=8.8 Hz), 3.36(3H, s), 3.57(1H, d, 8.8 Hz), 3.65(2H, d, J=6.8 Hz), 5.03(2H, s), 5.10(1H, br s), 6.59-6.62(2H, m), 6.74(1H, dd, J=8.3, 2.4 Hz), 6.84(1H, dd, J=8.3, 2.4 Hz), 7.00(1H, d, J=2.4 Hz), 7.15(1H, d, J=8.3 Hz), 7.23(1H, t, J=8.3 Hz), 7.33-7.42(5H, m).

Example 186

2-t-butoxycarbonylamino-2-methoxymethyl-5-[4-(3-trifluoromethylphenoxy)phenyl]pentane-1-ol

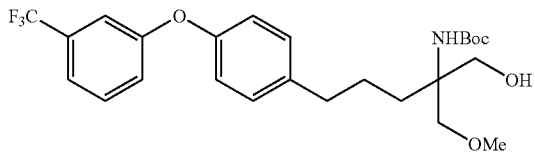

In a similar manner to Example 185, the compound of Example 82 was reacted to obtain the desired product as a colorless oil.

FABMS: 484([M+H]$^+$).

$^1$H-NMR(400 MHz, CDCl$_3$) δ 1.42(9H, s), 1.48-1.83(4H, m), 2.57-2.65(2H, m), 3.33(1H, d, J=8.8 Hz), 3.37(3H, s), 3.58(1H, d, 8.8 Hz), 3.62(2H, br s), 5.07(1H, br s), 6.94(2H, d, J=6.4 Hz), 7.10-7.21(4H, m), 7.30(1H, d, J=7.8 Hz), 7.40 (1H, t, J=7.8 Hz).

Example 187

4-[4-(3-benzyloxyphenylthio)-2-chlorophenyl]propyl-4-hydroxymethyl-2-oxazolidinone

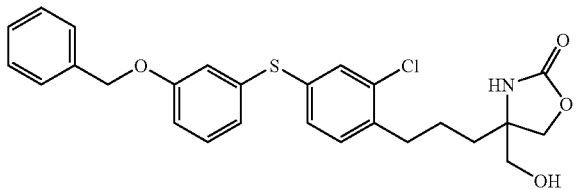

The compound of Example 128 (3.30 g) was dissolved in THF (80 mL). While this solution was kept at 0° C., 60% sodium hydride (600 mg) was added and the mixture was stirred for 24 hours at room temperature. Subsequently, ice water was added and the mixture was extracted with ethyl acetate. The extract was washed sequentially with water and a saturated aqueous solution of sodium chloride. The organic phase was then dried over anhydrous sodium sulfate. The solvent was removed by distillation and the residue was purified on a silica gel column chromatography (hexane:ethyl acetate=1:1 then 100% ethyl acetate) to give the desired product as a pale yellow oil (2.37 g).

$^1$H-NMR(400 MHz, CDCl$_3$) δ 1.63-1.72(4H, m), 2.74(2H, t, J=6.8 Hz), 3.51(1H, d, J=11.2 Hz), 3.58(1H, d, J=11.2 Hz), 4.09(1H, d, J=8.8 Hz), 4.24(1H, d, J=8.8 Hz), 5.02(2H, s), 5.28(1H, br s), 6.87-6.90(1H, m), 6.94-7.00(2H, m), 7.09-7.16(2H, m), 7.22-7.52(7H, m).

Example 188

4-[4-(3-benzyloxyphenylthio)-2-chlorophenyl]propyl-4-iodomethyl-2-oxazolidinone

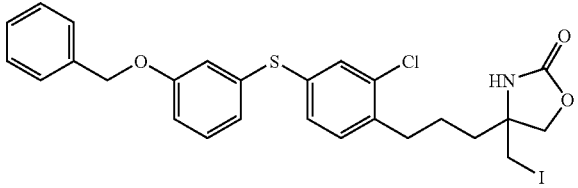

The compound of Example 187 (2.37 g) was dissolved in pyridine (30 mL). To this solution, p-toluenesulfonylchloride (1.33 g) was added and the mixture was stirred for 24 hours at room temperature and a further 5 hours at 60° C. Following addition of water, the mixture was extracted with ethyl acetate. The extract was then washed sequentially with water, diluted hydrochloric acid and a saturated aqueous solution of sodium chloride. The organic phase was dried over anhydrous sodium sulfate. The solvent was removed by distillation and the residue was purified on a silica gel chlomatography (hexane:ethyl acetate=1:1) to obtain a sulfonic acid ester as a colorless oil (2.14 g). The sulfonic acid ester (2.14 g) was dissolved in acetone (20 mL), followed by addition of sodium iodide (2.55 g) and refluxing for 10 hours. Subsequently, water was added and the mixture was extracted with ethyl acetate. The extract was washed sequentially with water and a saturated aqueous solution of sodium chloride. The organic phase was then dried over anhydrous sodium sulfate. The solvent was removed by distillation and the residue was purified on a silica gel chlomatography (hexane:ethyl acetate=1:1) to give the desired product as a colorless oil (1.47 g).

$^1$H-NMR(400 MHz, CDCl$_3$) δ 1.59-1.65(2H, m), 1.83-1.89(2H, m), 2.75(2H, t, J=7.8 Hz), 3.31(2H, s), 4.19(1H, d, J=9.3 Hz), 4.21(1H, d, J=9.3 Hz), 5.02(2H, s), 5.13(1H, br s), 6.88(1H, dd, J=7.8, 2.0 Hz), 6.94-7.00(2H, m), 7.11(1H, d, J=7.8 Hz), 7.16(1H, dd, J=7.8, 2.0 Hz), 7.22-7.41(7H, m).

Example 189

4-[4-(3-benzyloxyphenylthio)-2-chlorophenyl]propyl-4-methylthiomethyl-2-oxazolidinone

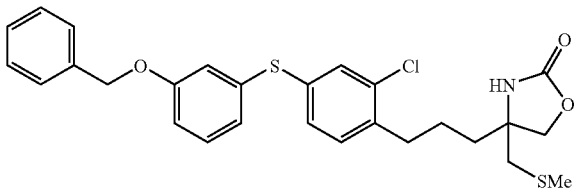

The compound of Example 188 (1.47 g) was dissolved in THF (30 mL). To this solution, NaSMe (210 mg) was added and the mixture was stirred for 2 hours at room temperature. Following addition of water, the mixture was extracted with ethyl acetate. The extract was then washed with a saturated aqueous solution of sodium chloride and the organic phase was dried over anhydrous sodium sulfate. The solvent was concentrated under reduced pressure to give the desired product as a colorless oil (1.27 g).

FABMS: 514([M+H]$^+$).

$^1$H-NMR(400 MHz, CDCl$_3$) δ 1.62-1.77(4H, m), 2.17(3H, s), 2.68(1H, d, J=13.2 Hz), 2.74(2H, t, J=7.3 Hz), 2.78(1H, d, J=13.2 Hz), 4.15(1H, d, J=9.0 Hz), 4.20(1H, d, J=9.0 Hz), 5.03(2H, s), 5.22(1H, br s), 6.87-6.90(1H, m), 6.93-6.97(2H, m), 7.10-7.17(2H, m), 7.22-7.41(7H, m).

Example 190

5-[4-(3-benzyloxyphenylthio)-2-chlorophenyl]-2-t-butoxycarbonylamino-2-methylthiomethylpentane-1-ol

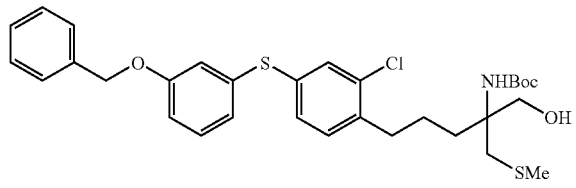

The compound of Example 189 (1.27 g) was dissolved in acetonitrile (20 mL). To this solution, Boc$_2$O (1.09 g) and dimethylaminopyridine (100 mg) were added and the mixture was stirred for 30 min at room temperature. The solvent was removed under reduced pressure and the residue was purified on a silica gel chlomatography (hexane:ethyl acetate=4:1) to obtain an N-Boc-oxazolidinone as a colorless oil (1.48 g). This product was dissolved in methanol (20 mL), followed by addition of cesium carbonate (410 mg) and stirring overnight at room temperature. Subsequently, the solvent was removed by distillation and the residue was dissolved in ethyl acetate. The mixture was then washed sequentially with diluted hydrochloric acid and water and the organic phase was dried over anhydrous sodium sulfate. The solvent was removed by distillation and the residue was purified on a silica gel chlomatography (hexane:ethyl acetate=2:1) to give the desired product as a colorless oil (1.28 g).

FABMS: 588([M+H]$^+$).

$^1$H-NMR(400 MHz, CDCl$_3$) δ 1.43(9H, s), 1.51-1.66(3H, m), 1.82-1.85(1H, m), 2.15(3H, s), 2.69(2H, t, J=7.3 Hz), 2.75(1H, d, J=13.4 Hz), 2.90(1H, d, J=13.4 Hz), 3.69-3.70 (2H, m), 4.02(1H, br), 4.99(1H, br s), 5.02(2H, s), 6.86-6.94 (3H, m), 7.12-7.17(2H, m), 7.21-7.41(7H, m).

Example 191

5-[4-(3-benzyloxyphenoxy)-2-chlorophenyl]-2-t-butoxycarbonylamino-2-t-butyldiphenylsiloxymethylpentane-1-ol

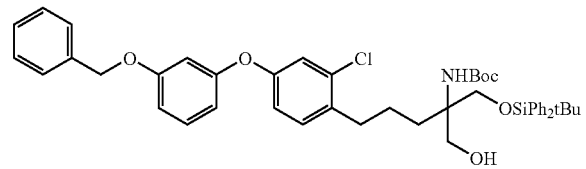

The compound of Example 146 (3.25 g) was dissolved in DMF (18 mL). To this solution, diisopropylethylamine (10.5 mL) and t-BuPh$_2$SiCl (1.73 g) were added and the mixture was stirred for 8 hours at room temperature. Subsequently, ice water was added and the mixture was extracted with ethyl acetate. The extract was washed sequentially with water, diluted hydrochloric acid, water and a saturated aqueous solution of sodium chloride. The organic phase was then dried over anhydrous sodium sulfate. The solvent was removed by distillation and the residue was purified on a silica gel column chromatography (hexane:ethyl acetate=7:1) to give the desired product as a colorless oil (1.64 g).

$^1$H-NMR(400 MHz, CDCl$_3$)δ 1.06(9H, s), 1.43(9H, s), 1.49-1.82(4H, m), 2.66(2H, t, J=7.8 Hz), 3.54(1H, d, J=10.3 Hz), 3.65-3.67(2H, m), 3.74(1H, d, J=10.3 Hz), 5.03(2H, s), 5.05(1H, br s), 6.59(1H, dd, J=8.3, 2.4 Hz), 6.63(1H, t, J=2.4 Hz), 6.74(1H, dd, J=8.3, 2.4 Hz), 6.82(1H, dd, J=8.3, 2.4 Hz), 6.99(1H, d, J=2.4 Hz), 7.10(1H, d, J=8.3 Hz), 7.23(1H, t, J=8.3 Hz), 7.31-7.45(11H, m), 7.61-7.64(4H, m).

Example 192

5-[4-(3-benzyloxyphenoxy)-2-chlorophenyl]-2-t-butoxycarbonylamino-2-t-butyldiphenylsiloxymethylpentanal

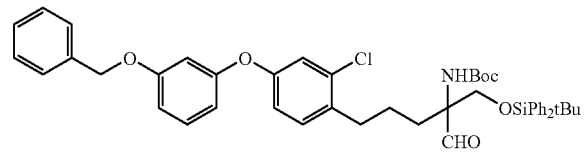

The compound of Example 191 (940 mg) was dissolved in DMF (10 mL). To this solution, pyridinium dichromate (800 mg) was added and the mixture was stirred for 48 hours at room temperature. Following addition of water, the mixture was extracted with ethyl acetate. The extract was then washed sequentially with water and a saturated aqueous solution of sodium chloride. The organic phase was dried over anhydrous sodium sulfate. The solvent was concentrated and the residue was purified on a silica gel chlomatography (hexane:ethyl acetate=3:1) to give the desired product as a colorless oil (710 mg).

$^1$H-NMR(400 MHz, CDCl$_3$)δ 1.01(9H, s), 1.44(9H, s), 1.49-1.73(4H, m), 2.64(2H, br s), 3.84(1H, d, J=10.3 Hz), 4.13(1H, d, J=10.3 Hz), 5.03(2H, s), 5.43(1H, br s), 6.58(1H, dd, J=8.3, 2.4 Hz), 6.62(1H, t, J=2.4 Hz), 6.74(1H, dd, J=8.3, 2.4 Hz), 6.82(1H, dd, J=8.3, 2.4 Hz), 6.99(1H, d, J=2.4 Hz), 7.08(1H, d, J=8.3 Hz), 7.23(1H, t, J=8.3 Hz), 7.30-7.43(11H, m), 7.56-7.64(4H, m), 9.36(1H, s).

Example 193

5-[4-(3-benzyloxyphenylthio)-2-chlorophenyl]-2-t-butoxycarbonylaminopentanal

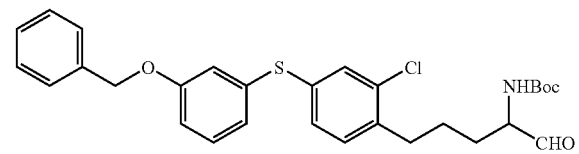

To an oxalyl chloride solution (1.0 mL) of methylene chloride (20 mL), a mixture of DMSO (1.7 mL) and methylene chloride (10 mL) was added while the mixtures were kept at −78° C. The compound of Example 129 (5.59 g) in methylene chloride (20 mL) was then added dropwise. After 15 min, triethylamine (7.2 mL) was added and the mixture was stirred for 2 hours until room temperature. Following addition of water, the mixture was extracted with ethyl acetate and the organic phase was dried over anhydrous sodium sulfate. The solvent was then concentrated and the residue was purified on a silica gel chlomatography (hexane:ethyl acetate=3:1) to give the desired product as a pale yellow oil (4.75 g).

$^1$H-NMR(400 MHz, CDCl$_3$) δ 1.44(9H, s), 1.60-1.74(3H, m), 1.96(1H, br), 2.72-2.77(2H, m), 4.28(1H, br), 5.02(2H, s), 6.87-6.95(3H, m), 7.10-7.16(2H, m), 7.23(1H, t, J=7.8 Hz), 7.28-7.52(5H, m), 9.58(1H, s).

Example 194

Ethyl 5-[4-(3-benzyloxyphenylthio)-2-chlorophenyl]-2-ethoxycarbonyl-2-methylpentanoate

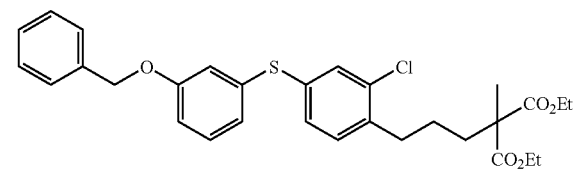

Sodium hydride (242 mg) was dissolved in DMF (5 mL). To this solution, diethyl methylmalonate (0.956 mL) was added and the mixture was stirred for 30 min. The compound of Reference Example 252 (2.50 g) in DMF (5 mL) was then added and the mixture was further stirred for 1 hour. Subsequently, the reaction mixture was diluted with water and was extracted with ethyl acetate. The ethyl acetate layer was washed with a saturated aqueous solution of sodium chloride and was dried over anhydrous sodium sulfate. The dried organic phase was concentrated and the resulting residue was purified on a silica gel chlomatography (hexane:ethyl acetate=20:1 to 10:1) to give the desired product as a yellow oil (2.74 g).

MS (EI): 540( [M]$^+$).

$^1$H-NMR(400MHz, CDCl$_3$) δ 1.23(6H, t, J=7.3 Hz), 1.40 (3H, s), 1.52-1.60(2H, m), 1.91-1.95(2H, m), 2.70(2H, t, J=7.9 Hz), 4.16(4H, q, J=7.3 Hz), 5.02(2H, s), 6.86-6.94(3H, m), 7.11-7.14(2H, m), 7.20-7.24(1H, m), 7.31-7.40(6H, m).

Example 195

Ethyl 5-[4-(3-benzyloxyphenylthio)-2-chlorophenyl]-2-ethoxycarbonyl-2-ethylpentanoate

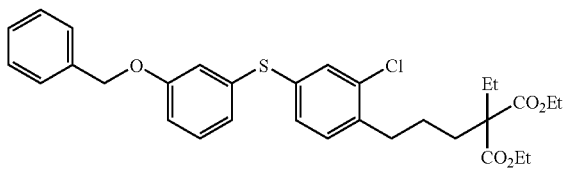

Using diethyl ethylmalonate, the reaction was carried out in the same manner as in Reference Example 194 to give the desired product as a yellow oil.

MS(EI): 554([M]+).

$^1$H-NMR(400 MHz, CDCl$_3$) δ 0.80(3H, t, J=7.3 Hz), 1.22 (6H, t, J=7.3 Hz), 1.45-1.53(2H, m), 1.89-1.97(4H, m), 2.70 (2H, t, J=7.3 Hz), 4.16(4H, q, J=7.3 Hz), 5.02(2H, s), 6.86-6.94(3H, m), 7.11-7.16(2H, m), 7.20-7.24(1H, m), 7.31-7.40 (6H, m).

Example 196

Ethyl 4-[4-(3-benzyloxyphenylthio)-2-chlorophenyl]-2-ethoxycarbonyl-2-methylbutyrate

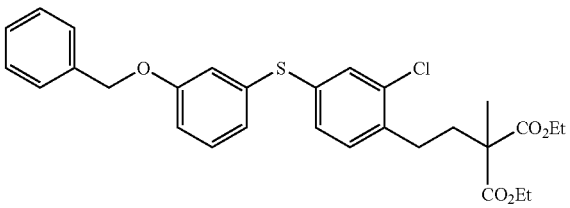

Using the compound of Reference Example 317, the reaction was carried out in the same manner as in Example 194 to give the desired product as a pale yellow oil.

MS(EI): 526([M]+).

$^1$H-NMR(400 MHz, CDCl$_3$) δ 1.27(6H, t, J=7.3 Hz), 1.52 (3H, s), 2.10-2.14(2H, m), 2.65-2.69(2H, m), 4.20(4H, q, J=7.3 Hz), 5.02(2H, s), 6.86-6.96(3H, m), 7.15(2H, s), 7.23 (1H, t, J=8.0), 7.31-7.41(6H, m).

Example 197

Ethyl 4-[4-(3-benzyloxyphenylthio)-2-chlorophenyl]-2-ethoxycarbonyl-2-ethylbutyrate

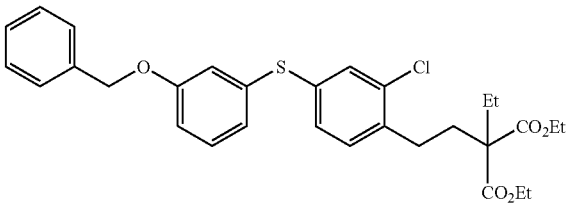

Using the compound of Reference Example 317, the reaction was carried out in the same manner as in Example 195 to give the desired product as a colorless oil.

MS(EI): 540( [M]+).

$^1$H-NMR(400 MHz, CDCl$_3$) δ 0.82(3H, t, J=7.3 Hz), 1.17 (6H, t, J=7.3 Hz), 1.93(2H, q, J=7.3 Hz), 1.98-2.02(2H, m), 2.45-2.51(2H, m), 4.13(4H, q, J=7.3 Hz), 5.10(2H, s), 6.92-7.01(3H, m), 7.21(1H, dd, J=8.0, 1.9 Hz), 7.30-7.41(8H, m).

Example 198

5-[4-(3-benzyloxyphenylthio)-2-chlorophenyl]-2-ethoxycarbonyl-2-methylpentanoic acid

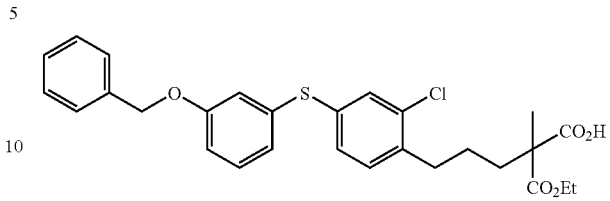

The compound of Example 194 (2.74 g) was dissolved in ethanol (10 mL). To this solution, potassium hydroxide (330 mg) was added and the mixture was stirred overnight at 50° C. Subsequently, the reaction mixture was diluted with water, followed by addition of 2 mol/L hydrochloric acid and extraction with ethyl acetate. The ethyl acetate layer was washed with a saturated aqueous solution of sodium chloride, was dried over anhydrous magnesium sulfate, and was then concentrated. The resulting residue was purified on a silica gel chlomatography (hexane:ethyl acetate=10:1 to 2:1) to give the desired product as a yellow oil (2.38 g).

MS(EI): 512([M]+).

$^1$H-NMR(400MHz, CDCl$_3$) δ 1.26(3H, t, J=7.3 Hz), 1.47 (3H, s), 1.53-1.62(2H, m), 1.92-2.03(2H, m), 2.71(2H, t, J=7.9 Hz), 4.22(2H, q, J=7.3 Hz), 5.02(2H, s), 6.87-6.94(3H, m), 7.10-7.14(2H, m), 7.21-7.25(1H, m), 7.31-7.40(6H, m).

Example 199

5-[4-(3-benzyloxyphenylthio)-2-chlorophenyl]-2-ethoxycarbonyl-2-ethylpentanoic acid

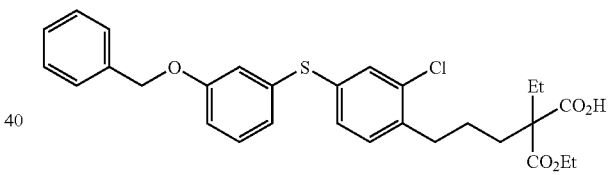

Using the compound of Example 195, the reaction was carried out in the same manner as in Example 198 to give the desired product as a yellow oil.

MS(EI): 526([M]+).

$^1$H-NMR(400 MHz, CDCl$_3$) δ 0.84(3H, t, J=7.3 Hz), 1.28 (3H, t, J=7.3 Hz), 1.42-1.59(2H, m), 1.85-1.95(2H, m), 2.00-2.13(2H, m), 2.66-2.70(2H, m), 4.23-4.31(2H, m), 5.02(2H, s), 6.86-6.94(3H, m), 7.08-7.15(2H, m), 7.21-7.25(1H, m), 7.30-7.40(6H, m).

Example 200

4-[4-(3-benzyloxyphenylthio)-2-chlorophenyl]-2-ethoxycarbonyl-2-methylbutyric acid

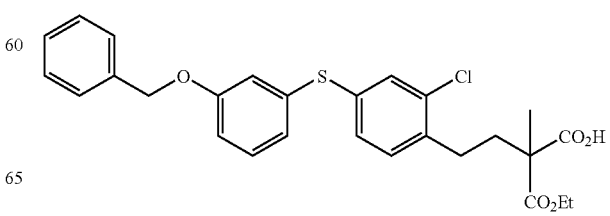

Using the compound of Example 196, the reaction was carried out in the same manner as in Example 198 to give the desired product as a pale yellow oil.

MS(EI): 499( [M]+).

$^{1}$H-NMR(400 MHz, CDCl$_{3}$) δ 1.30(3H, t, J=7.3 Hz), 1.57 (3H, s), 2.11-2.19(2H, m), 2.69(2H, t, J=8.5 Hz), 4.24(2H, q, J=7.3 Hz), 5.02(2H, s), 6.87-6.96(3H, m), 7.14(2H, s), 7.23 (1H, t, J=8.0 Hz), 7.31-7.40(6H, m).

Example 201

4-[4-(3-benzyloxyphenylthio)-2-chlorophenyl]-2-ethoxycarbonyl-2-ethylbutyric acid

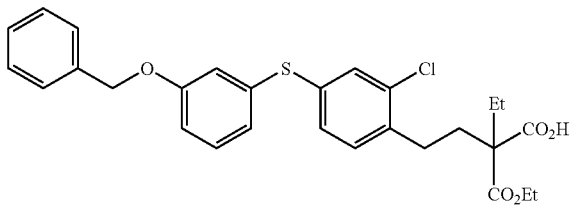

Using the compound of Example 197, the reaction was carried out in the same manner as in Example 198 to give the desired product as a pale yellow oil.

$^{1}$H-NMR(400 MHz, CDCl$_{3}$) δ 0.90(3H, t, J=7.3 Hz), 1.33 (3H, t, J=7.3 Hz), 1.94-1.99(1H, m), 2.05-2.12(1H, m), 2.19-2.24(2H, m), 2.59-2.64(2H, m), 4.20-4.31(2H, m), 5.02(2H, s), 6.87-6.94(3H, m), 7.09-7.14(2H, m), 7.23(1H, t, J=8.0 Hz), 7.29-7.40(6H, m).

Example 202

Ethyl 5-[4-(3-benzyloxyphenylthio)-2-chlorophenyl]-2-methoxycarbonylamino-2-methylpentanoate

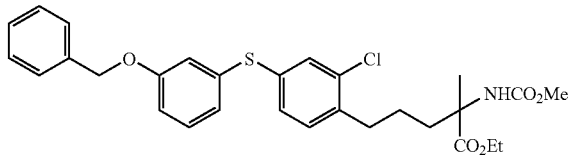

The compound of Example 198 (2.38 g) was dissolved in benzene (20 mL). To this solution, triethylamine (0.711 mL) and DPPA (1.10 mL) were added. The mixture was then stirred for 10 min at room temperature and for a further 1 hour and 30 min while being refluxed. Subsequently, methanol (3.76 mL) was added over 30 min and the mixture was stirred overnight. The reaction mixture was diluted with water and was extracted with ethyl acetate. The ethyl acetate layer was washed with a saturated aqueous solution of sodium chloride and was dried over anhydrous magnesium sulfate. The dried organic phase was concentrated and the resulting residue was purified on a silica gel chlomatography (hexane:ethyl acetate=20:1 to 10:1) to give the desired product as a yellow oil (2.04 g).

MS(EI): 541([M]+).

$^{1}$H-NMR(400 MHz, CDCl$_{3}$) δ 1.24(3H, t, J=7.3 Hz), 1.36-1.40(1H, m), 1.54(3H, s), 1.56-1.65(1H, m), 1.80-1.87(1H, m), 2.28(1H, m), 2.65-2.69(2H, m), 3.63(3H, m), 4.15-4.22 (2H, m), 5.02(2H, s), 5.61(1H, br s), 6.86-6.94(3H, m), 7.09-7.15(2H, m), 7.20-7.24(1H, m), 7.31-7.40(6H, m).

Example 203

Ethyl 5-[4-(3-benzyloxyphenylthio)-2-chlorophenyl]-2-ethyl-2-methoxycarbonylaminopentanoate

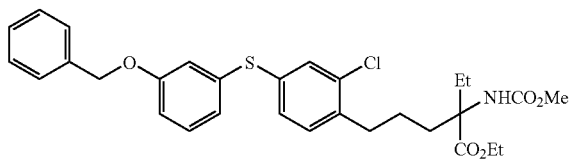

Using the compound of Example 199, the reaction was carried out in the same manner as in Example 202 to obtain the desired product as a yellow oil.

MS(EI): 555([M]+).

$^{1}$H-NMR(400 MHz, CDCl$_{3}$) δ 0.74(3H, t, J=7.3 Hz), 1.24 (3H, t, J=7.3 Hz), 1.28-1.32(1H, m), 1.57-1.58(1H, m), 1.70-1.84(2H, m), 2.34-2.44(2H, m), 2.62-2.72(2H, m), 3.63(3H, s), 4.16-4.22(2H, m), 5.02(2H, s), 5.78(1H, br s), 6.86-6.94 (3H, m), 7.08-7.15(2H, m), 7.20-7.24(1H, m), 7.31-7.40(6H, m).

Example 204

Ethyl 4-[4-(3-benzyloxyphenylthio)-2-chlorophenyl]-2-t-butoxycarbonylamino-2-methylbutyrate

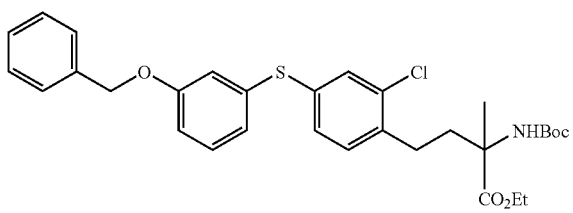

Using the compound of Example 200 and t-butanol instead of methanol, the reaction was carried out in the same manner as in Example 202 to obtain the desired product as a pale yellow oil.

FABMS: 569([M+H]+).

$^{1}$H-NMR(400 MHz, CDCl$_{3}$) δ 1.29(3H, t, J=7.3 Hz), 1.46 (9H, s), 1.58(3H, s), 2.10(1H, td, J=13.0, 4.9 Hz), 2.41(1H, br), 2.53(1H, td, J=13.0, 4.9 Hz), 2.67(1H, td, J=13.0, 4.9 Hz), 4.19(2H, q, J=7.3 Hz), 5.02(2H, s), 5.46(1H, br s), 6.86-6.94 (3H, m), 7.08-7.15(2H, m), 7.23(1H, t, J=8.0 Hz), 7.30-7.40 (6H, m).

Example 205

Ethyl 4-[4-(3-benzyloxyphenylthio)-2-chlorophenyl]-2-ethyl-2-methoxycarbonylaminobutyrate

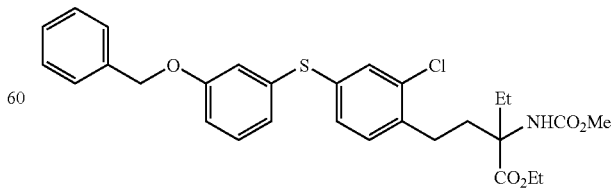

Using the compound of Example 201, the reaction was carried out in the same manner as in Example 202 to obtain the desired product as a pale yellow oil.

MS(EI): 541([M]⁺).

¹H-NMR(400 MHz, CDCl₃) δ 0.77(3H, t, J=7.3 Hz), 1.30 (3H, t, J=7.3 Hz), 1.75-1.80(1H, m), 2.05-2.15(1H, m), 2.36-2.49(2H, m), 2.59-2.68(2H, m), 3.66(3H, s), 4.11-4.27(2H, m), 5.02(2H, s), 5.87(1H, br), 6.86-6.93(3H, m), 7.08-7.14 (2H, m), 7.22(1H, t, J=8.0 Hz), 7.30-7.40(6H, m).

Example 206

5-[4-(3-benzyloxyphenylthio)-2-chlorophenyl]-2-methoxycarbonylamino-2-methylpentane-1-ol

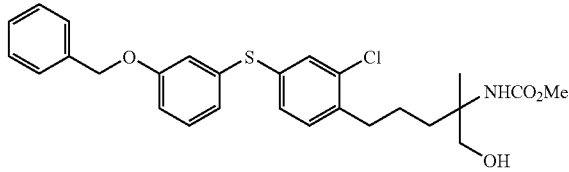

Using the compound of Example 202, the reaction was carried out in the same manner as in Example 76 to obtain the desired product as a colorless oil.

MS(EI): 499([M]⁺).

¹H-NMR(400 MHz, CDCl₃) δ 1.18(3H, s), 1.57-1.84(4H, m), 2.71(2H, t, J=7.3 Hz), 3.59-3.69(3H, m), 3.63(3H, s), 4.71(1H, br s), 5.02(2H, s), 6.86-6.94(3H, m), 7.13-7.17(2H, m), 7.21-7.25(1H, m), 7.30-7.41(6H, m).

Examples 207 and 208

(+) and (−)-5-[4-(3-benzyloxyphenylthio)-2-chlorophenyl]-2-methoxycarbonylamino-2-methylpentane-1-ols The compound of Example 206 was optically resolved by a high performance liquid chromatography (HPLC) (chiralcel OD, hexane:isopropanol=70:30, detection wavelength=UV 254 nm, flow rate=3 mL/min).

The compound obtained from the first eluate had an optical rotation [α]²⁴·⁰_D of +15° (C=1.0, chloroform) (Example 207), while the compound obtained from the second eluate had an optical rotation [α]²⁴·⁷_D of −12° (C=1.0, chloroform) (Example 208).

Example 209

5-[4-(3-benzyloxyphenylthio)-2-chlorophenyl]-2-ethyl-2-methoxycarbonylaminopentane-1-ol

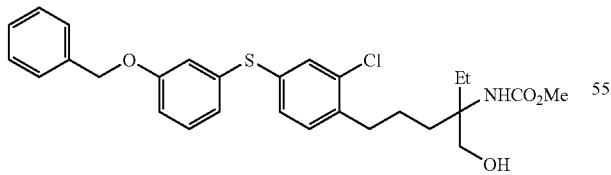

Using the compound of Example 203, the reaction was carried out in the same manner as in Example 76 to obtain the desired compound as a pale yellow oil.

MS(EI): 513([M]⁺).

¹H-NMR(400 MHz, CDCl₃) δ 0.83(3H, t, J=7.3 Hz), 1.51-1.73(6H, m), 2.70(2H, t, J=7.3 Hz), 3.63(3H, s), 3.65-3.70 (3H, m), 4.63(1H, br s), 5.02(2H, s), 6.86-6.94(3H, m), 7.12-7.17(2H, m), 7.20-7.24(1H, m), 7.30-7.40(6H, m).

Examples 210 and 211

(+) and (−)-5-[4-(3-benzyloxyphenylthio)-2-chlorophenyl]-2-ethyl-2-methoxycarbonylaminopentane-1-ols The compound of Example 209 was optically resolved by HPLC (chiralcel OD, hexane:isopropanol=60:40, detection wavelength=UV 254 nm, flow rate=3 mL/min).

The colorless oil obtained from the first eluate had an optical rotation [α]²⁵·⁶_D of +14° (C=1.0, chloroform) (Example 210), while the colorless oil obtained from the second eluate had an optical rotation [α]²⁵·⁷_D of −15° (C=1.0, chloroform) (Example 211).

Example 212

4-[4-(3-benzyloxyphenylthio)-2-chlorophenyl]-2-t-butoxycarbonylamino-2-methylbutane-1-ol

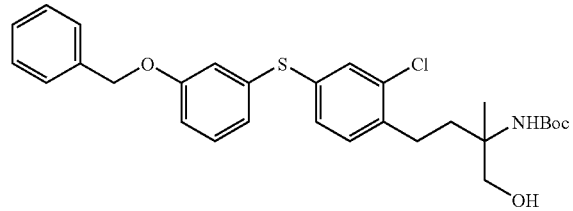

Using the compound of Example 204, the reaction was carried out in the same manner as in Example 76 to obtain the desired compound as a colorless oil.

MS(EI): 527([M]⁺).

¹H-NMR(400 MHz, CDCl₃) δ 1.25(3H, s), 1.44(9H, s), 1.82(1H, td, J=13.0, 4.9 Hz), 2.06(1H, td, J=13.0, 4.9 Hz), 2.65-2.80(2H, m), 3.66-3.74(2H, m), 4.68(1H, br s), 5.02(2H, s), 6.86-6.94(3H, m), 7.15(2H, s), 7.23(1H, t, J=8.0 Hz), 7.32-7.40(6H, m).

Examples 213 and 214

(+) and (−)-4-[4-(3-benzyloxyphenylthio)-2-chlorophenyl]-2-t-butoxycarbonylamino-2-methylbutane-1-ols The compound of Example 212 was optically resolved by HPLC (chiralpak AD, hexane:isopropanol=85:15, detection wavelength=UV 254 nm, flow rate=3 mL/min).

The colorless oil obtained from the first eluate had an optical rotation [α]²⁵·³_D of +4.6° (C=1.0, chloroform) (Example 213), while the colorless oil obtained from the second eluate had an optical rotation [α]²⁵·⁶_D of −2.2° (C=1.0, chloroform) (Example 214).

Example 215

4-[4-(3-benzyloxyphenylthio)-2-chlorophenyl]-2-ethyl-2-methoxycarbonylaminobutane-1-ol

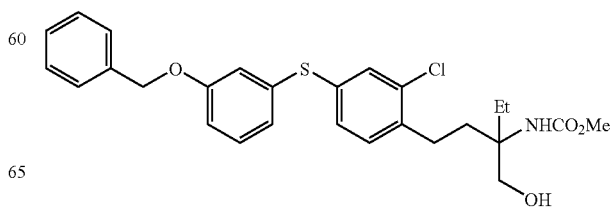

Using the compound of Example 205, the reaction was carried out in the same manner as in Example 76 to obtain the desired product as a colorless oil.

MS(EI): 499([M]+).

$^1$H-NMR(400 MHz, CDCl$_3$) δ 0.94(3H, t, J=7.3 Hz), 1.69 (2H, q, J=7.3 Hz), 1.80-1.94(2H, m), 2.62-2.75(2H, m), 3.65 (3H, s), 3.77(3H, m), 4.77(1H, br), 5.02(2H, s), 6.86-6.95 (3H, m), 7.16(2H, s), 7.23(1H, t, J=8.0 Hz), 7.32-7.41(6H, m).

Examples 216 and 217

(+) and (−)-4-[4-(3-benzyloxyphenylthio)-2-chlorophenyl]-2-ethyl-2-methoxycarbonylaminobutane-1-ols The compound of Example 215 was optically resolved under similar conditions to those used in Examples 213 and 214.

The colorless oil obtained from the first eluate had an optical rotation [α]$^{25.6}_D$ of +11.1° (C=1.0, chloroform) (Example 216), while the colorless oil obtained from the second eluate had an optical rotation [α]$^{26.1}_D$ of −9.67° (C=1.0, chloroform) (Example 217).

Example 218

5-[4-(3-benzyloxyphenylthio)-2-chlorophenyl]-2-butoxycarbonylamino-2-ethylpentane-1-ol

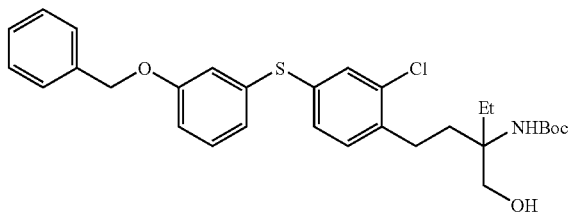

Using the compound of Example 199 and t-butanol instead of methanol, the same procedure was followed as in Example 203 and the reactant was reduced in the same manner as in Example 76 to obtain the desired product as a colorless oil.

MS (EI): 555([M]+).

$^1$H-NMR(400 MHz, CDCl$_3$) δ 0.83(3H, t, J=7.3 Hz), 1.42 (9H, s), 1.55-1.72(6H, m), 2.70(2H, t, J=6.7 Hz), 3.64-3.66 (2H, m), 4.49(1H, br s), 5.02(2H, s), 6.82-6.95(3H, m), 7.12-7.17(2H, m), 7.20-7.25(1H, m), 7.30-7.41(6H, m).

Example 219

4-[4-(3-benzyloxyphenylthio)-2-chlorophenyl]-2-t-butoxycarbonylamino-2-methoxymethyloxymethyl-butnane-1-ol

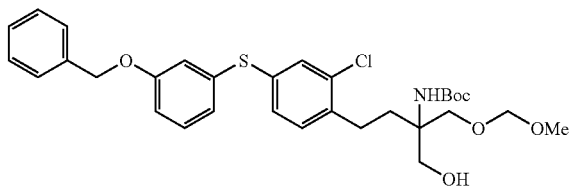

The compound of Example 126 (4.00 g) was dissolved in methylene chloride (100 mL). To this solution, diisopropylethylamine (1.54 mL) was added, followed by dropwise addition of methoxymethylchloride (710 mg) at 0° C. The mixture was stirred for one day until room temperature. Following addition of ice water, the mixture was extracted with ethyl acetate. The extract was then dried over anhydrous sodium sulfate and the solvent was removed by distillation. The resulting residue was purified on a silica gel chlomatography (hexane:ethyl acetate=2:1) to give the desired product as a colorless oil (2.60 g).

$^1$H-NMR(400 MHz, CDCl$_3$) δ 1.45(9H, s), 1.90-2.00(2H, m), 2.68-2.78(2H, m), 3.39(3H, s), 3.54(1H, d, J=9.8 Hz), 3.77(2H, d, J=6.1 Hz), 3.79(1H, d, J=9.8 Hz), 3.99(1H, br), 4.65(2H, s), 5.02(2H, s), 5.20(1H, br s), 6.86-6.94(3H, m), 7.13-7.17(2H, m), 7.22(1H, t, J=8.0 Hz), 7.31-7.40(6H, m).

Examples 220 and 221

(+) and (−)-4-[4-(3-benzyloxyphenylthio)-2-chlorophenyl]-2-t-butoxycarbonylamino-2-methoxymethyloxymethylbutane-1-ols The compound of Example 219 was optically resolved by HPLC (chiralpak AD-H, hexane:isopropanol=85:15, detection wavelength=UV 254 nm, flow rate=3 mL/min).

A colorless oil was obtained from each of the first eluate and the second eluate (Example 220 and Example 221, respectively).

Example 222

5-[4-(3-benzyloxyphenylthio)-2-chlorophenyl]-2-butoxycarbonylamino-2-methoxymethyloxymethyl-pentane-1-ol

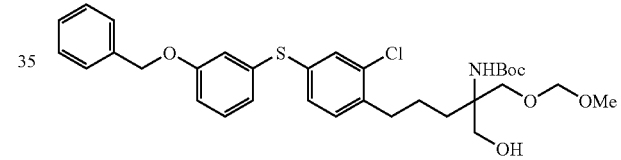

Using the compound of Example 128, the reaction was carried out in the same manner as in Example 219 to obtain the desired product as a colorless oil.

$^1$H-NMR(400 MHz, CDCl$_3$) δ 1.43(9H, s), 1.56-1.68(3H, m), 1.81-1.84(1H, m), 2.67(2H, t, J=7.8 Hz), 3.35(3H, s), 3.46(1H, d, J=9.8 Hz), 3.66-3.68(2H, m), 3.71(1H, d, J=9.8 Hz), 4.61(2H, s), 5.02(2H, s), 5.07(1H, br s), 6.87(1H, ddd, J=8.3, 2.5, 1.0 Hz), 6.91-6.95(2H, m), 7.12-7.16(2H, m), 7.23(1H, t, J=7.8 Hz), 7.31-7.40(6H, m).

Example 223

4-[4-(3-benzyloxyphenylthio)-2-chlorophenyl]-2-t-butoxycarbonylamino-2-methoxymethyloxymethyl-1-dimethoxyphosphoryloxybutane

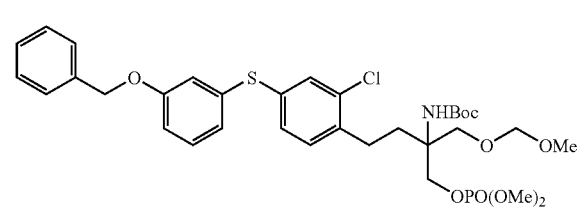

To a methylene chloride solution (2 mL) containing the compound of Example 219 (860 mg), carbon tetrabromide (533 mg) and pyridine (2 mL), trimethyl phosphite (0.19 mL) was added while the mixture was stirred at 0° C. and the mixture was stirred for 5 hours until room temperature. Subsequently, water was added and the mixture was extracted with ethyl acetate. The extract was washed sequentially with water and a saturated aqueous solution of sodium chloride. The organic phase was then dried over anhydrous sodium sulfate. The solvent was removed by distillation and the residue was purified on a silica gel column chromatography (hexane:ethyl acetate=1:1) to obtain the desired product as a colorless oil (830 mg).

FABMS: 696([M+H]$^+$).

$^1$H-NMR(400 MHz, CDCl$_3$) δ 1.45(9H, s), 1.95-2.03(1H, m), 2.08-2.21(1H, m), 2.69-2.78(2H, m), 3.39(3H, s), 3.68 (1H, d, J=9.8 Hz), 3.74(1H, d, J=9.8 Hz), 3.78(6H, d, J=11.0 Hz), 4.22-4.29(2H, m), 4.65(2H, s), 4.97(1H, br s), 5.02(2H, s), 6.88(1H, dd, J=7.9, 2.4 Hz), 6.91-6.95(2H, m), 7.14(2H, s), 7.23(1H, t, J=7.8 Hz), 7.31-7.40(6H, m).

Example 224

(−)-4-[4-(3-benzyloxyphenylthio)-2-chlorophenyl]-2-t-butoxycarbonylamino-2-methoxymethyloxymethyl-1-dimethoxyphosphoryloxybutane Using the compound of Example 220 (first eluate), the reaction was carried out in the same manner as in Example 223 to obtain the desired product as a colorless oil.

$[α]^{26}_D$=−3.01° (C=0.93, chloroform).

Example 225

(+)-4-[4-(3-benzyloxyphenylthio)-2-chlorophenyl]-2-t-butoxycarbonylamino-2-methoxymethyloxymethyl-1-dimethoxyphosphoryloxybutane Using the compound of Example 221 (second eluate), the reaction was carried out in the same manner as in Example 223 to obtain the desired product as a colorless oil.

$[α]^{26}_D$=+1.39° (C=1.03, chloroform).

Example 226

(±)-2-amino-5-[4-(3-benzyloxyphenylthio)-2-chlorophenyl]-2-methylpentane-1-ol

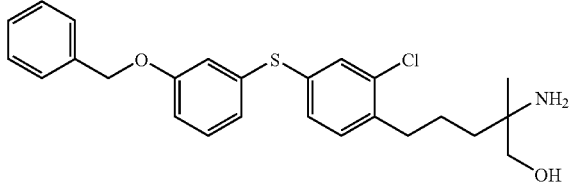

The compound of Example 206 (527 mg) was dissolved in a mixed solvent composed of a 5 mol/L aqueous solution of potassium hydroxide (2 mL), tetrahydrofuran (2 mL) and methanol (3 mL). This mixture was refluxed and stirred for 4 days. Subsequently, the reaction mixture was diluted with water and was extracted with ethyl acetate. The ethyl acetate layer was then washed with a saturated aqueous solution of sodium chloride, was dried over anhydrous magnesium sulfate, and was then concentrated. The resulting residue was purified on a silica gel column chromatography (aminated silica gel, ethyl acetate:ethanol=20:1) to give the desired product as a pale yellow oil (311 mg).

FABMS: 442([M+H]$^+$).

$^1$H-NMR(400 MHz, CDCl$_3$) δ 1.04(3H, s), 1.37-1.67(4H, m), 2.70(2H, t, J=7.3 Hz), 3.29(2H, q, J=9.2 Hz), 5.02(2H, s), 6.86-6.94(3H, m), 7.12-7.17(2H, m), 7.21-7.25(1H, m), 7.31-7.41(6H, m).

Example 227

(+)-2-amino-5-[4-(3-benzyloxyphenylthio)-2-chlorophenyl]-2-methylpentane-1-ol

Using the compound of Example 207 (first eluate), the reaction was carried out in the same manner as in Example 226 to obtain the desired product as a pale yellow oil.

| Elemental analysis (%): C$_{25}$H$_{28}$ClNO$_2$S•1/3H$_2$O | | | |
|---|---|---|---|
| | C | H | N |
| Calcd: | 67.00 | 6.45 | 3.13 |
| Found: | 67.03 | 6.51 | 3.20 |

$[α]^{25.2}_D$ + 2.0° (C = 1.0, chloroform)

Example 228

(−)-2-amino-5-[4-(3-benzyloxyphenylthio)-2-chlorophenyl]-2-methylpentane-1-ol

Using the compound of Example 208 (second eluate), the reaction was carried out in the same manner as in Example 226 to give the desired product as a pale yellow oil.

| Elemental analysis (%): C$_{25}$H$_{28}$ClNO$_2$S•1/4H$_2$O | | | |
|---|---|---|---|
| | C | H | N |
| Calcd: | 67.23 | 6.44 | 3.14 |
| Found: | 67.19 | 6.44 | 3.15 |

$[α]^{25.5}_D$ − 2.6° (C = 1.0, chloroform)

Example 229

MS(EI): 541([M]$^+$).

(+)-5-[4-(3-benzyloxyphenylthio)-2-chlorophenyl]-2-t-butoxycarbonylamino-1-dimethoxyphosphoryloxy-2-methylpentane

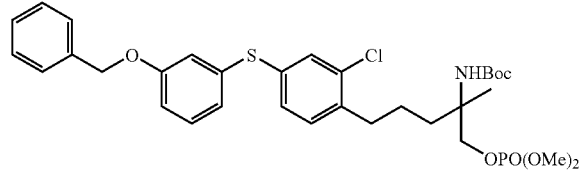

The compound of Example 227 (410 mg) was dissolved in acetonitrile (10 mL). While this solution was chilled in an ice bath, Boc$_2$O (303 mg) was added and the mixture was stirred for 3 hours at room temperature. The reaction mixture was concentrated and the residue was dissolved in ethyl acetate. This solution was washed with water and a saturated aqueous solution of sodium chloride. The organic phase was then dried over anhydrous sodium sulfate and was concentrated. The resulting residue was purified on a silica gel column chromatography (hexane:ethyl acetate=5:1) to give a t-butoxycarbonylamino product as a pale yellow oil (473 mg). The resulting compound (473 mg), along with carbon tetrabromide (434 mg), was dissolved in pyridine (2.00 mL). While this solution was chilled in an ice bath, trimethyl phosphite (0.205 mL)

was added and the mixture was allowed to warm to room temperature and was stirred for 2 hours. Subsequently, the reaction mixture was diluted with water and was extracted with ethyl acetate. The extract was then washed with a saturated aqueous solution of sodium chloride, was dried over anhydrous magnesium sulfate, and was then concentrated. The resulting residue was purified on a silica gel column chromatography (hexane:ethyl acetate=5:1 to 1:1) to give the desired product as a pale yellow oil (534 mg).

$^1$H-NMR(400 MHz, CDCl$_3$) δ 1.25(3H, s), 1.41(9H, s), 1.58-1.91(4H, m), 2.70(2H, t, J=7.3 Hz), 3.77(6H, d, J=11.0 Hz), 3.96-4.00(1H, m), 4.13-4.16(1H, m), 4.51(1H, brs), 5.02 (2H, s), 6.86-6.89(1H, m), 6.92-6.96(2H, m), 7.11-7.16(2H, m), 7.23(1H, t, J=7.9 Hz), 7.31-7.34(2H, m), 7.35-7.39(4H, m).

Example 230

(−)-5-[4-(3-benzyloxyphenylthio)-2-chlorophenyl]-2-t-butoxycarbonylamino-1-dimethoxyphosphoryloxy-2-methylpentane Using the compound of Example 228, the reaction was carried out in the same manner as in Example 229 to obtain the desired product as a pale yellow oil.

$^1$H-NMR(400 MHz, CDCl$_3$) δ 1.25(3H, s), 1.41(9H, s), 1.58-1.91(4H, m), 2.70(2H, t, J=7.3 Hz), 3.77(6H, d, J=11.0 Hz), 3.97-4.00(1H, m), 4.13-4.17(1H, m), 4.51(1H, brs), 5.02 (2H, s), 6.86-6.89(1H, m), 6.92-6.95(2H, m), 7.11-7.16(2H, m), 7.23(1H, t, J=7.9 Hz), 7.32-7.34(2H, m), 7.35-7.40(4H, m).

Example 231

5-[4-(3-benzyloxyphenylthio)-2-chlorophenyl]-2-t-butoxycarbonylamino-2-methoxymethyloxymethyl-1-dimethoxyphosphoryloxypentane

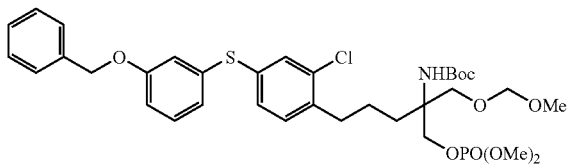

Using the compound of Example 222, the reaction was carried out in the same manner as in Example 223 to obtain the desired product as a colorless oil.

FABMS: 710([M+H]$^+$).

$^1$H-NMR(400 MHz, CDCl$_3$) δ 1.41(9H, s), 1.57-1.62(2H, m), 1.76-1.80(1H, m), 2.00-2.05(1H, m), 2.70(2H, t, J=7.8 Hz), 3.34(3H, s), 3.57(1H, d, J=9.5 Hz), 3.65(1H, d, J=9.5 Hz), 3.77(6H, d, J=11.0 Hz), 4.12(2H, d, J=7.1 Hz), 4.60(2H, s), 4.81(1H, br s), 5.02(2H, s), 6.87(1H, ddd, J=8.3, 2.5, 1.0 Hz), 6.92-7.00(2H, m), 7.10-7.16(2H, m), 7.23(1H, t, J=7.8 Hz), 7.28-7.52(6H, m).

Example 232

Diethyl 6-[4-(3-benzyloxyphenylthio)-2-chlorophenyl]-3-t-butoxycarbonylamino-1-hexenylphosphonate

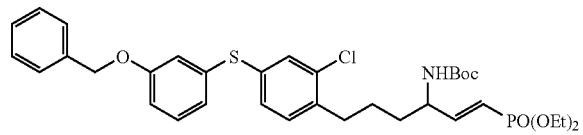

Ethyl methylenebisphosphonate (940 mg) in THF (5 mL) was chilled to −78° C. under an argon gas atmosphere. To this solution, a 1.6 mol/L n-BuL-hexane solution (2 mL) was added dropwise and the mixture was stirred for 30 min, followed by dropwise addition of a THF solution (15 mL) of the compound of Example 193 (1.58 g). After 3 hours, a saturated ammonium chloride solution was added and the mixture was extracted with ethyl acetate. The organic phase was washed with water and a saturated aqueous solution of sodium chloride and was dried over anhydrous sodium sulfate. The solvent was removed by distillation to give the desired product as a colorless oil (1.71 g).

FABMS: 660([M+H]$^+$).

$^1$H-NMR(400 MHz, CDCl$_3$) δ 1.29-1.33(6H, m), 1.43(9H, s), 1.54-1.68(4H, m), 2.71-2.73(2H, m ), 4.03-4.11(4H, m), 4.32(1H, br), 4.47(1H, br), 5.03(2H, s), 5.77(1H, t, J=17.7 Hz), 6.60-6.71(1H, m), 6.87-6.96(3H, m), 7.09-7.15(2H, m), 7.21-7.41(7H, m).

Example 233

Diethyl 3-amino-6-[4-(3-benzyloxyphenylthio)-2-chlorophenyl]-1-hexenylphosphonate hydrochloride

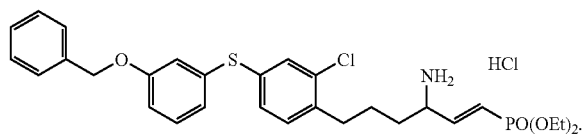

The compound of Example 232 (300 mg) was dissolved in methanol (10 mL) containing 10% hydrochloric acid in an ice bath. The mixture was stirred for 6 hours until room temperature and the solvent was concentrated. This gave the desired product as a colorless oil (250 mg).

FABMS: 560([M+H]$^+$).

$^1$H-NMR(400 MHz, DMSOd$_6$) δ 1.16-1.22(6H, m), 1.53-1.77(4H, m), 2.68-2.69(2H, m ), 3.05(1H, br), 3.94-4.07(4H, m), 5.09(2H, s), 6.13(1H, t, J=17.8 Hz), 6.46-6.55(1H, m), 6.89-7.00(3H, m), 7.20-7.22(1H, m), 7.29-7.41(8H, m), 8.44 (3H, br s).

Example 234

Diethyl 6-[4-(3-benzyloxyphenylthio)-2-chlorophenyl]-3-t-butoxycarbonylaminohexylphosphonate

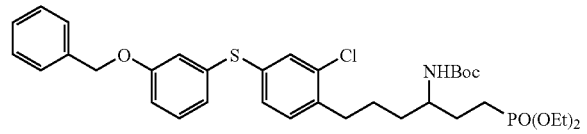

The compound of Example 232 was reduced in the same manner as in Reference Example 125 to obtain the desired product as a colorless oil.

FABMS: 662([M+H]$^+$).

$^1$H-NMR(400 MHz, CDCl$_3$) δ 1.32(6H, t, J=7.3 Hz), 1.43 (9H, s), 1.46-1.82(8H, m), 2.67-2.73(2H, m), 3.62(1H, br), 4.03-4.13(4H, m), 4.32-4.34(1H, br), 5.02(2H, s), 6.86-6.95 (3H, m), 7.10-7.16(2H, m), 7.23(1H, t, J=8.0 Hz), 7.32-7.40 (6H, m).

Example 235

Diethyl 3-amino-6-[4-(3-benzyloxyphenylthio)-2-chlorophenyl]hexylphosphonate hydrochloride

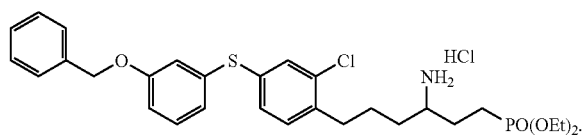

The compound of Example 234 was reacted in the same manner as in Example 233 to obtain the desired product as a pale brown oil.

FABMS: 562([M+H]$^+$).

$^1$H-NMR(400 MHz, DMSOd$_6$) δ 1.21(6H, t, J=6.7 Hz), 1.59-1.85(8H, m), 2.67(2H, br s), 3.15(1H, br), 3.91-4.01 (4H, m), 5.08(2H, s), 6.88-6.99(3H, m), 7.21-7.39(9H, m), 8.08(3H, br s).

Example 236

2-amino-5-[4-(3-benzyloxyphenylthio)-2-chlorophenyl]-2-hydroxymethylpentylphosphonate monoester

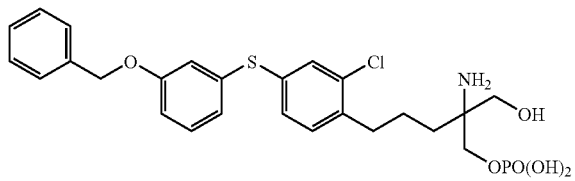

To an acetonitrile solution (5 mL) of the compound of Example 231 (500 mg), TMSI (0.5 mL) was added and the mixture was stirred for 3 hours. The solvent was concentrated and the residue was purified on a silica gel column chromatography to obtain the desired product as a colorless powder (120 mg).

FABMS: 538([M+H]$^+$).

$^1$H-NMR(400 MHz, DMSOd$_6$) δ 1.60(4H, br s), 2.63(2H, br s), 3.38-3.44(2H, m), 3.72(2H, br s), 5.08(2H, s), 6.87-6.98 (3H, m), 7.20-7.38(9H, m).

| Elemental analysis (%): C$_{25}$H$_{29}$ClNO$_6$SP•H$_2$O | | | |
|---|---|---|---|
| | C | H | N |
| Calcd: | 54.00 | 5.62 | 2.52 |
| Found: | 54.10 | 5.37 | 2.62 |

Example 237

2-amino-4-[4-(3-benzyloxyphenylthio)-2-chlorophenyl]-2-hydroxymethylbutylphosphonate monoester

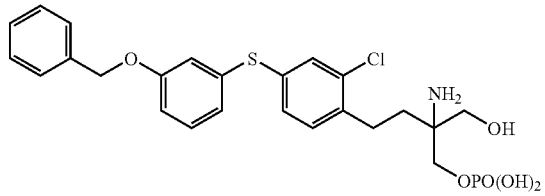

Using the compound of Example 223, the reaction was carried out in the same manner as in Example 236 to obtain the desired product as a colorless powder.

FABMS: 524([M+H]$^+$).

$^1$H-NMR(400 MHz, DMSOd$_6$) δ 1.77-1.78(2H, m), 2.71-2.75(2H, m), 3.50-3.58(2H, m), 3.76-3.88(2H, m), 5.08(2H, s), 6.89(1H, t, J=7.3 Hz), 6.96-6.99(2H, m), 7.21-7.38(9H, m).

| Elemental analysis (%): C$_{24}$H$_{27}$ClNO$_6$SP | | | |
|---|---|---|---|
| | C | H | N |
| Calcd: | 55.01 | 5.19 | 2.67 |
| Found: | 54.94 | 5.26 | 2.77 | m.p. = 200–202° C.

Example 238

2-amino-5-[2-chloro-4-(3-hydroxyphenylthio)phenyl]-2-hydroxymethylpentylphosphonate monoester

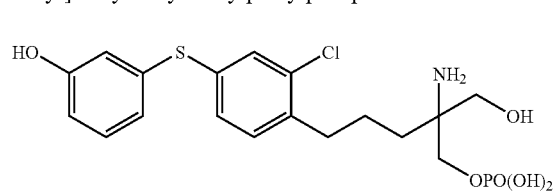

Instead of ice-cold environment, the experiment of Example 236 was carried out at room temperature to give the desired product as a colorless powder.

FABMS: 448([M+H]$^+$).

$^1$H-NMR(400 MHz, DMSOd$_6$) δ 1.54-1.62(4H, m), 2.51-2.73(2H, m), 3.37-3.41(2H, m), 3.57-3.75(2H, m), 6.62(1H, dd, J=8.0, 1.8 Hz), 6.67-6.68(1H, m), 6.75(1H, dd, J=8.6, 1.2 Hz), 7.15(1H, t, J=8.0 Hz), 7.27(1H, dd, J=8.0, 2.0 Hz), 7.34-7.36(2H, m).

| Elemental analysis (%): C$_{18}$H$_{23}$ClNO$_6$SP•0.5H$_2$O | | | |
|---|---|---|---|
| | C | H | N |
| Calcd: | 47.32 | 5.29 | 3.07 |
| Found: | 47.06 | 5.07 | 3.07 | m.p. = 180–182° C.

Example 239

(+)-2-amino-5-[4-(3-benzyloxyphenylthio)-2-chlorophenyl]-2-methylpentylphosphonate monoester

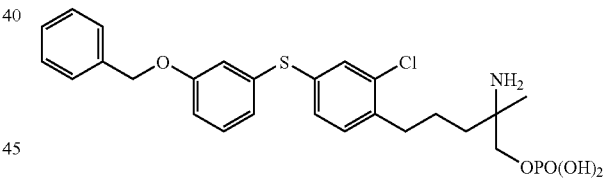

The compound of Example 229 was reacted in the same manner as in Example 236 to obtain the desired product as a colorless powder.

HR-MS(FAB+): 522.1255(−1.6 mmu).

$^1$H-NMR(400 MHz, DMSOd$_6$) δ 1.12(3H, s), 1.51-1.65 (4H, m), 2.64-2.70(2H, m), 3.66(2H, d, J=11 Hz), 5.09(2H, s), 6.91(1H, d, J=7.3 Hz), 6.97-7.01(2H, m), 7.20-7.24(1H, m), 7.30-7.42(8H, m).

| Elemental analysis (%): C$_{25}$H$_{29}$ClNO$_5$PS•1/2H$_2$O | | | |
|---|---|---|---|
| | C | H | N |
| Calcd: | 56.55 | 5.69 | 2.64 |
| Found: | 56.40 | 5.60 | 2.77 |

[α]$^{22.6}_D$ + 3.2° (C = 1.0, methanol).
m.p. = 207–210° C.

Example 240

(−)-2-amino-5-[4-(3-benzyloxyphenylthio)-2-chlorophenyl]-2-methylpentylphosphonate monoester Using the compound of Example 228, the reaction was carried out in the same manner as in Example 236 to obtain the desired product as a colorless powder.

HR-MS(FAB+): 522.1277(+0.6 mmu).

$^1$H-NMR(400 MHz, DMSOd$_6$) δ 1.12(3H, s), 1.51-1.65 (4H, m), 2.63-2.70(2H, m), 3.67(2H, d, J=12 Hz), 5.09(2H, s), 6.89-6.92(1H, m), 6.96-7.01(2H, m), 7.22-7.24(1H, m), 7.32-7.42(8H, m).

$[\alpha]^{23.4}_D$ −3.1° (C=1.0, methanol).

m.p.=200-203° C.

Example 241

3-amino-6-[4-(3-benzyloxyphenylthio)-2-chlorophenyl]hexylphosphonic acid

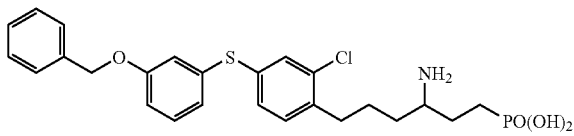

Using the compound of Example 234, the reaction was carried out in the same manner as in Example 236 to obtain the desired product as a colorless powder.

FABMS: 506([M+H]$^+$).

$^1$H-NMR(400 MHz, DMSOd$_6$) δ 1.56-1.72(8H, m), 2.67 (2H, br s), 3.18(1H, br s), 5.08(2H, s), 6.88-7.00(3H, m), 7.21-7.40(9H, m).

| Elemental analysis (%): C$_{25}$H$_{29}$ClNO$_4$PS•1/2H$_2$O | | | |
|---|---|---|---|
| | C | H | N |
| Calcd: | 58.30 | 5.87 | 2.72 |
| Found: | 58.29 | 5.71 | 2.80 |

Example 242

3-amino-6-[4-(3-benzyloxyphenylthio)-2-chlorophenyl]-1-hexenylphosphonic acid

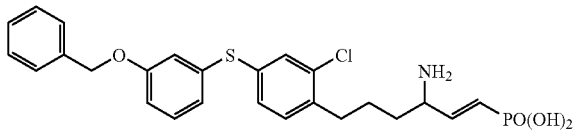

Using the compound of Example 232, the reaction was carried out in the same manner as in Example 236 to obtain the desired product as a colorless powder.

FABMS: 504([M+H]$^+$).

$^1$H-NMR(400 MHz, DMSOd$_6$) δ 1.53-1.70(4H, m), 2.69 (2H, t, J=7.3 Hz), 3.83-3.99(1H, m), 5.12(2H, s), 6.03(1H, t, J=16.5 Hz), 6.28(1H, d,d,d, J=16.5, 10.0, 7.3 Hz), 6.89-7.01 (3H, m), 7.20-7.41(9H, m).

Example 243

4-[4-(3-benzyloxyphenylthio)-2-chlorophenyl]-2-t-butoxycarbonylamino-2-t-butyldimethylsiloxymethyl-1-dimethoxyphosphoryloxybutane

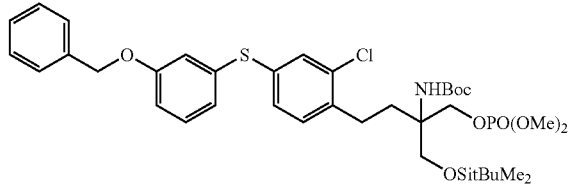

The compound of Example 126 was reacted with t-BuMe$_2$SiCl in the same manner as in Example 191. The resulting compound was reacted in the same manner as in Example 223 to give the desired product as a colorless oil.

FABMS: 766([M+H]$^+$).

$^1$H-NMR(400 MHz, CDCl$_3$) δ 0.09(6H, s), 0.91(9H, s), 1.45(9H, s), 1.86-1.98(1H, m), 2.05-2.15(1H, m), 2.72(2H, t, J=8.6 Hz), 3.72(2H, s), 3.78(6H, d, J=11.0 Hz), 4.17-4.24 (2H, m), 4.78(1H, br s), 5.02(2H, s), 6.86-6.95(3H, m), 7.21 (2H, s), 7.23(1H, t, J=7.3 Hz), 7.31-7.41(6H, m).

Example 244

4-[4-(3-benzyloxyphenylthio)-2-chlorophenyl]-2-t-butoxycarbonylamino-2-hydroxymethyl-1-dimethoxyphosphoryloxybutane

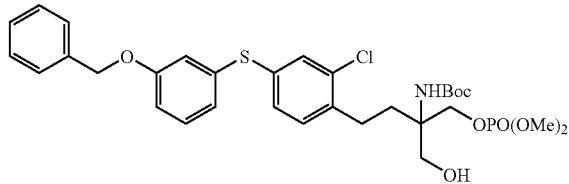

To a THF solution (30 mL) of the compound of Example 243 (2.70 g), 1 mol/L tetrabutylammonium fluoride in THF (5 mL) was added and the mixture was stirred for 1 hour at room temperature. Following addition of water, the mixture was extracted with ethyl acetate. The extract was washed with a saturated aqueous solution of sodium chloride and the organic phase was dried over anhydrous sodium sulfate. The solvent was removed by distillation and the residue was purified on a silica gel column chromatography (hexane:ethyl acetate=2:1) to obtain the desired product as a colorless oil (2.30 g).

FABMS: 652([M+H]$^+$).

$^1$H-NMR(400 MHz, CDCl$_3$) δ 1.45(9H, s), 1.83-1.90(1H, m), 2.09-2.17(1H, m), 2.71(2H, t, J=8.6 Hz), 3.71-3.77(2H, m), 3.79(6H, d, J=11.0 Hz), 4.04(1H, br), 4.17-4.29(2H, m), 5.00(1H, br s), 5.02(2H, s), 6.86-6.95(3H, m), 7.14-7.15(2H, m), 7.23(1H, t, J=7.3 Hz), 7.31-7.39(6H, m).

Examples 245 and 246

(+) and (−)-4-[4-(3-benzyloxyphenylthio)-2-chlorophenyl]-2-t-butoxycarbonylamino-2-t-butyldimethylsiloxymethyl-1-dimethoxyphosphoryloxybutanes The compound of Example 244 was optically resolved by HPLC (chiralpak AS-H, hexane:isopropanol=8:2, detection wavelength=UV 254 nm, flow rate=1 mL/min). The colorless oil obtained from the first eluate had an optical rotation $[\alpha]^{26}_D$ of −6.12° (C=1.0, methanol) (Example 245), while the colorless oil obtained from the second eluate had an optical rotation $[\alpha]^{27}{}_D$ of +5.79° (C=1.0, methanol) (Example 246).

Example 247

(+)-4-[4-(3-benzyloxyphenylthio)-2-chlorophenyl]-2-t-butoxycarbonylamino-1-dimethoxyphosphoryloxy-2-methylbutane

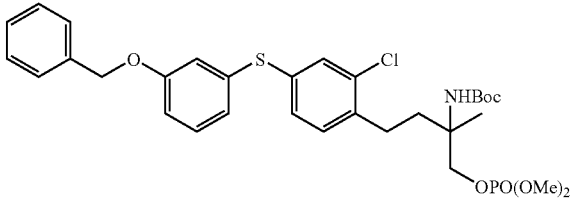

Using the compound of Example 213, the reaction was carried out in the same manner as in Example 223 to obtain the desired product as a pale brown oil.

FABMS: 636([M+H]$^+$).

$^1$H-NMR(400 MHz, CDCl$_3$) δ 1.36(3H, s), 1.44(9H, s), 1.77-1.82(1H, m), 2.05-2.15(1H, m), 2.68-2.74(2H, m), 3.78 (6H, d, J=11.0 Hz), 4.01-4.05(1H, m), 4.21-4.25(1H, m), 4.63(1H, br), 5.02(2H, s), 6.87-6.94(3H, m), 7.23-7.27(3H, m), 7.32-7.42(6H, m).

Example 248

(−)-4-[4-(3-benzyloxyphenylthio)-2-chlorophenyl]-2-t-butoxycarbonylamino-1-dimethoxyphosphoryloxy-2-methylbutane Using the compound of Example 214, the reaction was carried out in the same manner as in Example 223 to obtain the desired product as a pale brown oil.

FABMS: 636([M+H]$^+$).

$^1$H-NMR(400 MHz, CDCl$_3$) δ 1.36(3H, s), 1.44(9H, s), 1.74-1.82(1H, m), 2.05-2.15(1H, m), 2.66-2.76(2H, m), 3.78 (6H, d, J=11.0 Hz), 4.01-4.05(1H, m), 4.21-4.25(1H, m), 4.63(1H, br), 5.02(2H, s), 6.86-6.95(3H, m), 7.21-7.27(3H, m), 7.31-7.41(6H, m).

Example 249

(+)-2-amino-4-[4-(3-benzyloxyphenylthio)-2-chlorophenyl]-2-methylbutylphosphonate monoester

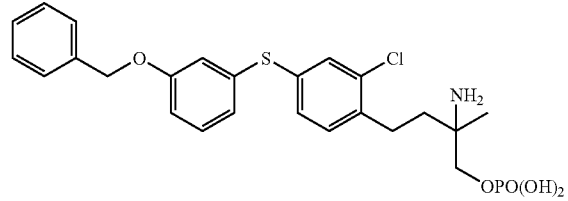

Using the compound of Example 247, the reaction was carried out in the same manner as in Example 236 to obtain the desired product as a colorless powder.

FABMS: 508([M+H]$^+$).

$^1$H-NMR(400 MHz, DMSOd$_6$-TFA) δ 1.29(3H, s), 1.72-1.84(2H, m), 2.71(2H, t, J=7.9 Hz), 3.87(1H, dd, J=4.9, 11.0 Hz), 3.93(1H, dd, J=4.9, 11.0 Hz), 5.08(2H, s), 6.91(1H, d, 7.3 Hz), 6.96-7.01(2H, m), 7.23(1H, dd, J=1.8, 7.9 Hz), 7.29-7.40(8H, m).

$[\alpha]^{25.6}{}_D$ +15.1° (C=1.0, 10% TFA in DMSO).

Elemental analysis (%): C$_{24}$H$_{27}$ClNO$_5$PS•2/3CF$_3$CO$_2$H

|  | C | H | N |
|---|---|---|---|
| Calcd: | 52.10 | 4.78 | 2.40 |
| Found: | 52.29 | 4.75 | 2.68 |

Example 250

(−)-2-amino-4-[4-(3-benzyloxyphenylthio)-2-chlorophenyl]-2-methylbutylphosphonate monoester Using the compound of Example 248, the reaction was carried out in the same manner as in Example 236 to obtain the desired product as a colorless powder.

FABMS: 508([M+H]$^+$).

$^1$H-NMR(400 MHz, DMSO-TFA) δ 1.29(3H, s), 1.76-1.90 (2H, m), 2.71(2H, t, J=7.9 Hz), 3.87(1H, dd, J=4.9, 11.0 Hz), 3.93(1H, dd, J=4.9, 11.0 Hz), 5.08(2H, s), 6.90-7.01(3H, m), 7.24(1H, dd, J=1.8, 7.9 Hz), 7.29-7.40(8H, m).

$[\alpha]^{26.3}{}_D$ −12.6° (C=1.0, 10% TFA in DMSO).

Elemental analysis (%): C$_{24}$H$_{27}$ClNO$_5$PS•1/2H$_2$O

|  | C | H | N |
|---|---|---|---|
| Calcd: | 55.76 | 5.46 | 2.71 |
| Found: | 55.77 | 5.19 | 2.97 |

Examples 251 and 252

Diethyl (Z)- and (E)-5-[4-(3-benzyloxyphenylthio)-2-chlorophenyl]-3-t-butoxycarbonylamino-1-fluoro-1-pentenylphosphonates

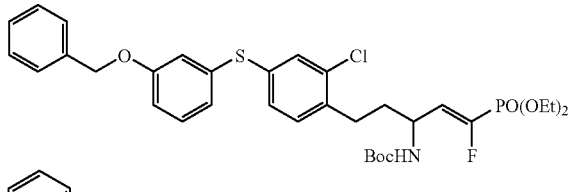

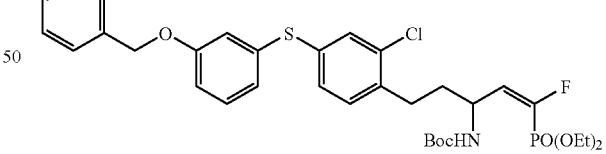

The compound of Example 127 was oxidized in the same manner as in Example 193 to obtain an aldehyde for use in the subsequent reaction.

Meanwhile, trimethylchlorosilane (1.0 mL) was added to diethyl dibromofluoromethylphosphate (1.48 mL) in THF (75 mL), and the mixture was cooled to −78° C. Subsequently, 1.6 mol/L n-butyllithium in hexane (11.3 mL) was added dropwise and the mixture was stirred for 40 min. Subsequently, the aldehyde obtained above (3.68 g) in THF (25.0 mL) was added dropwise over 10 min. The mixture was allowed to warm to 0° C. and was stirred for 5 hours. Following addition of aqueous ammonium chloride, the mixture was extracted with ethyl acetate. The ethyl acetate layer was then washed with a saturated aqueous solution of sodium chloride, was dried over anhydrous sodium sulfate, and was concentrated. The resulting residue was purified on a silica gel column chromatography (hexane:ethyl acetate=10:1 to 1:1). As a result, the Z-form was obtained from the first eluate as a yellow oil (1.70 g), and the E-form was obtained from the second eluate as a yellow oil (667 mg).

Z-form: Example 251

FABMS: 664([M+H]$^+$).

$^1$H-NMR(400 MHz, CDCl$_3$) δ 1.31-1.38(6H, m), 1.43(9H, s), 1.88-2.00(2H, m), 2.69-2.83(2H, m), 4.13-4.22(4H, m), 4.80-4.90(1H, m), 5.02(2H, s), 5.15-5.30(1H, br), 6.08-6.30 (1H, m), 6.87-6.88(1H, m), 6.90-6.95(2H, m), 7.11-7.15(2H, m), 7.22(1H, t, J=7.9 Hz), 7.31-7.39(6H, m).

E-form: Example 252

FABMS: 663([M]$^+$).

$^1$H-NMR(400 MHz, CDCl$_3$) δ 1.34-1.36(6H, m), 1.44(9H, s), 1.82-1.88(2H, m), 2.71-2.78(2H, m), 4.15-4.23(4H, m), 4.60-4.65(2H, m), 5.02(2H, s), 5.80-6.00(1H, m), 6.89(1H, dd, J=1.4, 7.9 Hz), 6.93-6.95(2H, m), 7.11-7.17(2H, m), 7.23 (1H, t, J=7.9 Hz), 7.31-7.41(6H, m).

Example 253

(Z)-3-amino-5-[4-(3-benzyloxyphenylthio)-2-chlorophenyl]-1-fluoro-1-pentenylphosphonic acid

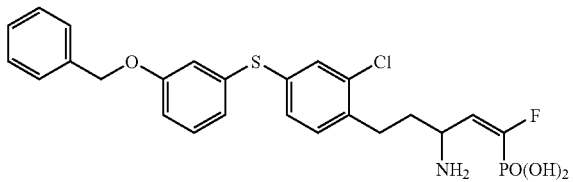

Using the compound of Example 251, the reaction was carried out in the same manner as in Example 236 to obtain the desired product as a colorless powder.

FABMS: 508([M+H]$^+$).

$^1$H-NMR(400 MHz, DMSd$_6$) δ 1.78-1.98(2H, m), 2.69 (2H, t, J=7.9 Hz), 4.19(1H, br), 5.08(2H, s), 5.47-5.62(1H, m), 6.90(1H, d, J=7.9 Hz), 6.97-6.99(2H, m), 7.20(1H, d, J=7.9 Hz), 7.29-7.40(8H, m), 8.67(2H, br).

m.p.=285-288° C.

| Elemental analysis (%): C$_{24}$H$_{24}$ClFNO$_4$PS•13/10H$_2$O | | | |
|---|---|---|---|
| | C | H | N |
| Calcd: | 54.25 | 5.05 | 2.64 |
| Found: | 54.54 | 5.49 | 2.44 |

Example 254

(E)-3-amino-5-[4-(3-benzyloxyphenylthio)-2-chlorophenyl]-1-fluoro-1-pentenylphosphonic acid

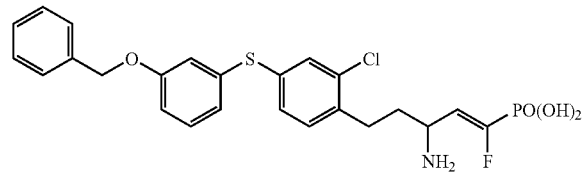

Using the compound of Example 252, the reaction was carried out in the same manner as in Example 236 to obtain the desired product as a colorless powder.

FABMS: 508([M+H]$^+$).

$^1$H-NMR(400 MHz, CDCl$_3$) δ 1.79-1.91(1H, m), 1.91-2.02(1H, m), 2.58-2.70(2H, m), 3.84-3.98(1H, m), 5.08(2H, s), 5.43-5.62(1H, m), 6.90(1H, m), 6.95-6.99(2H, m), 7.17-7.38(9H, m), 8.68(2H, br).

m.p.=288-290° C.

Examples 255 and 256

Diethyl (Z)- and (E)-6-[4-(3-benzyloxyphenylthio)-2-chlorophenyl]-3-t-butoxycarbonylamino-1-fluoro-1-hexenylphosphonates

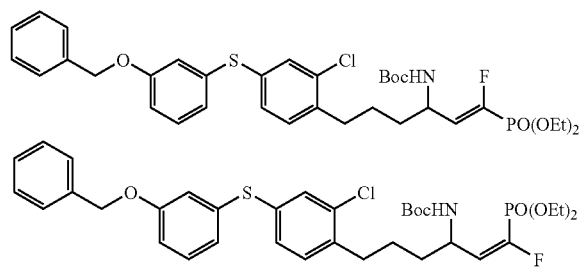

The compound of Example 193 was reacted in the same manner as in Examples 251 and 252 to obtain the desired Z-form (Example 255) and the E-form (Example 256), respectively. Each product was obtained as a yellow oil.

Z-form: Example 255

FABMS: 678([M+H]$^+$).

$^1$H-NMR(400 MHz, CDCl$_3$) δ 1.31-1.37(6H, m), 1.41(9H, s), 1.61-1.71(4H, m), 2.73(2H, m), 4.10-4.18(4H, m), 4.84 (1H, br), 5.02(2H, s), 5.06-5.15(1H, m), 6.01-6.19(1H, m), 6.87(1H, dd, J=1.2, 9.7 Hz), 6.91-6.94(2H, m), 7.12-7.16(2H, m), 7.22(1H, t, J=7.9 Hz), 7.30-7.39(6H, m).

E-form: Example 256

FABMS: 678([M+H]$^+$).

$^1$H-NMR(400 MHz, CDCl$_3$) δ 1.32-1.37(6H, m), 1.43(9H, s), 1.61-1.66(4H, m), 2.72(2H, t, J=7.3 Hz), 4.11-4.17(4H, m), 4.50-4.60(2H, m), 5.02(2H, s), 5.73-5.90(1H, m), 6.86-6.89(1H, m), 6.92-6.96(2H, m), 7.10(1H, d, J=7.9 Hz), 7.13 (1H, dd, J=1.2, 7.9 Hz), 7.23(1H, t, J=7.9 Hz), 7.31-7.40(6H, m).

Example 257

Diethyl 6-[4-(3-benzyloxyphenylthio)-2-chlorophenyl]-3-t-butoxycarbonylamino-1-fluorohexylphosphonate

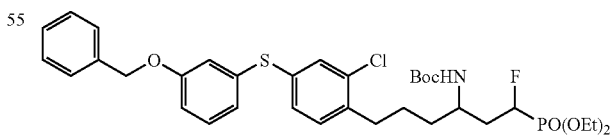

Using the compounds of Examples 255 and 256, the reaction was carried out in the same manner as in Reference Example 123 to obtain the desired product as a yellow oil.

FABMS: 679([M+H]$^+$).

$^1$H-NMR(400 MHz, CDCl$_3$) δ 1.35(6H, s), 1.43(9H, s), 1.49-1.57(2H, m), 1.58-1.75(4H, m), 2.65-2.80(2H, m), 3.82-3.94(1H, m), 4.20 (4H, q, J=7.3 Hz), 4.35-4.55(1H, m), 4.74-

4.94(1H, m), 5.02(2H, s), 6.87-6.99(1H, m), 6.92-6.95(2H, m), 7.11-7.17(2H, m), 7.23(1H, t, J=7.9 Hz), 7.32-7.43(6H, m).

Example 258

Dimethyl 6-[4-(3-benzyloxyphenylthio)-2-chlorophenyl]-3-t-butoxycarbonylamino-3-methyl-1-hexenylphosphonate

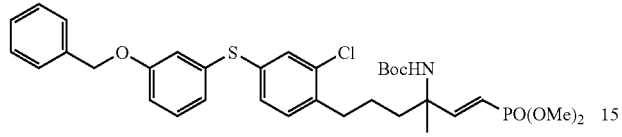

Following the same procedure as in Example 229, the compound of Example 226 was reacted to form a Boc product and, following the same procedure as in Example 193, the product was oxidized to an aldehyde. Subsequently, using methyl methylenebisphosphonate, the same procedure was followed as in Example 232 to give the desired product as a pale yellow oil.

FABMS: 646([M+H]$^+$).

$^1$H-NMR(400 MHz, CDCl$_3$) δ 1.36(3H, s), 1.40(9H, s), 1.54-1.64(2H, m), 1.67-1.70(1H, m), 1.82-1.92(1H, m), 2.69 (2H, t, J=7.9 Hz), 3.72(6H, d, J=11.0 Hz), 4.55(1H, br), 5.02(2H, s), 5.62(1H, dd, J=17.1, 18.3 Hz), 6.75(1H, dd, J=17.1, 22.6 Hz), 6.80-6.89(1H, m), 6.93-6.96(2H, m), 7.10 (1H, d, J=7.9 Hz), 7.15(1H, dd, J=1.8, 7.9 Hz), 7.23(1H, t, J=7.9 Hz), 7.31-7.41(6H, m).

Example 259

Dimethyl 6-[4-(3-benzyloxyphenylthio)-2-chlorophenyl]-3-t-butoxycarbonylamino-3-methylhexylphosphonate

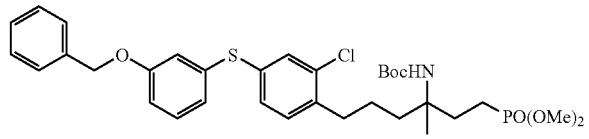

The compound of Example 258 was reacted in the same manner as in Reference Example 123 to obtain the desired product as a pale yellow oil.

FABMS: 648([M+H]$^+$).

$^1$H-NMR(400 MHz, CDCl$_3$) δ 1.13(3H, s), 1.41(9H, s), 1.50-1.60(2H, m), 1.65-1.86(4H, m), 2.02-2.08(2H, m), 2.68 (2H, t, J=7.3 Hz), 3.73(6H, d, J=11.0 Hz), 4.32(1H, br), 5.01(2H, s), 6.87(1H, dd, J=2.4, 8.5 Hz), 6.91-6.95(2H, m), 7.11(1H, d, J=7.9 Hz), 7.14(1H, dd, J=1.8, 7.9 Hz), 7.22(1H, t, J=7.9 Hz), 7.31-7.40(6H, m).

Example 260

3-amino-6-[4-(3-benzyloxyphenylthio)-2-chlorophenyl]-3-methylhexylphophonic acid

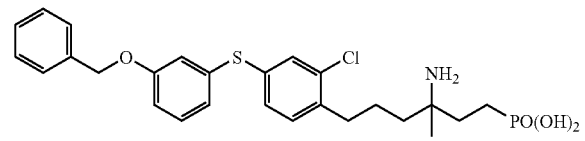

The compound of Example 259 was reacted in the same manner as in Reference Example 236 to obtain the desired product as a colorless powder.

FABMS: 520([M+H]$^+$).

$^1$H-NMR(400 MHz, DMSOd$_6$) δ 1.16(3H, s), 1.20(2H, br), 1.50-1.60(6H, m), 1.73(2H, t, J=7.3 HZ), 2.65-2.70(2H, m), 5.07(2H, s), 6.89(1H, d, J=7.4 Hz), 6.94-6.98(2H, m), 7.21-7.22(1H, m), 7.31-7.37(8H, m).

m.p.=195-197° C.

Example 261

3-amino-6-[4-(3-benzyloxyphenylthio)-2-chlorophenyl]-3-methyl-1-hexenylphosphonic acid

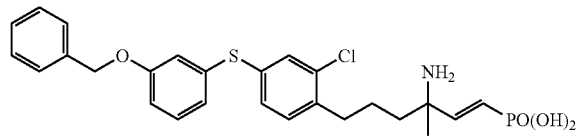

The compound of Example 258 was reacted in the same manner as in Example 236 to obtain the desired product as a colorless powder.

FABMS: 518([M+H]$^+$).

$^1$H-NMR(400 MHz, DMSOd$_6$) δ 1.25(3H, s), 1.39-1.57 (2H, m), 1.65-1.79(2H, m), 2.52-2.70(2H, m), 5.05(2H, s), 5.77-5.94(1H, m), 6.08-6.26(1H, m), 6.85(1H, d, J=6.7 Hz), 6.91-6.99(2H, m), 7.10-7.42(9H, m), 8.39-9.20(2H, br).

m.p.=243-245° C.

| Elemental analysis (%): C$_{26}$H$_{29}$ClFNO$_4$PS•H$_2$O | | | |
|---|---|---|---|
| | C | H | N |
| Calcd: | 58.26 | 5.83 | 2.61 |
| Found: | 57.80 | 5.31 | 2.74 |

Example 262

Dimethyl 6-[4-(3-benzyloxyphenylthio)-2-chlorophenyl]-3-t-butoxycarbonylamino-3-methoxymethyloxymethyl-1-hexenylphosphonate

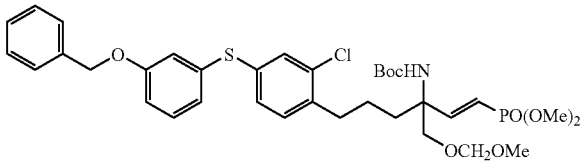

The compound of Example 222 was reacted in the same manner as in Example 232 to obtain the desired product as a colorless oil.

FABMS: 706([M+H]$^+$).

$^1$H-NMR(400 MHz, CDCl$_3$) δ 1.41(9H, s), 1.56-1.69(2H, m), 1.75-1.90(1H, m), 1.93-1.99(1H, m), 2.69(2H, t, J=7.9 Hz), 3.33(3H, s), 3.60-3.63(2H, m), 3.71(6H, d, J=11.0 Hz), 4.58(2H, s), 4.88(1H, br), 5.02(2H, s), 5.70(1H, dd, J=17.7, 18.4 Hz), 6.75(1H, dd, J=17.7, 23.2 Hz), 6.87(1H, dd, J=2.4, 9.2 Hz), 6.92-6.96(2H, m), 7.10(1H, d, J=7.9), 7.14(1H, dd, J=1.8, 7.9 Hz), 7.23(1H, t, J=7.9 Hz), 7.30-7.41(6H, m).

Example 263

3-amino-[4-(3-benzyloxyphenylthio)-2-chlorophenyl]-3-hydroxymethyl-1-hexenylphosphonic acid

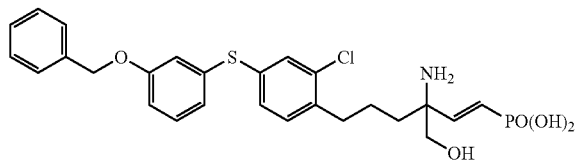

The compound of Example 262 was reacted in the same manner as in Example 236 to obtain the desired product as a colorless powder.

FABMS: 534([M+H]$^+$).

$^1$H-NMR(400 MHz, DMSOd$_6$) δ 1.46-1.74(4H, m), 2.57-2.61(2H, m), 3.47-3.52(2H, m), 5.07(2H, s), 5.87-5.96(1H, m), 6.03-6.16(1H, m), 6.87(1H, d, J=7.3 Hz), 6.95-6.97(2H, m), 7.19(1H, d, J=9.0 Hz), 7.27-7.39(8H, m), 7.81-8.83(2H, br).

m.p.=243-246° C.

Example 264

Dimethyl 6-[4-(3-benzyloxyphenylthio)-2-chlorophenyl]-3-t-butoxycarbonylamino-3-methoxymethyloxymethylhexylphosphonate

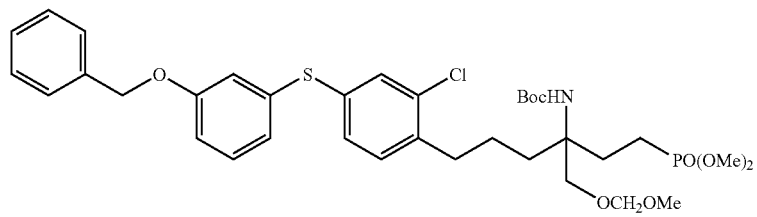

The compound of Example 262 was reacted in the same manner as in Reference Example 123 to obtain the desired product as a colorless powder.

FABMS: 708([M+H]$^+$).

$^1$H-NMR(400 MHz, CDCl$_3$) δ 1.41(9H, s), 1.51-1.67(2H, m), 1.70-2.05(6H, m), 2.68(2H, t, J=7.9 Hz), 3.33(3H, s), 3.47-3.53(2H, m), 3.73(6H, d, J=11.0 Hz), 4.58(2H, s), 4.61 (1H, br), 5.02(2H, s), 6.88(1H, dd, J=1.8, 7.9 Hz), 6.92-6.96 (2H, m), 7.11(1H, d, J=7.9 Hz), 7.14(1H, dd, J=1.8, 7.9 Hz), 7.23(1H, t, J=7.9 Hz), 7.30-7.41(6H, m).

Example 265

3-amino-6-[4-(3-benzyloxyphenylthio)-2-chlorophenyl]-3-hydroxymethylhexylphosphonic acid

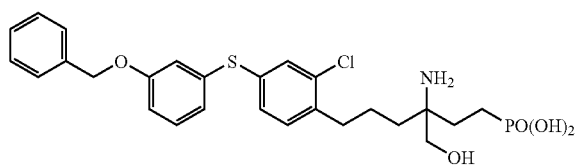

The compound of Example 264 was reacted in the same manner as in Example 236 to obtain the desired product as a colorless powder.

FABMS: 536([M+H]$^+$).

$^1$H-NMR(400 MHz, DMSOd$_6$) δ 1.36-1.73(8H, m), 2.60-2.68(2H, m), 3.31-3.40(2H, m), 5.07(2H, s), 6.88(1H, d, J=7.9 Hz), 6.96-6.98(2H, m), 7.20-7.40(9H, m), 7.94-8.94 (2H, br).

m.p.=193-196° C.

| Elemental analysis (%): C$_{26}$H$_{31}$ClNO$_5$PS•1H$_2$O | | | |
|---|---|---|---|
| | C | H | N |
| Calcd: | 56.36 | 6.00 | 2.53 |
| Found: | 56.18 | 5.61 | 2.51 |

Example 266

Dimethyl 5-[4-(3-benzyloxyphenylthio)-2-chlorophenyl]-3-t-butoxycarbonylamino-3-methoxymethyloxymethyl-1-pentenylphosphonate

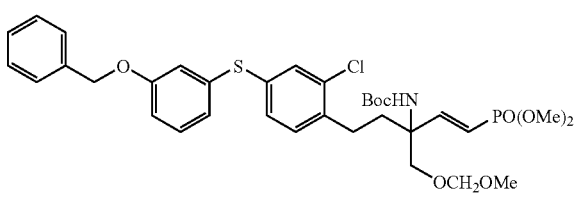

Following the same procedure as in Example 193, the compound of Example 219 was oxidized and, following the same procedure as in Example 232, the product was reacted with methyl methylenebisphosphonate to obtain the desired product as a colorless oil.

FABMS: 692([M+H]$^+$).

$^1$H-NMR(400 MHz, CDCl$_3$) δ 1.45(9H, s), 2.10-2.17(2H, m), 2.66-2.73(2H, m), 3.36(3H, s), 3.67-3.78(2H, m), 3.73 (6H, d, J=11.0 Hz), 4.63(2H, s), 4.80-4.85(1H, br), 5.02(2H, s), 5.78(1H, dd, J=17.8, 18.3 Hz), 6.82(1H, dd, J=17.8, 24.2 Hz), 6.87-6.95(3H, m), 7.12-7.13(2H, m), 7.23(1H, t, J=7.9 Hz), 7.30-7.41(6H, m).

Example 267

3-amino-5-[4-(3-benzyloxyphenylthio)-2-chlorophenyl]-3-hydroxymethyl-1-pentenylphosphonic acid

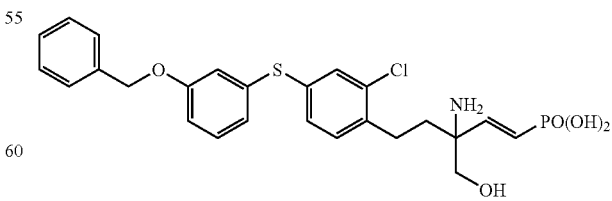

The compound of Example 266 was reacted in the same manner as in Example 236 to obtain the desired product as a colorless powder.

FABMS: 520([M+H]$^+$).

¹H-NMR(400 MHz, DMSOd₆) δ 1.76-1.98(2H, br), 2.50-2.72(2H, br), 3.47-3.70(3H, m), 5.05(2H, s), 6.03-6.11(1H, m), 6.21-6.33(1H, m), 6.85(1H, d, J=7.4 Hz), 6.94(2H, m), 7.15-7.36(9H, m), 8.74(2H, br s).
m.p.=245-248° C.

Example 268

Dimethyl 5-[4-(3-benzyloxyphenylthio)-2-chlorophenyl]-3-t-butoxycarbonylamino-3-methoxymethyloxymethylpentylphosphonate

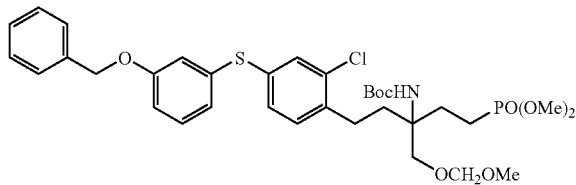

The compound of Example 266 was reacted in the same manner as in Reference Example 123 to obtain the desired product as a colorless oil.

FABMS: 694([M+H]⁺).

¹H-NMR(400 MHz, CDCl₃) δ 1.44(9H, s), 1.54-1.60(2H, m), 1.82-1.87(2H, m), 1.98-2.05(2H, m), 2.67-2.70(2H, m), 3.39(3H, s), 3.58-3.64(2H, m), 3.74(6H, d, J=11.0 Hz), 4.64 (2H, s), 4.74(1H, br), 5.02(2H, s), 6.87(1H, dd, J=1.8, 7.9 Hz), 6.91-6.95(2H, m), 7.10-7.15(2H, m), 7.23(1H, t, J=7.9 Hz), 7.31-7.41(6H, m).

Example 269

3-amino-5-[4-(3-benzyloxyphenylthio)-2-chlorophenyl]-3-hydroxymethylpentylphosphonic acid

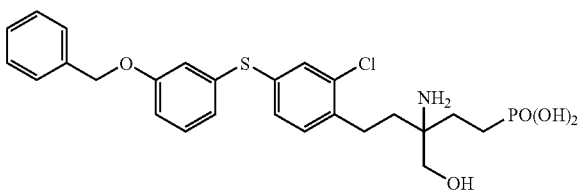

The compound of Example 268 was reacted in the same manner as in Example 236 to obtain the desired product as a colorless oil.

FABMS: 522([M+H]⁺).

¹H-NMR(400 MHz, DMSOd₆) δ 1.45-1.58(2H, m), 1.69-1.91(4H, m), 2.58-2.72(2H,m), 3.10-3.75(2H, br), 5.07(2H, s), 6.88(1H, d, J=7.3 Hz), 6.96-6.99(2H, m), 7.21(1H, d, J=7.9 Hz), 7.27-7.40(8H, m), 7.93-9.02(2H, br).
m.p.=205-208° C.

| Elemental analysis (%): $C_{25}H_{29}ClNO_5PS \cdot H_2O$ | | | |
|---|---|---|---|
| | C | H | N |
| Calcd: | 55.60 | 5.79 | 2.59 |
| Found: | 55.21 | 5.40 | 2.68 |

Example 270

(+)-2-amino-4-[4-(3-benzyloxyphenylthio)-2-chlorophenyl]-2-hydroxymethylbutylphosphonate monoester ((+)-Example 237)

Example 245 (250 mg) was dissolved in a 10% hydrochloric acid-methanol solution (10 mL) and the mixture was allowed to stand overnight. Subsequently, the solvent was removed by distillation and the residue was dissolved in ethyl acetate, followed by addition of triethylamine to adjust the pH to 7. The crystallized triethylamine hydrochloride was separated by filtration and was washed with ethyl acetate. The solvent was removed by distillation to give a Boc-free product as a colorless oil (250 mg). This product was dissolved in acetonitrile (5 mL) while the solution was chilled in an ice bath. To this solution, trimethylsilyl iodide (26.7 μL) was added and the mixture was stirred for 30 min at the same temperature. Subsequently, the solvent was removed by distillation and the residue was purified on a silica gel column chromatography (reversed phase silica chromatography, water:acetonitrile=9:1 to 6:1 to 3:1 to 1:1 to only acetonitrile) to give the desired product as a colorless powder (97 mg).

$[\alpha]^{25° C.}=+2.77(c=1.00, DMSO)$

FABMS: 524([M+H]⁺).

¹H-NMR(400 MHz, DMSO+TFA) δ 1.78-1.85(2H, m), 2.78-2.80(2H, m), 3.56(1H, d, J=11.0 Hz), 3.61(1H, d, J=11.0 Hz), 3.97(2H, d, J=5.5 Hz), 5.08(2H, s), 6.87-6.98(3H, m), 7.20-7.38(9H, m).

| Elemental analysis (%): $C_{24}H_{27}ClNO_6PS \cdot H_2O$ | | | |
|---|---|---|---|
| | C | H | N |
| Calcd: | 53.56 | 5.25 | 2.60 |
| Found: | 53.21 | 5.25 | 2.41 |

Example 271

(−)-2-amino-4-[4-(3-benzyloxyphenylthio)-2-chlorophenyl]-2-hydroxymethylbutylphosphonic acid monoester ((−)-Example 237)

Using the compound of Example 246, the reaction was carried out in the same manner as in Example 270 to obtain the desired product as a colorless powder.

$[\alpha]^{25° C.}=-2.61(c=1.00, DMSO)$.

FABMS: 524([M+H]⁺).

¹H-NMR(400 MHz, DMSO+TFA) δ 1.76-1.85(2H, m), 2.68-2.78(2H, m), 3.57(1H, d, J=11.0 Hz), 3.60(1H, d, J=11.0 Hz), 3.97(2H, d, J=5.5 Hz), 5.08(2H, s), 6.87-6.98(3H, m), 7.20-7.38(9H, m).

Example 272

Ethyl 5-[4-(3-benzyloxyphenylthio)-2-chlorophenyl]-2-methoxycarbonylamino-2-propylpentanoate

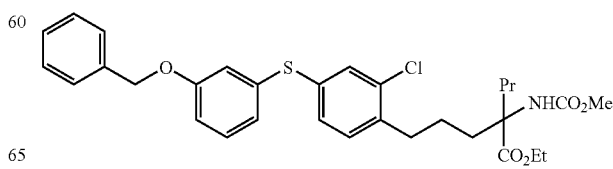

Using diethyl propylmalonate, the compound of Reference Example 252 was reacted in the same manner as in Example 194 to obtain ethyl 5-[4-(3-benzyloxyphenylthio)-2-chlorophenyl]-2-ethoxycarbonyl-2-propylpentanoate as a yellow oil. This product was hydrolyzed as in Example 198 to obtain a half ester. The half ester was treated in the same manner as in Example 202 to obtain the desired product as a colorless oil.

$^1$H-NMR(400 MHz, CDCl$_3$) δ 0.87(3H, t, J=7.3 Hz), 0.89-1.02(1H, m), 1.24(3H, t, J=7.3 Hz), 1.23-1.33(2H, m), 1.52-1.78(3H, m), 2.24-2.40(2H, m), 2.63-2.68(2H, m), 3.62(3H, s), 4.17-4.22(2H, m), 5.02(2H, s), 5.79(1H, br s), 6.85-6.94(3H, m), 7.09(1H, d, J=7.9 Hz), 7.14(1H, dd, J=1.8, 7.9 Hz), 7.22(1H, t, J=7.9 Hz), 7.29-7.43(6H, m).

Example 273

5-[4-(3-benzyloxyphenylthio)-2-chlorophenyl]-2-methoxycarbonylamino-2-propylpentane-1-ol

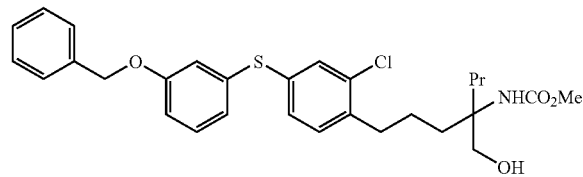

Using the compound of Example 272, the reaction was carried out in the same manner as in Example 76 to obtain the desired product as a colorless oil.

FABMS: 528([M+H]$^+$).

$^1$H-NMR(400 MHz, CDCl$_3$) δ 0.90(3H, t, J=7.3 Hz), 1.15-1.35(2H, m), 1.48-1.69(6H, m), 2.69(2H, t, J=7.3 Hz), 3.62(3H, s), 3.70(2H, s), 4.71(1H, br s), 5.01(2H, s), 6.85-6.94(3H, m), 7.12-7.24(3H, m), 7.31-7.40(6H, m).

Example 274

5-[4-(3-benzyloxyphenylthio)-2-chlorophenyl]-2-t-butoxycarbonylamino-2-propylpentane-1-ol

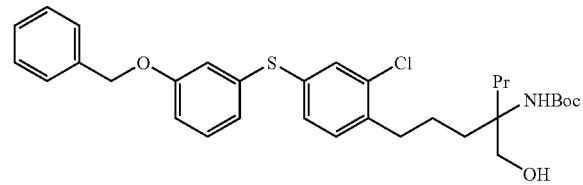

Using the compound of Example 273, the reaction was carried out in the same manner as in Example 226 to synthesize 2-amino-5-[4-(3-benzyloxyphenylthio)-2-chlorophenyl]-2-propylpentane-1-ol. As in Example 229, the product was reacted to form a Boc product, thereby obtaining the desired compound as a colorless oil.

$^1$H-NMR(400 MHz, CDCl$_3$) δ 0.90(3H, t, J=7.3 Hz), 1.15-1.35(2H, m), 1.42(9H, s), 1.48-1.73(6H, m), 2.70(2H, t, J=7.3 Hz), 3.63-3.66(2H, m), 4.51(1H, br s), 5.02(2H, s), 6.86-6.95(3H, m), 7.12-7.24(3H, m), 7.33-7.41(6H, m).

Examples 275 and 276

(+) and (−)-5-[4-(3-benzyloxyphenylthio)-2-chlorophenyl]-2-t-butoxycarbonylamino-2-propylpentane-1-ols The compound of Example 274 was optically resolved by HPLC (chiralpak OD-H, hexane:ethanol=97:3, detection wavelength=UV 254 nm, flow rate=3 mL/min). The desired products were obtained from the first eluate (Example 275) and the second eluate (Example 276), respectively, each as a colorless oil.

Example 275 [α]$^{25}_D$ −10.2° (C=1.08, CHCl$_3$);
Example 276 [α]$^{23}_D$ +9.48° (C=1.16, CHCl$_3$).

Example 277

5-[4-(3-benzyloxyphenylthio)-2-chlorophenyl]-2-t-butoxycarbonylamino-2-propylpentanal

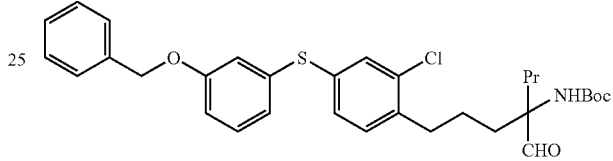

Using the compound of Example 274, the reaction was carried out in the same manner as in Example 193 to obtain the desired product as a colorless oil.

$^1$H-NMR(400 MHz, CDCl$_3$) δ 0.88(3H, t, J=7.3 Hz), 1.03-1.37(2H, m), 1.42(9H, s), 1.48-1.77(4H, m), 2.02-2.25(2H, m), 2.65-2.70(2H, m), 5.02(2H, s), 5.27(1H, br s), 6.86-6.94(3H, m), 7.07-7.14(2H, m), 7.23(1H, t, J=7.8 Hz), 7.30-7.41(6H, m), 9.23(1H, s).

Example 278

Dimethyl 6-[4-(3-benzyloxyphenylthio)-2-chlorophenyl]-3-t-butoxycarbonylamino-3-propyl-1-hexenylphosphonate

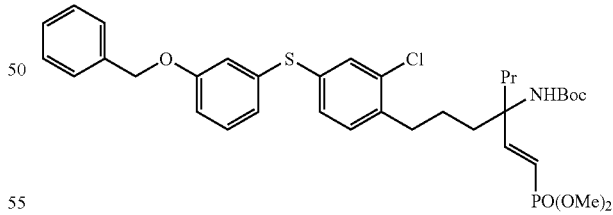

As in Example 232, the compound of Example 277 was reacted with methyl methylenebisphosphonate to obtain the desired product as a colorless oil.

FABMS: 674([M+H]$^+$).

$^1$H-NMR(400 MHz, CDCl$_3$) δ 0.88(3H, t, J=7.3 Hz), 1.17-1.23(2H, m), 1.40(9H, s), 1.51-1.87(6H, m), 2.68(2H, t, J=7.9 Hz), 3.69(3H, d, J=11.0 Hz), 3.70(1H, d, J=11.0 Hz), 4.47(1H, br), 5.02(2H, s), 5.59(1H, t, J=17.7 Hz), 6.65(1H, dd, J=23.3, 17.1 Hz), 6.86-6.89(3H, m), 7.09-7.15(2H, m), 7.23(1H, t, J=7.9 Hz), 7.31-7.41(6H, m).

Example 279

Dimethyl 6-[4-(3-benzyloxyphenylthio)-2-chlorophenyl]-3-t-butoxycarbonylamino-3-propylhexylphosphonate

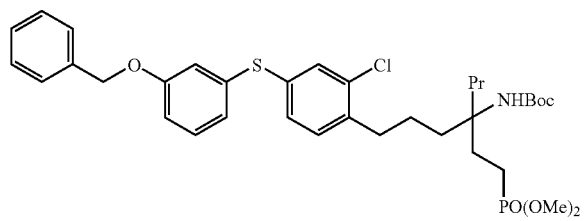

Using the compound of Example 278, the reaction was carried out in the same manner as in Reference Example 123 to obtain the desired product as a colorless oil.

FABMS: 676([M+H]$^+$).

$^1$H-NMR(400 MHz, CDCl$_3$) δ 0.88(3H, t, J=7.3 Hz), 1.15-1.28(2H, m), 1.40(9H, m), 1.51-2.02(10H, m), 2.67(2H, t, J=7.9 Hz), 3.72(6H, d, J=11.0 Hz), 4.13(1H, br), 5.02(2H, s), 6.87-6.95(3H, m), 7.10-7.25(3H, m), 7.32-7.39(6H, m).

Example 280

Dimethyl 3-amino-6-[4-(3-benzyloxyphenylthio)-2-chlorophenyl]-3-propyl-1-hexenylphosphonate hydrochloride

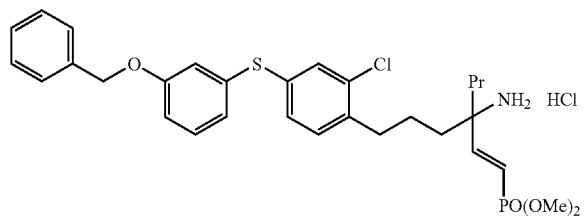

Using the compound of Example 278, the reaction was carried out in the same manner as in Example 233 to obtain the desired product as a colorless oil.

FABMS: 574([M+H]$^+$).

$^1$H-NMR(400 MHz, DMSOd$_6$) δ 0.85(3H, t, J=7.3 Hz), 1.15-1.28(2H, m), 1.53-1.76(6H, m), 2.66(2H, t, J=7.9 Hz), 3.59(3H, d, J=11.0 Hz), 3.62(3H, d, J=11.0 Hz), 5.08(2H, s), 6.00(1H, t, J=17.7 Hz), 6.57(1H, dd, J=23.8, 17.7 Hz), 6.89-7.00(3H, m), 7.22-7.41(9H, m), 8.47(3H, br s).

Examples 281 and 282

Dimethyl (+)- and (−)-3-amino-6-[4-(3-benzyloxyphenylthio)-2-chlorophenyl]-3-propyl-1-hexenylphosphonate hydrochlorides Using the compound of Example 275, the same procedures as in Examples 277, 278 and 280 were sequentially followed to obtain the desired product as a pale yellow amorphous compound ([α]$^{28.2}_D$+2.9° (C=1.0, MeOH)) (Example 281). Furthermore, using the compound of Example 276, the same procedure was followed as in Example 281 to obtain the desired product as a pale yellow amorphous compound ([α]$^{28.1}_D$−1.9° (C=1.0, MeOH)) (Example 282).

Example 283

3-amino-6-[4-(3-benzyloxyphenylthio)-2-chlorophenyl]-3-propyl-1-hexenylphosphonic acid

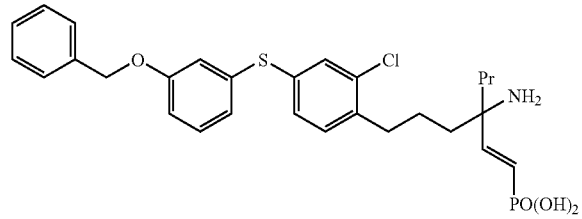

Using the compound of Example 278, the reaction was carried out in the same manner as in Example 236 to obtain the desired product as a colorless powder.

FABMS: 546([M+H]$^+$).

$^1$H-NMR(400 MHz, DMSOd$_6$) δ 0.85(3H, t, J=7.3 Hz), 1.19-1.21(2H, m), 1.51-1.69(6H, m), 2.67(2H, t, J=7.9 Hz), 5.08(2H, s), 5.87(1H, dd, J=17.7, 15.2 Hz), 6.32(1H, dd, J=23.8, 17.7 Hz), 6.88-7.00(3H, m), 7.22-7.41(9H, m).

| Elemental analysis (%): C$_{28}$H$_{33}$ClNO$_4$PS•2/3H$_2$O | | | |
|---|---|---|---|
| | C | H | N |
| Calcd: | 60.26 | 6.20 | 2.51 |
| Found: | 60.11 | 5.91 | 2.32 |

Example 284

3-amino-6-[4-(3-benzyloxyphenylthio)-2-chlorophenyl]-3-propylhexylphosphonic acid

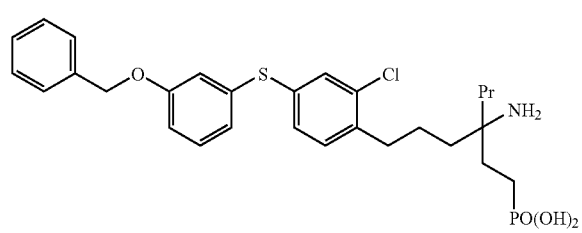

Using the compound of Example 279, the reaction was carried out in the same manner as in Example 236 to obtain the desired product as a colorless powder.

FABMS: 548([M+H]$^+$).

$^1$H-NMR(400 MHz, DMSOd$_6$) δ 0.85(3H, t, J=7.3 Hz), 1.18-1.21(2H, m), 1.42-1.54(8H, m), 1.68-1.74(2H, m), 2.67 (2H, br s), 5.08(2H, s), 6.88-7.00(3H, m), 7.22-7.41(9H, m).

| Elemental analysis (%): C$_{28}$H$_{35}$ClNO$_4$PS•H$_2$O | | | |
|---|---|---|---|
| | C | H | N |
| Calcd: | 59.41 | 6.59 | 1.83 |
| Found: | 59.05 | 6.14 | 2.29 | m.p. = 197-199° C.

Example 285

4-[4-(3-benzyloxyphenylthio)-2-chlorophenyl]pro-pyl-4-ethoxyphosphorylmethyl-2-oxazolidinone

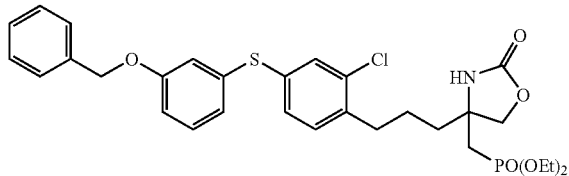

The compound of Example 188 (330 mg) was dissolved in triethyl phosphite (120 μL) and the solution was refluxed for 3 hours. Subsequently, the reaction mixture was purified on a silica gel column chromatography (hexane:ethyl acetate=1:1 to 1:5) to give the desired product as a pale yellow oil (320 mg).

FABMS: 604([M+H]$^+$).

$^1$H-NMR(400 MHz, CDCl$_3$) δ 1.31-1.35(6H, m), 1.59-1.72(2H, m), 1.84-1.88(2H, m), 2.10(1H, d, J=19.0 Hz), 2.11 (1H, d, J=19.0 Hz), 2.74(2H, t, J=7.3 Hz), 4.06-4.14(5H, m), 4.17-4.20(1H, m), 5.03(2H, s), 5.89(1H, br s), 6.88(1H, dd, J=1.2, 7.3 Hz), 6.94-6.97(2H, m), 7.10(1H, d, J=7.9 Hz), 7.14(1H, dd, J=1.8, 7.9 Hz), 7.24(1H, t, J=7.9 Hz), 7.31-7.41 (6H, m).

Example 286

2-amino-5-[4-(3-benzyloxyphenylthio)-2-chlorophenyl]-2-hydroxymethylpentylphosphonate hydrochloride

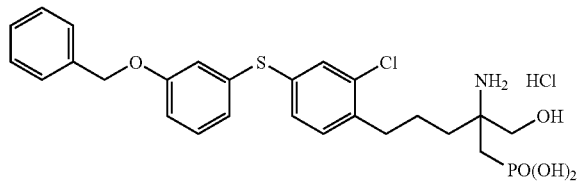

The compound of Example 285 was reacted in the same manner as in Example 190 and the resulting compound was reacted in the same manner as in Example 233 to obtain the desired product as a colorless powder.

FABMS: 522([M+H]$^+$).

$^1$H-NMR(400 MHz, DMSOd$_6$) δ 1.54-1.62(2H, m), 1.72-1.78(2H, m), 2.64-2.66(2H, m), 3.20-3.31(2H, m), 3.43-3.52 (2H, m), 5.08(2H, s), 6.88-6.90(1H, m), 6.94-7.00(2H, m), 7.21-7.24(1H, dd, J=2.5, 7.9 Hz), 7.29-7.41(8H, m).

m.p.=98-101° C.

| Elemental analysis (%): C$_{25}$H$_{29}$ClNO$_5$PS•HCl | | | |
|---|---|---|---|
| | C | H | N |
| Calcd: | 53.77 | 5.41 | 2.51 |
| Found: | 54.18 | 5.29 | 2.49 |

Example 287

Dimethyl 7-[4-(3-benzyloxyphenylthio)-2-chlorophenyl]-3-t-butoxycarbonylamino-3-t-butyldimethylsiloxymethyl-1-heptenylphosphonate

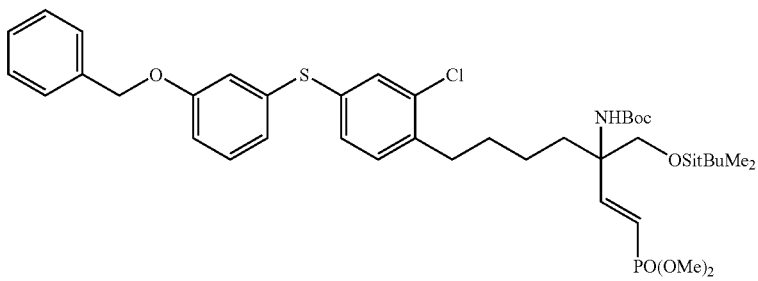

The compound of Example 130 was reacted with t-BuMe$_2$SiCl in the same manner as in Example 191. The resulting silyl product was oxidized in the same manner as in Example 193 to obtain an aldehyde. Subsequently, this aldehyde was reacted with methyl methylenebisphosphonate in the same manner as in Example 232 to obtain the desired product as a pale yellow oil.

FABMS: 790([M+H]$^+$).

$^1$H-NMR(400 MHz, CDCl$_3$) δ 0.04(6H, s), 0.89(9H, s), 1.30-1.37(2H, m), 1.41(9H, s), 1.50-1.60(2H, m), 1.75-1.85 (2H, m), 2.68(2H, t, J=7.3 Hz), 3.64-3.70(2H, m), 3.71(6H, d, J=11.6 Hz), 4.77(1H, br s), 5.02(2H, s), 5.67(1H, dd, J=17.1, 18.3 Hz), 6.72(1H, dd, J=17.1, 22.6 Hz), 6.67-6.88(1H, m), 6.91-6.94(2H, m), 7.11(1H, d, J=7.9 Hz), 7.14(1H, dd, J=1.8, 7.9 Hz), 7.22(1H, t, J=7.9 Hz), 7.31-7.39(6H, m).

Example 288

Dimethyl 7-[4-(3-benzyloxyphenylthio)-2-chlorophenyl]-3-t-butoxycarbonylamino-3-hydroxymethylheptylphosphonate

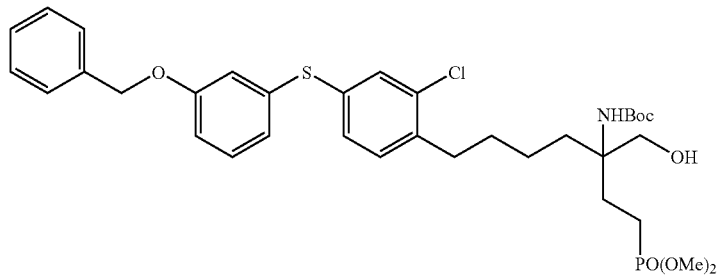

The compound of Example 287 was reduced in the same manner as in Reference Example 123 and the resulting compound (107 mg) was dissolved in tetrahydrofuran (5.0 mL). A 1 mol/L TBAF-tetrahydrofuran solution (160 μL) was added dropwise and the mixture was stirred for 3 hours at room temperature. Subsequently, water was added and the reaction mixture was extracted with ethyl acetate. The extract was washed sequentially with water and a saturated aqueous solution of sodium chloride and the organic phase was dried over anhydrous sodium sulfate. The solvent was removed by distillation and the residue was purified on a silica gel column chromatography (ethyl acetate only) to obtain the desired product as a colorless oil (47 mg).

FABMS: 678([M+H]$^+$).

$^1$H-NMR(400 MHz, CDCl$_3$) δ 1.42(9H, s), 1.25-1.38(6H, s), 1.70-1.80(2H, m), 1.83-1.95(2H, m), 2.70(2H, t, J=7.9 Hz), 3.62(2H, br s), 3.75(6H, d, J=11.0 Hz), 4.63(1H, br s), 5.02(2H, s), 6.86-6.89(1H, m), 6.92-6.94(2H, m), 7.10-7.16 (2H, m), 7.21-7.23(1H, m), 7.30-7.40(6H, m).

Example 289

3-amino-[4-(3-benzyloxyphenylthio)-2-chlorophenyl]-3-hydroxymethylheptylphosphonic acid

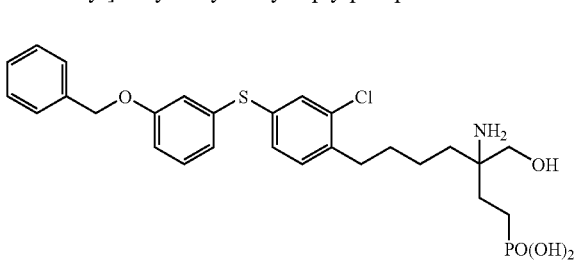

Using the compound of Example 288, the reaction was carried out in the same manner as in Example 236 to obtain the desired product as a colorless powder.

FABMS: 550([M+H]$^+$).

$^1$H-NMR(400 MHz, DMSOd$_6$) δ 1.22-1.32(2H, m), 1.48-1.60(6H, m), 1.68-1.76(2H, m), 2.64-2.68(2H, m), 3.39-3.50 (2H, m), 5.08(2H, s), 6.88-6.90(1H, m), 6.95-6.99(2H, m), 7.20(1H, dd, J=1.9, 9.8 Hz), 7.28-7.40(8H, m).

m.p.=180-183° C.

Example 290

3-amino-[4-(3-benzyloxyphenylthio)-2-chlorophenyl]-3-hydroxymethyl-1-heptenylphosphonic acid Following the same procedure as in Example 244, the compound of Example 287 was desilylated and the resulting product was reacted in the same manner as in Example 236 to obtain the desired product as a colorless powder.

FABMS: 548([M+H]$^+$).

$^1$H-NMR(400 MHz, DMSOd$_6$) δ 1.27-1.38(2H, m), 1.43-1.52(2H, m), 1.61-1.72(2H, m), 2.53-2.66(2H, m), 3.46-3.58

(2H, m), 5.02(2H, s), 5.88-5.97(1H, m), 6.06-6.17(1H, m), 6.85-6.87(1H, m), 6.94-6.96(2H, m), 7.15-7.17(1H, m), 7.26-7.38(8H, m).

m.p.=258-260° C.

Example 291

Diethyl 6-[4-(3-benzyloxyphenylthio)-2-chlorophenyl]-3-t-butoxycarbonylamino-3-t-butyldimethylsilyloxy-1,1-difluoro-2-hydroxyhexylphosphonate

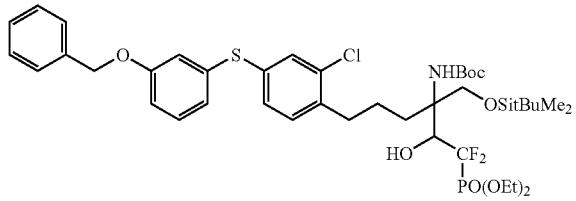

The compound of Example 128 was reacted with t-BuMe$_2$SiCl in the same manner as in Example 191. The resulting silyl product was oxidized in the same manner as in Example 193 to obtain an aldehyde. This aldehyde was reacted as follows: a 1.58 mol/L-LDA-tetrahydrofuran solution (1.50 mL) was added to a tetrahydrofuran solution (9 mL) while the mixture was kept at −78° C. To the resulting mixture, diethyl difluoromethylphosphonate (372 μL) was added dropwise over 15 min and the mixture was stirred for 20 min. To this mixture, the aldehyde (490 mg) in tetrahydrofuran (1.0 mL) was added dropwise over 20 min while the internal temperature was kept at −73° C. or below. Subsequently, the mixture was stirred for 1.5 hours. A saturated aqueous solution of ammonium chloride was then added to the reaction mixture and the mixture was extracted with ethyl acetate. The extract was washed sequentially with water and a saturated aqueous solution of sodium chloride and the organic phase was dried over anhydrous sodium sulfate. The solvent was removed by distillation and the resulting residue was purified on a silica gel column chromatography (hexane:ethyl acetate=3:1) to obtain the desired product as a colorless oil (439 mg).

FABMS: 858([M+H]$^+$).

$^1$H-NMR(400 MHz, CDCl$_3$) δ 0.06(6H, s), 0.88(9H, s), 1.33-1.40(6H, m), 1.46(9H, s), 1.56-1.70(4H, m), 2.69(2H, t, J=7.3 Hz), 3.82-3.84(1H, m), 4.23-4.33(6H, m), 5.02(2H, s), 5.05(1H, br s), 6.85-6.88(1H, m), 6.91-6.95(2H, m), 7.12-7.14(2H, m), 7.22(1H, t, J=7.9 Hz), 7.31-7.40(6H, m).

Example 292

Diethyl 3-amino-6-[4-(3-benzyloxyphenylthio)-2-chlorophenyl]-1,1-difluoro-2-hydroxy-3-hydroxymethylhexylphosphonate hydrochloride

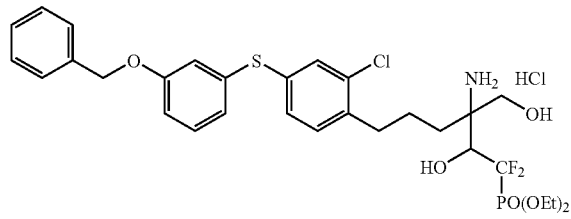

Following the same procedure as in Example 244, the compound of Example 291 was desilylated and the resulting product was reacted in the same manner as in Example 233 to obtain the desired product as a colorless amorphous product.

FABMS: 644([M+H]$^+$).

$^1$H-NMR(400 MHz, CDCl$_3$) δ 1.22-1.27(6H, m), 1.55-1.79(4H, m), 2.62-2.65(2H, m), 3.59-3.73(2H, m), 4.04-4.11(4H, m), 4.68-4.90(1H, m), 5.09(2H, s), 6.88-6.90(1H, m), 6.94-7.00(2H, m), 7.22-7.25(1H, m), 7.29-7.41(8H, m).

Example 293

3-amino-6-[4-(3-benzyloxyphenylthio)-2-chlorophenyl]-1,1-difluoro-2-hydroxy-3-hydroxymethylhexylphosphonic acid

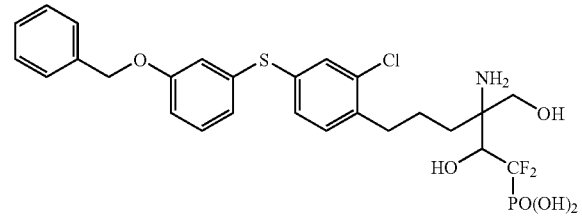

Using the compound of Example 292, the reaction was carried out in the same manner as in Example 236 to obtain the desired product as a colorless amorphous product.

FABMS: 588([M+H]$^+$).

$^1$H-NMR(400 MHz, DMSOd$_6$) δ 1.55-1.86(4H, m), 2.55-2.65(2H, m), 3.51-3.67(4H, m), 3.78-3.84(1H, m), 5.08(2H, s), 6.88(1H, d, J=7.9 Hz), 6.90-7.00(2H, m), 7.20-7.23(1H, m), 7.29-7.41(8H, m).

Example 294

Dimethyl 3-t-butoxycarbonylamino-3-t-butyldimethylsiloxymethyl-6-[2-chloro-4-(3-trifluoromethylphenoxy)phenyl]hexylphosphonate

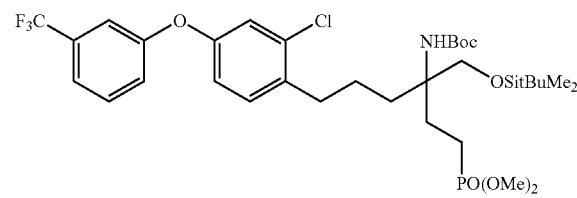

The compound of Example 149 was reacted with t-BuMe$_2$SiCl in the same manner as in Example 191. The resulting silyl product was oxidized in the same manner as in Example 193 to obtain an aldehyde. Subsequently, following the same procedure as in Example 232, this aldehyde was condensed with methyl methylenebisphosphonate and, following the same procedure as in Reference Example 123, the resulting product was reduced to give the desired product as a colorless oil.

$^1$H-NMR(400 MHz, CDCl$_3$) δ 0.04(6H, s), 0.88(9H, s), 1.42(9H, s), 1.56-1.64(4H, m), 1.64-1.77(2H, m), 1.90-1.97(2H, m), 2.69(2H, t, J=7.3 Hz), 3.49-3.58(2H, m), 3.73(6H, d, J=11.0 Hz), 4.47(1H, br s), 6.85(1H, dd, J=2.5, 8.6 Hz), 7.01(1H, d, J=2.5 Hz), 7.14-7.18(2H, m), 7.25-7.26(1H, m), 7.36(1H, t, J=7.9 Hz), 7.45(1H, t, J=7.9 Hz).

Example 295

Dimethyl 3-amino-6-[2-chloro-4-(3-trifluoromethylphenoxy)phenyl]-3-hydroxymethylhexylphosphonate hydrochloride

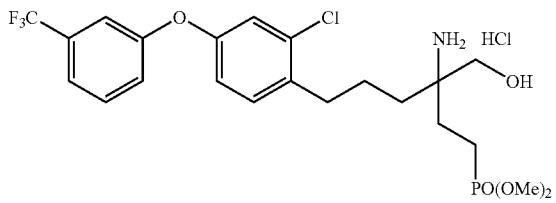

Following the same procedure as in Example 244, the compound of Example 294 was desilylated and the resulting product was reacted in the same manner as in Example 233 to obtain the desired product as a colorless amorphous product.

FABMS: 510([M+H]$^+$).

$^1$H-NMR(400 MHz, DMSOd$_6$) δ 1.54-1.64(4H, m), 1.67-1.80(4H, m), 2.65-2.69(2H, m), 3.40-3.41(2H, m), 3.68(6H, d, J=10.4 Hz), 5.51(1H, br s), 7.03(1H, dd, J=2.4, 8.6 Hz), 7.20(1H, d, J=2.4 Hz), 7.28-7.29(1H, m), 7.35(1H, s), 7.39 (1H, d, J=7.9 Hz), 7.51(1H, d, J=7.9 Hz), 7.63(1H, t, J=7.9 Hz), 7.91(3H, br s).

Example 296

3-amino-6-[2-chloro-4-(3-trifluoromethylphenoxy)phenyl]-3-hydroxymethylhexylphosphonic acid

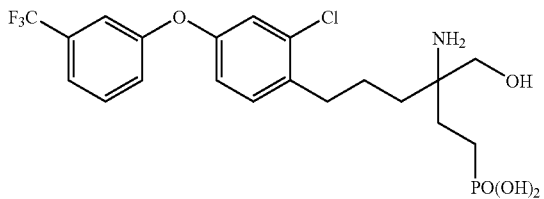

Using the compound of Example 295, the reaction was carried out in the same manner as in Example 236 to obtain the desired product as a colorless amorphous product.

FABMS: 482([M+H]$^+$).

$^1$H-NMR(400 MHz, DMSOd$_6$) δ 1.48-1.60(6H, m), 1.60-1.75(2H, m), 2.60-2.67(2H, m), 3.40(2H, s), 7.01(1H, dd, J=2.4, 7.9 Hz), 7.15-7.19(1H, m), 7.28(1H, d, J=7.9 Hz), 7.35(1H, s), 7.39(1H, d, J=7.9 Hz), 7.50(1H, d, J=7.9 Hz), 7.62(1H, t, J=7.9), 7.77-8.11(3H, br).

Example 297

Dimethyl 3-amino-6-[2-chloro-4-(3-trifluoromethylphenylthio)phenyl]-3-hydroxymethylhexylphosphonate hydrochloride

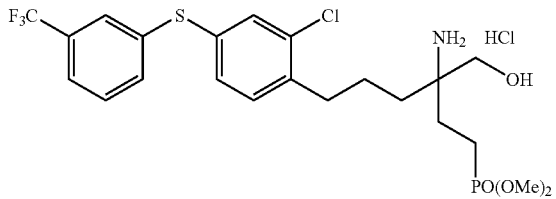

The compound of Example 76 was reacted in the same manner as in Example 294 and the resulting compound was reacted in the same manner as in Example 295 to obtain the desired product as a colorless oil.

FABMS: 525([M+H]$^+$).

$^1$H-NMR(400 MHz, DMSOd$_6$) δ 1.46-1.62(4H, m), 1.62-1.83(4H, m), 2.64-2.66(2H, m), 3.40-3.45(2H, m), 3.61(6H, d, J=10.4 Hz), 7.34(1H, dd, J=1.8, 8.0 Hz), 7.40-7.42(1H, m), 7.49(1H, dd, J=1.8 Hz), 7.54-7.56(1H, m), 7.59-7.62(2H, m), 7.66-7.68(1H, m), 7.86(3H, br s).

Example 298

2-t-butoxycarbonylamino-2-t-butyldimethylsiloxymethyl-5-[2-chloro-4-(3-trifluoromethylphenylthio)phenyl]-1-dimethoxyphosphoryloxypentane

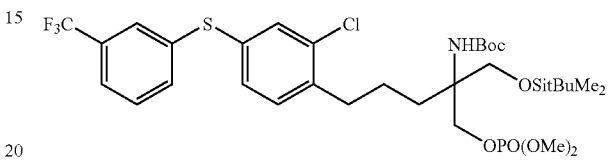

Following the same procedure as in Example 191, the compound of Example 76 was reacted with t-BuMe$_2$SiCl and, following the same procedure as in Example 223, the resulting silyl product was reacted to give the desired product as a colorless oil.

FABMS: 741([M+H]$^+$).

$^1$H-NMR(400 MHz, CDCl$_3$) δ 0.05(6H, s), 0.87(9H, s), 1.41(9H, s), 1.60-1.91(4H, m), 2.71(2H, t, J=7.9 Hz), 3.60 (1H, d, J=9.2 Hz), 3.64(1H, d, J=9.2 Hz), 3.76(6H, d, J=11.0 Hz), 4.09-4.15(2H, m), 4.66(1H, br), 7.14-7.20(2H, m), 7.30-7.55(5H, m).

Example 299

2-amino-5-[2-chloro-4-(3-trifluoromethylphenylthio)phenyl]-2-hydroxymethylpentylphosphonate monoester

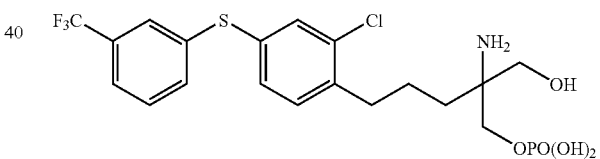

To a tetrahydrofuran solution (20 mL) of the compound of Example 298 (1.29 g), a 1 mol/L TBAF-tetrahydrofuran solution (2.09 mL) was added dropwise and the mixture was stirred for 4 hours at room temperature. Subsequently, water was added and the reaction mixture was extracted with ethyl acetate. The extract was washed sequentially with water and a saturated aqueous solution of sodium chloride and the organic phase was dried over anhydrous sodium sulfate. The solvent was removed by distillation and the residue was purified on a silica gel column chromatography (hexane:ethyl acetate=1:1 to ethyl acetate only) to obtain a desilylated product as a colorless oil (1.00 g). The resulting compound (1.00 g) was dissolved in a 10% hydrochloric acid-methanol solution (20 mL) and the mixture was left overnight at room temperature. Subsequently, the solvent was removed by distillation and the residue was dissolved in ethyl acetate. The solution was neutralized with triethylamine. The crystallized triethylamine hydrochloride was separated by filtration and the solvent was removed by distillation to give a colorless oil (1.00 g). The oil was dissolved in acetonitrile (15 mL) while the solution was chilled in an ice bath. To this solution, TMSI (905 μL) was added and the mixture was stirred for 60 min.

The reaction mixture was concentrated and was purified on a silica gel column chromatography (water:acetonitrile=9:1 to 6:1 to 3:1 to 1:1 to acetonitrile only) to obtain the desired product as a colorless powder (384 g).

FABMS: 500([M+H]$^+$).

$^1$H-NMR(400 MHz, DMSOd$_6$) δ 1.60(4H, br s), 2.66(2H, br s), 3.36-3.45(2H, m), 3.68-3.76(2H, m), 7.32(1H, dd, J=1.8, 8.5 Hz), 7.38-7.45(2H, m), 7.50-7.56(1H, m), 7.57-7.68(3H, m).

| Elemental analysis (%): C$_{19}$H$_{22}$ClF$_5$NO$_5$PS•1/4H$_2$O | | | |
|---|---|---|---|
| | C | H | N |
| Calcd: | 45.24 | 4.50 | 2.78 |
| Found: | 45.05 | 4.31 | 2.72 |

Example 300

2-amino-5-[2-chloro-4-(3-trifluoromethylphenoxy)phenyl]-2-hydroxymethylpentylphosphonate monoester

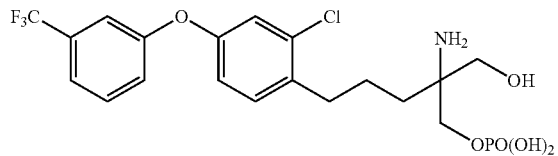

The compound of Example 149 was reacted in the same manner as in Example 298 and the resulting compound was reacted in the same manner as in Example 299 to obtain the desired product as a colorless powder.

FABMS: 484([M+H]$^+$).

$^1$H-NMR(400 MHz, DMSOd$_6$) δ 1.61(4H, br), 2.64(2H, br), 3.41(1H, d, J=11.6 Hz), 3.51(1H, d, J=11.6 Hz), 3.69-3.80(2H, m), 7.00(1H, dd, J=2.5, 8.6 Hz), 7.16(1H, d, J=2.5 Hz), 7.29(1H, dd, J=2.5, 8.6 Hz), 7.35(1H, s), 7.40(1H, d, J=8.6 Hz), 7.50(1H, d, J=8.0 Hz), 7.61(1H, t, J=8.0 Hz).

Example 301

2-amino-4-[2-chloro-4-(3-hydroxyphenylthio)phenyl]-2-hydroxymethylbutylphosphonate monoester

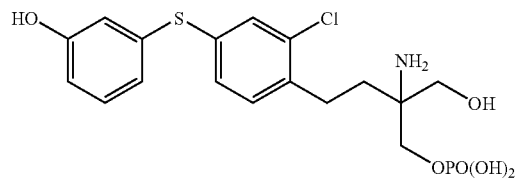

Using the compound of Example 223, the reaction was carried out in the same manner as in Example 238 to obtain the desired product as a colorless powder.

FABMS: 434([M+H]$^+$).

$^1$H-NMR(400 MHz, DMSOd$_6$) δ 1.72-1.92(2H, m), 2.63-2.82(2H, m), 3.48-3.60(2H, m), 3.71-3.90(2H, m), 6.66-6.78 (3H, m), 7.14-7.37(4H, m).

Example 302

2-t-butoxycarbonylamino-2-[2-chloro-4-(4-trifluoromethylphenoxy)phenyl]propyl-1,3-propanediol

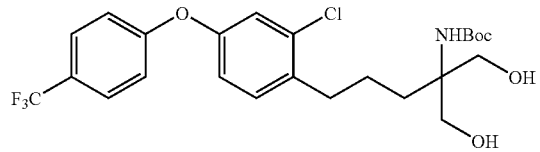

The compound of Reference Example 323 was reacted in the same manner as in Example 1 and the resulting compound was reduced in the same manner as in Example 76 to obtain the desired product as a colorless powder.

$^1$H-NMR(400 MHz, CDCl$_3$) δ 1.44(9H, s), 1.57-1.74(4H, m), 2.70(2H, t, J=6.7 Hz), 3.33(2H, br s), 3.61(2H, d,d, J=6.7, 11.6 Hz), 3.84(2H, d,d, J=6.7, 11.6 Hz), 4.93(1H, br s), 6.89 (1H, dd, J=2.5, 8.0 Hz), 6.98-7.07(3H, m), 7.21(1H, d, J=8.6 Hz), 7.59(2H, d, J=8.6 Hz).

Example 303

2-t-butoxycarbonylamino-2-[2-chloro-4-(2-trifluoromethylphenoxy)phenyl]propyl-1,3-propanediol

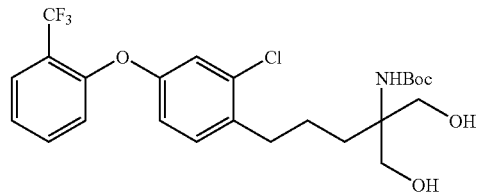

The compound of Reference Example 324 was reacted in the same manner as in Example 1 and the resulting compound was reduced in the same manner as in Example 76 to obtain the desired product as a colorless powder.

FABMS: 504([M+H]$^+$).

$^1$H-NMR(400 MHz, CDCl$_3$) δ 1.44(9H, s), 1.58-1.66(4H, m), 2.70(2H, t, J=6.7 Hz), 3.35(2H, br s), 3.60(2H, d,d, J=7.3, 11.6 Hz), 3.84(2H, d,d, J=7.3, 11.6 Hz), 4.92(1H, br s), 6.87 (1H, dd, J=2.5, 8.0 Hz), 6.96(1H, d, J=8.0 Hz), 7.03(1H, d=2.5 Hz), 7.15-7.22(2H, m), 7.48(1H, t, J=7.3 Hz), 7.68(1H, d, J=6.7 Hz).

Example 304

2-t-butoxycarbonylamino-2-[4-(4-benzyloxyphenylthio)-2-chlorophenyl]ethyl-1,3-propanediol

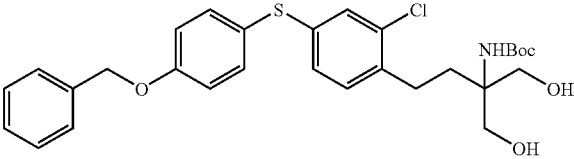

The compound of Reference Example 327 was reacted in the same manner as in Example 1 and the resulting compound was reduced in the same manner as in Example 76 to obtain the desired product as a colorless oil.

FABMS: 543([M+H]$^+$).

$^1$H-NMR(400 MHz, CDCl$_3$) δ 1.45(9H, s), 1.78-1.84(2H, m), 2.64-2.71(2H, m), 3.23-3.39(2H, m), 3.65(2H, d,d, J=6.7, 11.6 Hz), 3.84(2H, d,d, J=6.7, 11.6 Hz), 5.07(1H, s), 5.08(2H, s), 6.96-7.00(3H, m), 7.07-7.13(2H, m), 7.345-7.44(7H, m).

Example 305

Dimethyl 3-amino-6-[2-chloro-4-(4-trifluoromethylphenoxy)phenyl]-3-hydroxymethylhexylphosphonate hydrochloride

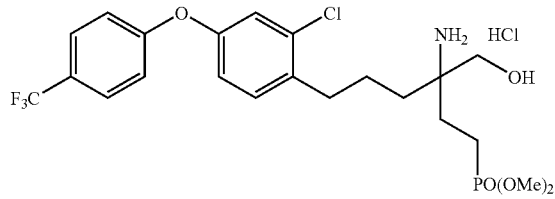

The compound of Example 302 was treated in the same manner as in Example 294 and the resulting compound was reacted in the same manner as in Example 295 to obtain the desired product as a colorless amorphous product.

FABMS: 510([M+H]$^+$).

$^1$H-NMR(400 MHz, DMSOd$_6$) δ 1.51-1.60(4H, m), 1.65-1.82(4H, m), 2.68(2H, br s), 3.42(2H, s), 3.61(6H, d, J=11.0 Hz), 7.08(1H, dd, J=2.4, 8.6 Hz), 7.15(2H, d, J=8.6 Hz), 7.26(1H, d, J=2.4 Hz), 7.42(1H, s, 8.6 Hz), 7.75(2H, d, 8.6 HzHz), 7.89(3H, br s).

Example 306

Dimethyl 3-amino-6-[2-chloro-4-(4-trifluoromethylphenoxy)phenyl]-3-hydroxymethyl-1-hexenylphosphonate hydrochloride

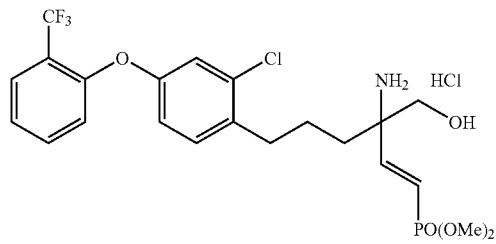

The compound of Example 303 was reacted in the same manner as in Example 287 and the resulting compound was desilylated in the same manner as in Example 244. The desilylated product was then reacted in the same manner as in Example 233 to obtain the desired product as an amorphous product.

FABMS: 508([M+H]$^+$).

$^1$H-NMR(400 MHz, DMSOd$_6$) δ 1.42-1.62(2H, m), 1.68-1.82(2H, m), 2.66(2H, t, J=2.7 Hz), 3.42(2H, br s), 3.60(6H, d, J=11.0 Hz), 6.00(1H, t, J=17.7 Hz), 6.56(1H, dd, J=17.7, 22.6 Hz), 6.97(1H, dd, J=2.5, 8.6 Hz), 7.11(1H, d, J=8.6 Hz), 7.13(1H, d=2.5 Hz), 7.32-7.40(2H, m), 7.67(1H, t, J=8.0 Hz), 7.79(1H, t, J=7.3 Hz), 8.22-8.38(3H, br s).

Example 307

Dimethyl 3-amino-6-[2-chloro-4-(4-trifluoromethylphenoxy)phenyl]-3-hydroxymethylhexylphosphonate hydrochloride

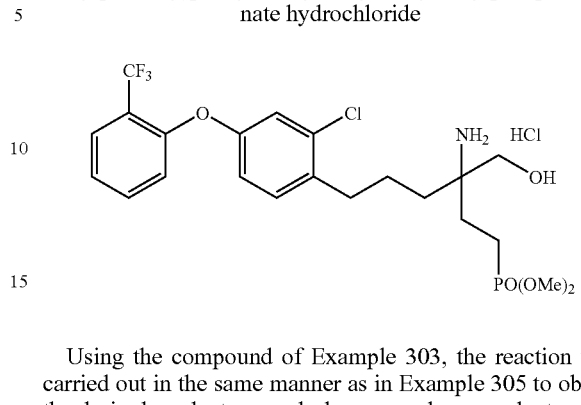

Using the compound of Example 303, the reaction was carried out in the same manner as in Example 305 to obtain the desired product as a colorless amorphous product.

FABMS: 510([M+H]$^+$).

$^1$H-NMR(400 MHz, DMSOd$_6$) δ 1.50-1.60(4H, m), 1.65-1.82(4H, m), 2.60-2.70(2H, m), 3.52-3.55(2H, m), 3.61(6H, d, J=11.0 Hz), 6.98(1H, dd, J=2.4, 8.6 Hz), 7.08(1H, d, J=8.6 Hz), 7.13(1H, d, J=2.4 Hz), 7.33-7.41(2H, m), 7.68(1H, t, J=7.3), 7.80(1H, d, J=7.3 Hz), 7.75-7.85(3H, br s).

Example 308

3-amino-5-[4-(4-benzyloxyphenylthio)-2-chlorophenyl]-3-hydroxymethylpentylphosphonic acid

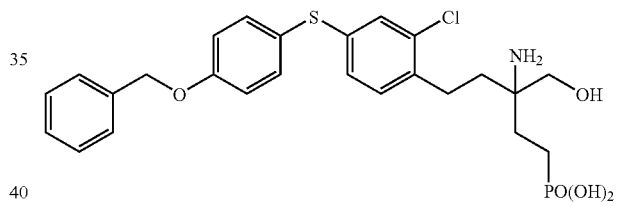

The compound of Example 304 was reacted in the same manner as in Example 294 and the resulting compound was reacted in the same manner as in Example 290 to obtain the desired product as a colorless powder.

FABMS: 522([M+H]$^+$).

$^1$H-NMR(400 MHz, DMSOd$_6$) δ 1.47-1.62(2H, m), 1.62-1.91(4H, m), 2.55-2.67(2H, m), 3.40-3.54(2H, m), 5.12(2H, s), 6.98-7.10(4H, m), 7.25-7.51(8H, m).

Example 309

2-amino-4-[4-(4-benzyloxyphenylthio)-2-chlorophenyl]-2-hydroxymethylbutylphosphonate monoester

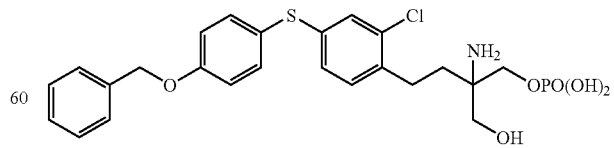

The compound of Example 304 was reacted in the same manner as in Example 298 and the resulting compound was reacted in the same manner as in Example 299 to obtain the desired product as a colorless powder.

FABMS: 524([M+H]$^+$).

$^1$H-NMR(400 MHz, DMSOd$_6$) δ 1.70-1.77(2H, m), 2.65-2.69(2H, m), 3.49-3.53(2H, m), 3.72-3.86(2H, m), 5.13(2H, s), 7.06-7.10(4H, m), 7.25-7.27(1H, m), 7.33-7.46(7H, m).

Next, some experiment examples will be described, that demonstrate the efficacy of the compound of the present invention.

Experiment Example 1

Test for the Ability of Test Compounds to Induce Intracellular Ca$^{2+}$ Mobilization in Cells Expressing Human S1P (sphingosine-1-phosphate) Receptors CHO cells expressing human S1P receptors (i.e., CHO cells expressing hS1P$_1$ receptors or hS1P$_3$ receptors) were subcultured on Ham's F-12 medium supplemented with 10% fetal bovine serum and 200 μg/mL Geneticin. The cells were seeded on a 96-well black clear bottom plate (COSTAR) at 4×10$^4$ cells/well and were cultured overnight at 37° C. in 5% CO$_2$. A fluorescent reagent that emits fluorescence upon binding to Ca$^{2+}$ (Calcium Screening Kit (DOJINDO)) was added to the culture and the cells were further cultured for 60 min at 37° C. in 5% CO$_2$. After culturing, microplate spectrofluorometer (FLEX station, MOLECULAR DEVICE) was used to measure the fluorescence intensity at an excitation wavelength of 485 nm and a detection wavelength of 525 nm. S1P or a test compound adjusted with cultural medium to a concentration 10 times higher than the final concentration (final DMSO concentration=0.1%). Each test compound solution was added 18 sec. after beginning of the measurement of fluorescence. The fluorescence intensity was measured every 1.5 sec for 100 sec. For each test compound, the difference between the maximum fluorescence intensity and the minimum fluorescence intensity (i.e., increase in fluorescence) was determined from the measurements. The rate of fluorescence increase (%) for each test compound was calculated by the difference (100%) of the fluorescence increase between solvent only and S1P (10$^{-6}$M). Using this value as an index of the ability of the test compound to induce intracellular Ca$^{2+}$ mobilization, EC50 was determined by PRISM software (GraphPad). In Table 11, the symbol "−" indicates that the test compound was determined to have an EC50 of 1 μmol/L or higher, the symbol "+" indicates that the test compound had an EC50 of lower than 1 μmol/L and higher than or equal to 0.1 μmol/L, the symbol "++" indicates that the test compound had an EC50 of lower than 0.1 μmol/L and higher than or equal to 0.01 μmol/L, and the symbol "+++" indicates that the test compound had an EC50 of lower than 0.01 μmol/L.

TABLE 11

| Example No. | S1P1 | S1P3 |
| --- | --- | --- |
| 236 | ++ | ++ |
| 237 | +++ | +++ |
| 238 | + | − |
| 239 | +++ | +++ |
| 240 | ++ | + |
| 241 | + | − |
| 242 | + | − |
| 249 | ++ | +++ |
| 250 | + | − |
| 253 | + | + |
| 254 | ++ | − |
| 260 | ++ | + |
| 261 | + | − |
| 263 | +++ | + |
| 265 | +++ | + |
| 267 | +++ | − |
| 269 | ++ | − |

TABLE 11-continued

| Example No. | S1P1 | S1P3 |
| --- | --- | --- |
| 280 | + | + |
| 283 | ++ | ++ |
| 284 | ++ | + |
| 286 | ++ | − |
| 290 | +++ | ++ |
| 293 | + | + |
| 296 | ++ | − |
| 299 | ++ | − |
| 300 | ++ | − |
| 307 | + | − |
| 308 | + | − |

These results indicate that the compounds of the present invention act on human S1P receptors.

Experiment Example 2

Test for the Ability of Test Compounds to Induce Activation of Extracellular Regulatory Kinase (ERK) in Cells Expressing Human S1P Receptors CHO cells expressing human S1P receptors (i.e., CHO cells expressing hS1P$_4$ receptors) were subcultured on Ham's F-12 medium supplemented with 10% fetal bovine serum and 200 μg/mL Geneticin. The cells were seeded on a 6-well cell culture plate (COSTAR) at 3×10$^5$ cells/well and were cultured overnight at 37° C. in 5% CO$_2$. On the following day, the medium was replaced with FBS-free Ham's F-12 medium (containing 0.1% fatty acid-free bovine serum albumin) and the cells were cultured overnight at 37° C. in 5% CO$_2$. S1P or a test compound adjusted with Ham's F-12 medium (with 0.1% fatty acid-free bovine serum albumin) to a concentration 10 times higher than the final concentration (final DMSO concentration=0.1%). Each test compound solution was added to this culture plate. The cells were cultured for 5 min at 37° C. in 5% CO$_2$. The medium was removed and the cells were washed with a 200 μmol/L ice-cold PBS containing Na$_3$VO$_4$. A lysis buffer (20 mmol/L Tris-HCl pH7.5, 1% Triton X-100, 1 mmol/L EDTA, 1 mmol/L EGTA, 0.5 mmol/L Na$_3$VO$_4$, 0.1% β-mercaptoethanol, 50 mmol/L NaF, 5 mmol/L Na$_4$O$_7$P$_3$, 10 mmol/L C$_3$H$_7$O$_6$Na, 1 μmol/L Microcystin LR, 1× complete Protease Inhibitor Cocktail (ROCHE)) was then added to the cells and the reaction was carried out on ice for 5 min to lyse the cells. The cell lysate was subjected to sodium dodecyl sulfate-polyacrylamide gel electrophoresis (SDS-PAGE) to separate proteins. The proteins were transferred to a PVDF membrane (Hybond-P, Amersham Biosciences). The membrane was reacted overnight at 4° C. with anti-phospho ERK (p42/44 MAPK) monoclonal antibody (E10, Cell Signaling Technologies) diluted 1000-fold, and was subsequently reacted for 1 hour at room temperature with alkaline phosphatase-labeled anti-mouse IgG antibody (Molecular Probe) diluted 6000-fold. After washing with 20 mmol/L Tris-HCl and 150 mmol/L NaCl solution, the PVDF membrane was fluorostained with DDAO phosphate (DyeChrome Western Blot Stain Kit, Molecular Probe), a fluorescent substrate of alkaline phosphatase. The fluorescence was detected using a variable image analyzer (Typhoon 8600, Amersham Biosciences). The detected signal of phosphorylated ERK was quantified using ImageQuant software (Molecular Dynamics). The rate of ERK activation (%) for each test compound was calculated by the difference (100%) of the signal intensity between solvent only and S1P ($10^{-6}$ mol/L). The results are shown in Table 12 below.

TABLE 12

| Example No. | Compound Conc. (nmol/L) | Induction effect of ERK activation on hS1P-expressing CHO cells (Activation rate (%) relative to the activated ERK at S1P10-6 mol/L) |
| --- | --- | --- |
| 236 | 1 | 8.0 |
|  | 10 | 119.5 |
| 237 | 1 | 35.8 |
|  | 10 | 80.7 |

These results indicate that the compounds of the present invention induce ERK activation by acting on human S1P receptors.

Experiment Example 3

Inhibitory effects of test compounds on host vs. graft rejection in mice

This experiment was performed according to the method described in *Transplantation* 55(3) (1993): 578-591. Spleens were collected from 6 to 16 week old male BALB/c mice (CHARLES RIVER JAPAN). The spleens were placed in an RPMI-1640 medium (SIGMA) and were gently pressed between two slide glasses and then passed through a cell strainer (70 μm, Falcon) to form a cell suspension. The suspension was then centrifuged and the supernatant was discarded. An ammonium chloride-Tris isotonic buffer was added to the suspension to lyse erythrocytes. The cells were then centrifuged three times in RPMI-1640 medium for washing and were resuspended in an RPMI-1640 medium. To this suspension, mitomycin C (KYOWA HAKKO KOGYO Co., Ltd.) was added to a final concentration of 25 μg/mL and the suspension was incubated for 30 minutes at 37° C. in a 5% $CO_2$ atmosphere. The cells were centrifuged three times in RPMI-1640 medium for washing and were resuspended in an RPMI-1640 medium so that the medium would contain $2.5 \times 10^8$ cells/mL. This suspension served as a "stimulation cell suspension." Using a 27G needle with a microsyringe (Hamilton), 20 μL ($5 \times 10^6$ cells/mouse) of the stimulation cell suspension was subcutaneously injected into the right hind footpad of 6 to 8 week old male C3H/HeN mice (CLEA JAPAN). Normal control group was injected with RPMI-1640 medium alone. 4 days after the injection, right popliteal lymph nodes were collected and were weighed on a Mettler AT201 electronic scale (METTLER TOLEDO Co., Ltd.). Each animal was intraperitoneally administered a test compound once a day for four consecutive days starting on the day of the injection of the stimulation cells (i.e., total of 4 times). Control groups were administered the same vehicle as that used in the preparation of each test compound. The results are shown in Table 13 below. The inhibition (%) was determined using the following formula {[Weight of right popliteal lymph nodes of positive control group]−[Weight of right popliteal lymph nodes of test compound group]×100}/{[Weight of right popliteal lymph nodes of positive control group]−[Weight of right popliteal lymph nodes of normal control group]}   Formula 1

TABLE 13

| Example No. | Dose (mg/kg) | Inhibition (%) |
| --- | --- | --- |
| 233 | 30 | 53 |
| 235 | 30 | 56 |
| 236 | 0.03 | 73 |
| 237 | 0.1 | 75 |
| 238 | 3 | 65 |
| 239 | 0.03 | 65 |
| 241 | 10 | 46 |
| 242 | 10 | 62 |
| 247 | 0.03 | 63 |

INDUSTRIAL APPLICABILITY

As set forth, the present invention has been devised in recognition of the fact that the novel aminophosphonic acid derivatives with a diarylsulfide or diarylether group exhibit a strong ability to modulate S1P receptors. Effective modulators of S1P receptors, the compounds of the present invention have a great potential as a prophylactic or therapeutic agent against peripheral vascular diseases, such as arteriosclerosis, arteriosclerosis obliterans, renal fibrosis, hepatic fibrosis, chronic bronchial asthma, diffuse pulmonary hamartoangiomyomatosis, adult respiratory distress syndrome (ARDS), chronic obstructive pulmonary disease (COPD), interstitial pneumonia, idiopathic interstitial pneumonia, lung cancer, hypersensitivity pneumonitis, Buerger's disease, diabetic neuropathy, septicemia, angiitis, nephritis, pneumonia, cerebral infarction, myocardial infarction, edema, varicose veins, dissecting arterial aneurysm, stenocardia, DIC, pleuritis, congestive heart failure, multiple organ failure, bed sore, burn, ulcerative colitis and Crohn's disease. The compounds of the present invention also act as effective prophylactic or therapeutic agents against rejection of heart transplants, kidney transplants, skin grafts, liver transplants and bone marrow transplants, or against rheumatoid arthritis, lupus nephritis, systemic lupus erythematosus, Hashimoto's disease, multiple sclerosis, myasthenia gravis, diabetes, atopic dermatitis, allergic rhinitis, allergic conjunctivitis, allergic contact dermatitis and various other diseases.

The invention claimed is:

1. An aminophosphonic acid derivative represented by the following general formula (1):

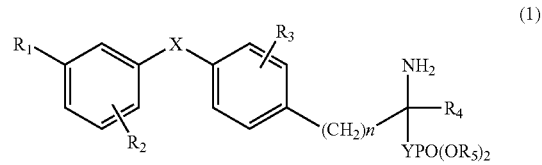

wherein $R_1$ is a hydrogen atom, a halogen atom, a halogenated or unhalogenated lower alkyl group having 1 to 4 carbon atoms, a hydroxy group, a phenyl group, an aralkyl group, a lower alkoxy group having 1 to 4 carbon atoms, a trifluoromethyloxy group, a substituted or unsubstituted phenoxy group, a cyclohexylmethyloxy group, a substituted or unsubstituted aralkyloxy group, a pyridylmethyloxy group, a cinnamyloxy group, a naphthylmethyloxy group, a phenoxymethyl group, a hydroxymethyl group, a hydroxyethyl group, a lower alkylthio group having 1 to 4 carbon atoms, a lower alkylsulfinyl group having 1 to 4 carbon atoms, a lower alkylsulfonyl group having 1 to 4 carbon atoms, a benzylthio group, an acetyl group, a nitro group or a cyano group; $R_2$ is a hydrogen atom, a halogen atom, a halogenated or unhalogenated lower alkyl group having 1 to 4 carbon atoms, a lower alkoxy group having 1 to 4 carbon atoms, an aralkyl group or an aralkyloxy group; $R_3$ is a hydrogen atom, a halogen atom, a trifluoromethyl group, a lower alkyl group having 1 to 4 carbon atoms, a lower alkoxy group having 1 to 4 carbon atoms, a hydroxy group, a benzyloxy group, a phenyl group, a lower alkoxymethyl group having 1 to 4 carbon atoms or a lower alkylthio group having 1 to 4 carbon atoms; $R_4$ is a hydrogen atom, a halogen atom, a lower alkyl group having 1 to 4 carbon atoms, a lower alkoxymethyl group having 1 to 4 carbon atoms, a lower alkylthiomethyl group having 1 to 4 carbon atoms, a hydroxymethyl group, a phenyl group or an aralkyl group; $R_5$ is a hydrogen atom or a lower alkyl group having 1 to 4 carbon atoms; X is O, S, SO or $SO_2$; Y is —$CH_2O$—, —$CH_2$—, —CH=CH—, —CH=CF—, —$CH_2CH_2$—, —$CH_2CHF$—, —$CH_2CF_2$— or —CH(OH)$CF_2$—; and n is an integer from 1 to 4, or an optical isomer, a pharmaceutically acceptable salt or a hydrate thereof.

2. The 2-aminophosphonic acid monoester derivative according to claim 1, or the optical isomer, the pharmaceutically acceptable salt or the hydrate thereof, wherein the compounds represented by the general formula (1) comprise compounds represented by the following general formula (1a):

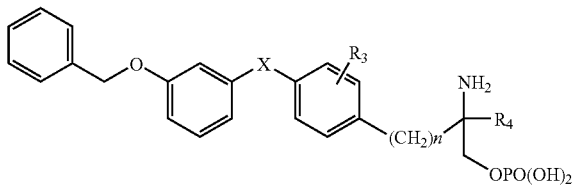

(1a)

wherein X, $R_3$, $R_4$ and n are as defined in claim 1.

3. The 2-aminophosphonic acid monoester derivative according to claim 2, or the optical isomer, the pharmaceutically acceptable salt or the hydrate thereof, wherein $R_3$ is a chlorine atom.

4. The 3-aminophosphonic acid derivative according to claim 1, or the optical isomer, the pharmaceutically acceptable salt or the hydrate thereof, wherein the compound represented by the general formula (1) comprise compounds represented by the following general formula (1b):

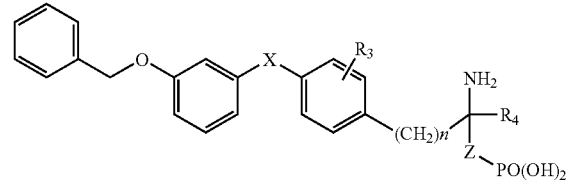

(1b)

wherein Z is —$CH_2$—, —CH=CH—, —CH=CF—, —$CH_2CH_2$—, —$CH_2CHF$—, —$CH_2CF_2$— or —CH(OH)$CF_2$—;

and X, $R_3$, $R_4$ and n are as defined in claim 1.

5. The 3-aminophosphonic acid derivative according to claim 4, or the optical isomer, the pharmaceutically acceptable salt or the hydrate thereof, wherein $R_3$ is a chlorine atom.

6. The aminophosphonic acid ester derivative according to claim 1, or the pharmaceutically acceptable salt or the hydrate thereof, wherein the compound represented by the general formula (1) is 1) 2-amino-5-[4-(3-benzyloxyphenylthio)-2-chlorophenyl]-2-methylpentylphosphonic acid monoester,
2) 2-amino-4-[4-(3-benzyloxyphenylthio)-2-chlorophenyl]-2-methylbutylphosphonic acid monoester,
3) 2-amino-5-[4-(3-benzyloxyphenylthio)-2-chlorophenyl]-2-hydroxymethylpentylphosphonic acid monoester,
4) 2-amino-4-[4-(3-benzyloxyphenylthio)-2-chlorophenyl]-2-hydroxymethylbutylphosphonic acid monoester,
5) 3-amino-5-[4-(3-benzyloxyphenylthio)-2-chlorophenyl]-3-hydroxymethylpentylphosphonic acid, or
6) 3-amino-6-[4-(3-benzyloxyphenylthio)-2-chlorophenyl]-3-hydroxymethylhexylphosphonic acid.

7. A pharmaceutical composition containing as an active ingredient at least one of the aminophosphonic acid derivatives according to claim 1, and the optical isomers, the pharmaceutically acceptable salts and the hydrates thereof, and the pharmaceutically acceptable carrier.

8. A pharmaceutical composition containing as an active ingredient at least one of the aminophosphonic acid derivatives according to claim 2, and the optical isomers, the pharmaceutically acceptable salts and the hydrates thereof, and the pharmaceutically acceptable carrier.

9. A pharmaceutical composition containing as an active ingredient at least one of the aminophosphonic acid derivatives according to claim 3, and the optical isomers, the pharmaceutically acceptable salts and the hydrates thereof, and the pharmaceutically acceptable carrier.

10. A pharmaceutical composition containing as an active ingredient at least one of the aminophosphonic acid derivatives according to claim 4, and the optical isomers, the pharmaceutically acceptable salts and the hydrates thereof, and a pharmaceutically acceptable carrier.

11. A pharmaceutical composition containing as an active ingredient at least one of the aminophosphonic acid derivatives according to claim 5, and the optical isomers, the pharmaceutically acceptable salts and the hydrates thereof and a pharmaceutically acceptable carrier.

12. A pharmaceutical composition containing as an active ingredient at least one of the aminophosphonic acid derivatives according to claim 6, and the optical isomers, the pharmaceutically acceptable salts and the hydrates thereof, and a pharmaceutically acceptable carrier.

* * * * *